(12) United States Patent
Webster et al.

(10) Patent No.: US 10,184,008 B2
(45) Date of Patent: Jan. 22, 2019

(54) BLOOD BRAIN BARRIER TRANSPORT MOLECULES AND USES THEREOF

(71) Applicant: MEDIMMUNE LIMITED, Cambridge (GB)

(72) Inventors: Carl Innes Webster, Cambridge (GB); Albert George Thom, Cambridge (GB); Lutz U Jermutus, Cambridge (GB); Jonathan P Hatcher, Cambridge (GB)

(73) Assignee: MEDIMMUNE LIMITED, Cambridge (GB)

(*) Notice: Subject to any disclaimer, the term of this patent is extended or adjusted under 35 U.S.C. 154(b) by 0 days.

(21) Appl. No.: 15/536,371

(22) PCT Filed: Dec. 18, 2015

(86) PCT No.: PCT/EP2015/080539
§ 371 (c)(1),
(2) Date: Jun. 15, 2017

(87) PCT Pub. No.: WO2016/097315
PCT Pub. Date: Jun. 23, 2016

(65) Prior Publication Data
US 2018/0057605 A1   Mar. 1, 2018

Related U.S. Application Data

(60) Provisional application No. 62/094,503, filed on Dec. 19, 2014.

(51) Int. Cl.
*C07K 16/40* (2006.01)
*A61K 47/68* (2017.01)
*A61K 39/00* (2006.01)

(52) U.S. Cl.
CPC .......... *C07K 16/40* (2013.01); *A61K 47/6811* (2017.08); *A61K 47/6849* (2017.08); *A61K 2039/505* (2013.01); *C07K 2317/22* (2013.01); *C07K 2317/24* (2013.01); *C07K 2317/515* (2013.01); *C07K 2317/52* (2013.01); *C07K 2317/565* (2013.01); *C07K 2317/569* (2013.01); *C07K 2317/622* (2013.01); *C07K 2317/77* (2013.01); *C07K 2317/94* (2013.01)

(58) Field of Classification Search
None
See application file for complete search history.

(56) References Cited

U.S. PATENT DOCUMENTS

2013/0287773 A1* 10/2013 Pardridge .......... C07K 16/2869
424/134.1

FOREIGN PATENT DOCUMENTS

| WO | 02057445 A1 | 7/2002 |
|---|---|---|
| WO | 2006099747 A1 | 9/2006 |
| WO | 2007036021 A1 | 4/2007 |
| WO | 2010080463 | 7/2010 |
| WO | 2013106577 A2 | 7/2013 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*

Abulrob A et al: "The blood-brain barrier transmigrating single domain antibody: mechanisms of transport and antigenic epitopes in human brain endothelial cells", Journal of Neurochemistry, Wiley Interscience, New York, NY, US, vol. 95, No. 4, Nov. 1, 2005 (Nov. 1, 2005), pp. 1201-1214.

* cited by examiner

*Primary Examiner* — Adam Weidner
(74) *Attorney, Agent, or Firm* — Cynthia Lan Martin

(57) ABSTRACT

The disclosure provides transporter molecules capable of carrying agents of interest across the blood brain barrier. Also provided are polynucleotides encoding transporter molecules, methods making transporter molecules, and methods of using transporter molecules, e.g., for the diagnosis, prevention, or treatment of central nervous system diseases, disorders, or injuries.

Figure 1:
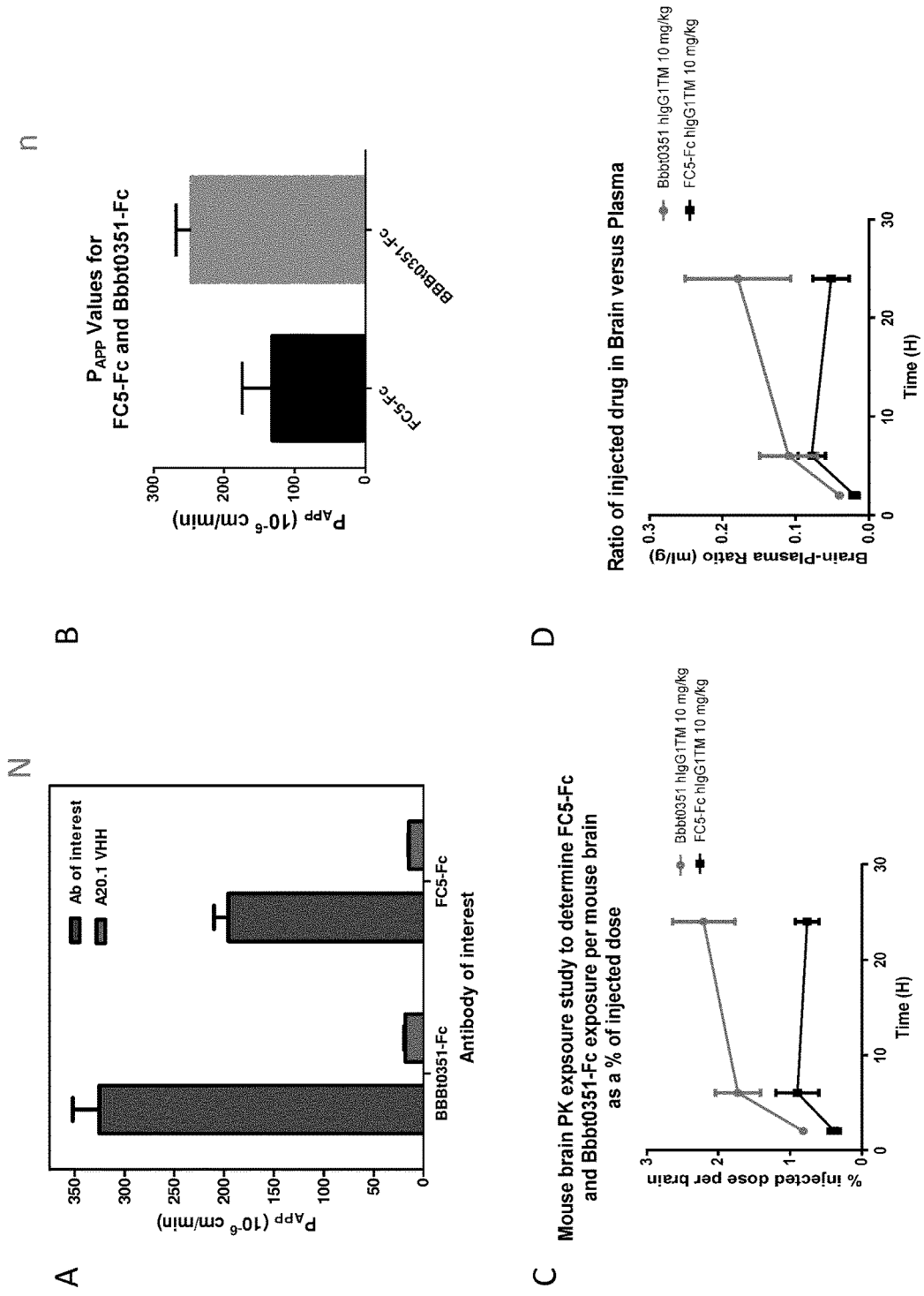

27 Claims, 15 Drawing Sheets
Specification includes a Sequence Listing.

FIGURE 6
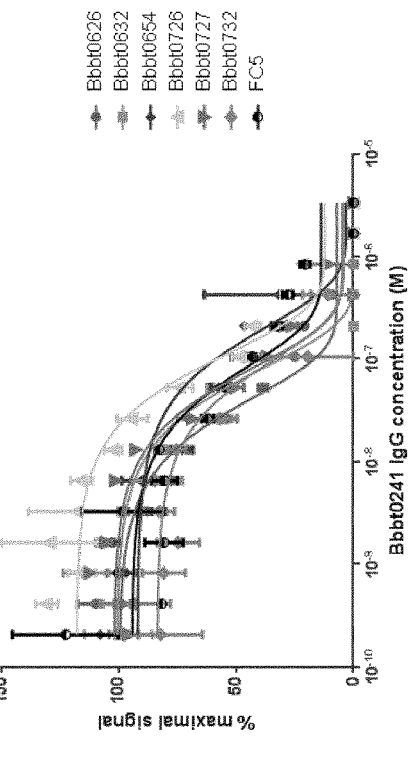
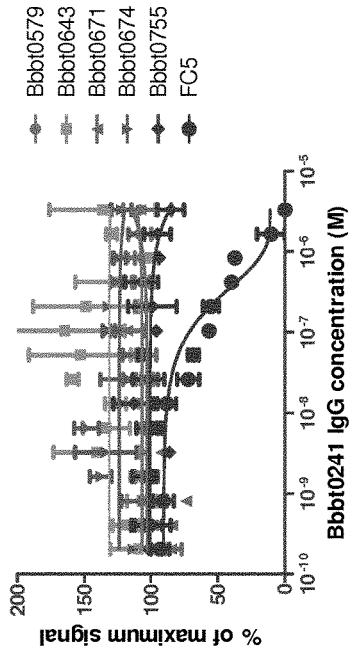

BLOOD BRAIN BARRIER TRANSPORT MOLECULES AND USES THEREOF

CROSS-REFERENCE TO RELATED APPLICATIONS

This application is a U.S. National Stage application of International Application No. PCT/EP2015/080539, filed on Dec. 18, 2015, said International Application No. PCT/EP2015/080539 claims benefit under 35 U.S.C. § 119(e) of the U.S. Provisional Application No. 62/094,503, filed Dec. 19, 2014. Each of the above listed applications is incorporated by reference herein in its entirety for all purposes.

REFERENCE TO THE SEQUENCE LISTING

This application incorporates by reference a Sequence Listing submitted with this application as text file entitled BBB-100-US-PCT-SequenceListing, having a size of 83 kilobytes.

The content of the electronically submitted sequence listing in ASCII text file (BBB-100P1_Seq; Size: 84 kilobytes; and Date of Creation: Dec. 19, 2014) filed with the application is incorporated herein by reference in its entirety.

BACKGROUND OF THE INVENTION

The blood-brain barrier (BBB) protects and regulates the homeostasis of the brain and prevents the free passage of molecules into most parts of the brain, thereby limiting the treatment of many brain diseases. Transport of essential molecules such as nutrients, growth factors and hormones is achieved via a series of specific transporters and receptors that regulate passage across the brain endothelial cells. The delivery of biologics, and other drugs, to the brain therefore represents a significant challenge. Additionally, transport mechanisms appear to exist that rapidly remove antibodies from the brain presumably to prevent inflammatory responses due to engagement of Fc with effector ligands that promote a proinflammatory response.

Over the last decade reports of antibody transport across the blood brain barrier have emerged where binding to the extracellular domain of the transporter molecules facilitates transcytosis of the receptor antibody complex across the endothelial cell layer.

The blood-brain barrier is mainly formed by brain capillary endothelial cells (BCECs) (Rubin & Staddon, Ann. Rev. Neurosci. 1999; 22:11-28), although other cell types, such as pericytes, astrocytes and neuronal cells, also play an important role in the function of the BBB. BCECs have specific characteristics, such as tight junctions, which prevent paracellular transport of small and large (water soluble) compounds from the blood to the brain (Brightman & Reese, J. Cell Biol. 1969; 40(3):648-77; Reese & Karnovsky, J. Cell Biol. 1967; 34(1):207-17). The BBB functions as a physical, metabolic and immunological barrier (Gaillard et al., Microvasc. Res. 2003; 65(1):24-31).

A single domain antibody (Llama) called FC5 that is able to cross the BBB was identified by an academic lab (Muruganandam et al., FASEB 2001; Abulrob et al., J. Neurochemistry 2005; 95:1201-1214; PCT Publication No. WO 02/057445 A1, U.S. Pat. No. 8,383,107) using human brain endothelial cell surface selections. FC5 is species cross reactive and can bind to brain endothelial cells of rat, mouse, cyno and human. The putative receptor for this antibody is TMEM30a, also referred to as transmembrane protein 30A, cdc50a, FLJ10856, or C6orf67. This is an orphan receptor where the exact function is unknown. It is thought to play a role in aminophospholipid translocation where the complex is composed of at least two proteins: an alpha subunit from the P4 subfamily of P-type ATPases and a beta subunit from the CDC50-Lemp3 family which includes TMEM30a (cdc50a) (Chen et al., J. Immunol. 2011; 186:3215-3225; Munoz-Martinez et al., Biochemical Pharmacology 2010; 80:793-800).

BRIEF SUMMARY

This disclosure provides blood brain barrier transporter molecules with properties similar to the single domain camelid antibody FC5 that have been reformatted as functional molecules suitable for use in humans.

In one aspect, the disclosure provides an isolated transporter molecule that includes an immunoglobulin polypeptide, where the polypeptide comprises an immunoglobulin heavy chain complementarity-determining region-1 (H-CDR1), an immunoglobulin heavy chain complementarity-determining region-2 (H-CDR2), an immunoglobulin heavy chain complementarity-determining region-3 (H-CDR3), an immunoglobulin light chain complementarity-determining region-1 (L-CDR1), an immunoglobulin light chain complementarity-determining region-2 (L-CDR2), and an immunoglobulin light chain complementarity-determining region-3 (L-CDR3); where the H-CDR1, H-CDR2, H-CDR3, L-CDR1, L-CDR2, and L-CDR3 are, respectively: (a) SEQ ID NO: 3, SEQ ID NO: 4, SEQ ID NO: 5, SEQ ID NO: 12, SEQ ID NO: 13, and SEQ ID NO: 14; (b) SEQ ID NO: 21, SEQ ID NO: 22, SEQ ID NO: 23, SEQ ID NO: 229, SEQ ID NO: 230, and SEQ ID NO: 231; (c) SEQ ID NO: 39, SEQ ID NO: 40, SEQ ID NO: 41, SEQ ID NO: 229, SEQ ID NO: 230, and SEQ ID NO: 231; (d) SEQ ID NO: 57, SEQ ID NO: 58, SEQ ID NO: 59, SEQ ID NO: 66, SEQ ID NO: 67, and SEQ ID NO: 68; (e) SEQ ID NO: 75, SEQ ID NO: 76, SEQ ID NO: 77, SEQ ID NO: 229, SEQ ID NO: 230, and SEQ ID NO: 231; (f) SEQ ID NO: 93, SEQ ID NO: 94, SEQ ID NO: 95, SEQ ID NO: 229, SEQ ID NO: 230, and SEQ ID NO: 231; (g) SEQ ID NO: 111, SEQ ID NO: 112, SEQ ID NO: 113, SEQ ID NO: 229, SEQ ID NO: 230, and SEQ ID NO: 231; (h) SEQ ID NO: 129, SEQ ID NO: 130, SEQ ID NO: 131, SEQ ID NO: 138, SEQ ID NO: 139, and SEQ ID NO: 140; (i) SEQ ID NO: 147, SEQ ID NO: 148, SEQ ID NO: 149, SEQ ID NO: 156, SEQ ID NO: 157, and SEQ ID NO: 158; (j) SEQ ID NO: 165, SEQ ID NO: 166, SEQ ID NO: 167, SEQ ID NO: 174, SEQ ID NO: 175, and SEQ ID NO: 176; (k) SEQ ID NO: 183, SEQ ID NO: 184, SEQ ID NO: 185, SEQ ID NO: 192, SEQ ID NO: 193, and SEQ ID NO: 194; or (l) SEQ ID NO: 210, SEQ ID NO: 211, SEQ ID NO: 212, SEQ ID NO: 219, SEQ ID NO: 220, and SEQ ID NO: 220; and where the transporter molecule can cross the blood brain barrier.

In another aspect, the disclosure provides an isolated transporter molecule that includes an immunoglobulin polypeptide, where the polypeptide comprises: (a) an immunoglobulin heavy chain variable region (VH) amino acid sequence at least 90%, 95%, 96%, 97%, 98%, or 99% identical to SEQ ID NO: 2 and an immunoglobulin light chain variable region (VL) amino acid sequence at least 90%, 95%, 96%, 97%, 98%, or 99% identical to SEQ ID NO: 11 (b) a VH amino acid sequence at least 90%, 95%, 96%, 97%, 98%, or 99% identical to SEQ ID NO: 20 and a VL amino acid sequence at least 90%, 95%, 96%, 97%, 98%, or 99% identical to SEQ ID NO: 29 (c) a VH amino acid sequence at least 90%, 95%, 96%, 97%, 98%, or 99% identical to SEQ ID NO: 38 and a VL amino acid sequence at least 90%, 95%, 96%, 97%, 98%, or 99% identical to SEQ ID NO: 47 (d) a VH amino acid sequence at least 90%, 95%, 96%, 97%, 98%, or 99% identical to SEQ ID NO: 56 and a VL amino acid sequence at least 90%, 95%, 96%, 97%, 98%, or 99% identical to SEQ ID NO: 65 (e) a VH amino acid sequence at least 90%, 95%, 96%, 97%, 98%, or 99% identical to SEQ ID NO: 74 and a VL amino acid sequence at least 90%, 95%, 96%, 97%, 98%, or 99% identical to SEQ ID NO: 83 (f) a VH amino acid sequence at least 90%, 95%, 96%, 97%, 98%, or 99% identical to SEQ ID NO: 92 and a VL amino acid sequence at least 90%, 95%, 96%, 97%, 98%, or 99% identical to SEQ ID NO: 101 (g) a VH amino acid sequence at least 90%, 95%, 96%, 97%, 98%, or 99% identical to SEQ ID NO: 110 and a VL amino acid sequence at least 90%, 95%, 96%, 97%, 98%, or 99% identical to SEQ ID NO: 119 (h) a VH amino acid sequence at least 90%, 95%, 96%, 97%, 98%, or 99% identical to SEQ ID NO: 128 and a VL amino acid sequence at least 90%, 95%, 96%, 97%, 98%, or 99% identical to SEQ ID NO: 137 (i) a VH amino acid sequence at least 90%, 95%, 96%, 97%, 98%, or 99% identical to SEQ ID NO: 146 and a VL amino acid sequence at least 90%, 95%, 96%, 97%, 98%, or 99% identical to SEQ ID NO: 155 (j) a VH amino acid sequence at least 90%, 95%, 96%, 97%, 98%, or 99% identical to SEQ ID NO: 164 and a VL amino acid sequence at least 90%, 95%, 96%, 97%, 98%, or 99% identical to SEQ ID NO: 173 (k) a VH amino acid sequence at least 90%, 95%, 96%, 97%, 98%, or 99% identical to SEQ ID NO: 182 and a VL amino acid sequence at least 90%, 95%, 96%, 97%, 98%, or 99% identical to SEQ ID NO: 191 (1) a VH amino acid sequence at least 90%, 95%, 96%, 97%, 98%, or 99% identical to SEQ ID NO: 209 and a VL amino acid sequence at least 90%, 95%, 96%, 97%, 98%, or 99% identical to SEQ ID NO: 218; or (m) a VH amino acid sequence at least 90%, 95%, 96%, 97%, 98%, or 99% identical to SEQ ID NO: 226 and a VL amino acid sequence at least 90%, 95%, 96%, 97%, 98%, or 99% identical to SEQ ID NO: 227; and where the transporter molecule can cross the blood brain barrier.

In another aspect, the disclosure provides an isolated transporter molecule that includes an immunoglobulin polypeptide, where the polypeptide comprises a single domain VH with the amino acid sequence SEQ ID NO: 200. In certain aspects, the transporter molecule can cross brain microvascular endothelial cells BMVEC more effectively than FC5 in an in vitro transcytosis assay.

A transporter molecule as provided herein can further include a heavy chain constant region, or fragment thereof, e.g., including an Fc region and/or a hinge region. Furthermore, the immunoglobulin polypeptide of a transporter molecule as provided herein can include an antibody or a BBB-penetrable fragment thereof. In certain aspects, the antibody or BBB-penetrable fragment thereof can include two or more subunits, e.g., a heavy chain and a light chain associated via disulfide bonds. In certain aspects, the heavy chain constant region or fragment thereof can be an IgG constant region or fragment thereof. In certain aspects, the antibody or fragment thereof can be a murine antibody, a humanized antibody, a chimeric antibody, a monoclonal antibody, a recombinant antibody, a multispecific antibody, any combination thereof, or any antigen-binding fragment thereof. In certain aspects, the antibody or fragment thereof can be a complete IgG immunoglobulin that includes two heavy chains and two light chains. In certain aspects, the BBB-penetrable fragment thereof can be an Fv fragment, an Fab fragment, an F(ab')2 fragment, an Fab' fragment, a dsFv fragment, a scFv fragment, or an sc(Fv)2 fragment. For example, the fragment can include a scFv fragment, where the ScFv comprises a VH and a VL fused together via a linker, or a dsFv fragment, where the dsFv comprises a VH and a VL fused together via a linker. In certain aspects, the scFv or dsFv can include, from the amino terminus: VH-L-VL, where L is the linker. In certain aspects, the linker can be (Gly4Ser)n, where n is a positive integer selected from the group consisting of 1, 2, 3, 4, 5, 6, 7, 8, 9 and 10 (SEQ ID NO: −232), Ser(Gly4Ser)n, where n is a positive integer selected from the group consisting of 1, 2, 3, 4, 5, 6, 7, 8, 9 and 10 (SEQ ID NO: 233), GGGGSGGGGSGGGGS (SEQ ID NO: 234), GGGGSGGGGSGGGG (SEQ ID NO: 235), GGGGSGGGGSGGGGSAL (SEQ ID NO: 236), or GGGGSGGGGSGGGGSA (SEQ ID NO: 237).

In certain aspects, the IgG constant domain or fragment thereof can include one or more amino acid substitutions relative to a wild-type IgG constant domain where the modified IgG has an altered half-life and/or altered binding affinity for FcRn compared to the half-life of an IgG having the wild-type IgG constant domain. In one example, the modified IgG can have an increased half-life and/or an increased binding affinity for FcRn compared to the half-life of an IgG having the wild-type IgG constant domain. In another example, the modified IgG has a decreased half-life and/or a decreased binding affinity for FcRn compared to the half-life of an IgG having the wild-type IgG constant domain. In certain aspects, the IgG constant domain or fragment thereof can include one or more amino acid substitutions relative to a wild-type IgG constant domain where the modified IgG has reduced effector function and/or reduced binding to at least one effector molecule compared to the half-life of an IgG having the wild-type IgG constant domain. In certain aspects, the IgG constant domain or fragment thereof can have an altered glycosylation relative to a wild-type IgG constant domain, where the modified IgG has reduced effector function and/or reduced binding to at least one effector molecule compared to the half-life of an IgG having the wild-type IgG constant domain. In certain aspects, the heavy chain constant domain or fragment thereof of a transporter molecule provided herein can be a human IgG1, IgG2, IgG3, or IgG4 constant domain or fragment thereof.

In certain aspects, a transporter molecule as provided herein can further include a light chain constant domain or fragment thereof. For example, the light chain constant domain or fragment thereof can be a human kappa constant domain or fragment thereof, or a human lambda constant region or fragment thereof.

In certain aspects, a transporter molecule as provided herein can further include an associated payload, where the transporter molecule can transport the payload across the BBB. In certain aspects, the payload is fused, via a peptide bond, to the immunoglobulin-derived polypeptide. In certain aspects, the payload is chemically conjugated to the immunoglobulin-derived polypeptide. In certain aspects, the payload is associated with the immunoglobulin-derived polypeptide via non-covalent bonds.

A payload can include, for example, an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a polyethylene glycol (PEG) molecule, or a combination of two or more of the agents. For example, the payload can include a neuroactive polypeptide, for example, a neurotrophic factors, endocrine factors, growth factors, paracrine factors, hypothalamic release factors, neurotransmitter polypeptides, polypeptide agonists for a receptor expressed by a CNS cell, polypeptides involved in lysosomal storage disease or any combination thereof. In another example, the payload can include an IL-1 receptor antagonist (IL-1Ra), dalargin, an interferon-β, Glial-derived neurotrophic factor (GDNF), tumor necrosis factor receptor (TNFR), nerve growth factor (NGF), brain derived neurotrophic factor (BDNF), neurotrophin-4/5, neurotrophin (NT)-3, a neurturin, neuregulin, a netrin, ciliary neurotrophic factor (CNTF), stem cell factor (SCF), a semaphorin, hepatocyte growth factor (HGF), epidermal growth factor (EGF), transforming growth factor (TGF)-cx, TGF-B, vascular endothelial growth factor (VEGF), platelet-derived growth factor (PDGF), heregulin, artemin, persephin, interleukins, granulocyte-colony stimulating factor (CSF), granulocyte-macrophage-CSF, cardiotrophin-1, hedgehogs, leukemia inhibitory factor (LIF), midkine, pleiotrophin, erythropoietin (EPO), bone morphogenetic proteins (BMPs), netrins, saposins, any fragment thereof, or any combination thereof. In one aspect, a transporter molecule as provided herein can include a human IgG heavy chain constant region or fragment thereof, and a human light chain constant region, and where the IL-1Ra polypeptide is fused to the C-terminus of the heavy chain constant region.

In certain aspects, the payload can include a heterologous antibody or fragment thereof, for example, a heterologous antibody or fragment thereof specifically binds to one or more of beta-secretase 1 (BACE1), CD20, CD25, CD52, CD33, CTLA-4, tenascin, alpha-4 (a4) integrin, IL-12, IL-23, the p40 subunit of IL-12/IL-23, amyloid-13 (AI3), Huntingtin, nerve growth factor (NGF), epidermal growth factor receptor (EGFR/HER1), human epidermal growth factor receptor 2 (HER2/neu), vascular endothelial growth factor (VEGF), TrkA, TNF-a, TNF-13, α-synuclein Tau, apolipoprotein E4 (ApoE4), prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), caspase 6, a neurotrophic factor and/or a neurotrophic factor receptor. In certain aspects, a transporter molecule as provided herein can bind to brain microvascular endothelial cells (BMVECs), e.g., human, cynomolgus monkey, murine, rat, or bovine BMVECs. In certain aspects, the BMVECs are brain capillary endothelial cells (BCECs). In certain aspects a transporter molecule as provided herein can pass through a monolayer of BCECs in an in vitro transcytosis assay.

In certain aspects, a transporter molecule as provided herein can compete with the single-domain antibody FC5 or Bbbt0241 for binding to brain endothelial cells. Exemplary transporter molecules of this type include the VH and VL domains of Bbbt0626, Bbbt0727, Bbbt0632, Bbbt0654, Bbbt0726, Bbbt0732, or Bbbt0754.

In certain aspects, a transporter molecule as provided herein does not compete with the single-domain antibody FC5 or Bbbt0241 for binding to brain endothelial cells. Exemplary transporter molecules of this type include the VH and VL domains of, Bbbt0643, Bbbt0674, Bbbt0755, Bbbt0351, Bbbt0579 or Bbbt0671.

In certain aspects, a transporter molecule as provided herein, when conjugated to dynorphin and administered peripherally in a rat model, can cross the BBB thereby inducing diuresis. In certain aspects, a transporter molecule as provided herein, when fused to IL-1Ra and administered peripherally in a rat partial sciatic nerve ligation assay, can cross the BBB thereby reducing neuropathic pain. In certain aspects, a transporter molecule as provided herein, when administered peripherally in a mouse model, localizes in the cortex of cerebellum, the gray matter of the cerebrum, the gray matter of the spinal cord, the pons, or a combination thereof, as measured by quantitative whole body autoradiography.

The disclosure further provides a composition that includes a transporter molecule as provided herein, and a carrier.

The disclosure further provides an isolated polynucleotide that includes a nucleic acid molecule encoding a transporter molecule as provided herein, or a fragment or subunit thereof. In certain aspects, the nucleic acid molecule can encode a VH, a VL, or a VH and a VL, where the nucleic acid molecule comprises SEQ ID NO: 2, SEQ ID NO: 11, or SEQ ID NO: 2 and SEQ ID NO: 11; SEQ ID NO: 20, SEQ ID NO: 29, or SEQ ID NO: 20 and SEQ ID NO: 29; SEQ ID NO: 38, SEQ ID NO: 47, or SEQ ID NO: 38 and SEQ ID NO: 47; SEQ ID NO: 56, SEQ ID NO: 65, or SEQ ID NO: 66 and SEQ ID NO: 65; SEQ ID NO: 74, SEQ ID NO: 83, or SEQ ID NO: 74 and SEQ ID NO: 83; SEQ ID NO: 92, SEQ ID NO: 101, or SEQ ID NO: 92 and SEQ ID NO: 101; SEQ ID NO: 110, SEQ ID NO: 119, or SEQ ID NO: 110 and SEQ ID NO: 119; SEQ ID NO: 128, SEQ ID NO: 137, or SEQ ID NO: 128 and SEQ ID NO: 137; SEQ ID NO: 146, SEQ ID NO: 155, or SEQ ID NO: 146 and SEQ ID NO: 155; SEQ ID NO: 164, SEQ ID NO: 173, or SEQ ID NO: 164 and SEQ ID NO: 173; SEQ ID NO: 182, SEQ ID NO: 191, or SEQ ID NO: 182 and SEQ ID NO: 191; SEQ ID NO: 200; SEQ ID NO: 209, SEQ ID NO: 218, or SEQ ID NO: 209 and SEQ ID NO: 218; or SEQ ID NO: 226, SEQ ID NO: 227, or SEQ ID NO: 226 and 227. In certain aspects, the polynucleotide as provided herein further includes a nucleic acid that encodes a payload, such as those described above.

The disclosure further provides a composition that includes two or more nucleic acid molecules encoding a transporter molecule as provided herein, or a fragment or subunit thereof. In certain aspects, the two or more nucleic acid molecules can include, respectively, SEQ ID NO: 2 and SEQ ID NO: 11; SEQ ID NO: 20 and SEQ ID NO: 29; SEQ ID NO: 38 and SEQ ID NO: 47; SEQ ID NO: 56 and SEQ ID NO: 65; SEQ ID NO: 74 and SEQ ID NO: 83; SEQ ID NO: 92 and SEQ ID NO: 101; SEQ ID NO: 110 and SEQ ID NO: 119; SEQ ID NO: 128 and SEQ ID NO: 137; SEQ ID NO: 146 and SEQ ID NO: 155; SEQ ID NO: 164 and SEQ ID NO: 173; SEQ ID NO: 182 and SEQ ID NO: 191; SEQ ID NO: 209 and SEQ ID NO: 218; or SEQ ID NO: 226 and SEQ ID NO: 227. In certain aspects, the composition can further include a nucleic acid molecule encoding a payload. In certain aspects the two or more nucleic acid molecules of the composition are situated in the same vector. In certain aspects the two or more nucleic acid molecules are situated in at least two separate vectors.

The disclosure further provides a vector that includes an isolated polynucleotide as provided herein, or the two or more nucleic acid molecules of a composition as provided herein.

In certain aspects, a polynucleotide nucleic acid molecule as provided herein can be operably associated with one or more promoters.

In certain aspects, the disclosure provides an isolated host cell that includes a vector as provided herein, or a composition of two or more vectors as provided herein. The disclosure further provides a method of making a transporter molecule as provided herein, where the method includes (a) culturing the provided host cell; and (b) isolating the transporter molecule or fragment or subunit thereof. In certain aspects the method further includes (c) conjugating the transporter molecule or fragment or subunit thereof to a payload.

In certain aspects the disclosure provides a diagnostic reagent that includes a transporter molecule as provided herein, a composition as provided herein, a polynucleotide as provided herein, a vector as provided herein, or a host cell as provided herein. In certain aspects the disclosure provides a kit that includes a transporter molecule as provided herein, a composition as provided herein, a polynucleotide as provided herein, a vector as provided herein, or a host cell as provided herein.

In another aspect, the disclosure provides a method of treating a disease, disorder, or injury of the central nervous system (CNS), where the method includes peripherally administering to a subject in need of treatment a composition that includes a transporter molecule as provided herein, where the transporter molecule comprises a therapeutic agent capable of treating the disease, disorder, or injury upon exposure to the CNS following transport across the BBB, and where an amount of the therapeutic agent sufficient to treat the disease, disorder, or injury is transported across the BBB, thereby treating the disease, disorder, or injury. In certain aspects, the therapeutic agent is released from the transporter molecule following entry into the CNS. In certain aspects, the disease, disorder, or injury of the CNS can be, without limitation, multiple sclerosis (MS), amylotrophic lateral sclerosis (ALS), Huntington's disease, Alzheimer's disease, Parkinson's disease, spinal cord injury, traumatic brain injury, stroke, neuropathic pain, neurodegeneration, neuroinflammation, progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease), Wallerian Degeneration, optic neuritis, transverse myelitis, post radiation injury, neurologic complications of chemotherapy, acute ischemic optic neuropathy, vitamin E deficiency, isolated vitamin E deficiency syndrome, Bassen-Kornzweig syndrome, Marchiafava-Bignami syndrome, metachromatic leukodystrophy, trigeminal neuralgia, Bell's palsy, primary tumors, secondary metastases, or any combination thereof. In one aspect, the therapeutic agent is interleukin-1 receptor antagonist (IL-1Ra), and the disease, disorder, or injury is neuropathic pain.

The disclosure further provides a method of increasing the exposure of the CNS of a subject to an agent, where the method includes coupling the agent to a transporter molecule as provided herein and peripherally administering the coupled agent. The disclosure further provides a method of transporting an agent across the BBB that includes coupling the agent to a transporter molecule as provided herein, such that the transporter molecule transports the agent coupled thereto across the BBB.

BRIEF DESCRIPTION OF THE DRAWINGS/FIGURES

FIG. 1 shows the extent of transcytosis of Bbbt0351 through an immortalized rat brain endothelial cell line, (SV-ARBEC) (panel A), and primary rat brain endothelial cells (panel B). The results are shown as apparent permeability (in cm/min) on the y axis. A: comparison of transcytosis of Bbbt0351-Fc or FC5-Fc and a negative control VHH antibody through SV-ARBEC cells measured by nanoLC-SRM mass spectrometry (Haqqani A. S., et al., Method. Mol. Pharmaceutics. 2013; 10, 1542-1556); B: direct comparison of transcytosis of FC5-Fc and Bbbt0351-Fc through primary rat brain endothelial cells measured by nanoLC-SRM mass spectrometry. Both FC5 and Bbbt0351 were genetically fused to the hinge region of a human IgG1 Fc; C. Comparison of the brain exposure of FC5-Fc and Bbbt0351-Fc to mouse brain, over a 24 H period, after intra-venous injection at 10 mg/kg; Mice were perfused with PBS, brains were removed and homogenized in the presence of a mild detergent to release BBB targeted molecule into the soluble fraction, post centrifugation. Brain exposure was measured via Mesoscale Discovery assay technology (MSD). MSD utilizes electrochemiluminescence detection to detect binding events on array plates. A mouse monoclonal anti-human Fc capture antibody is used to capture the analyte, in this case either FC5-Fc or Bbbt0351-Fc and this capture event is subsequently detected via binding of a fluorescently tagged sheep anti-human IgG (H+L). D: Comparison of the ratio of injected FC5-Fc and Bbbt0351-Fc in brain when compared to that in plasma at distinct time points during the first 24 hours after i.v. dosing.

Figure 2:
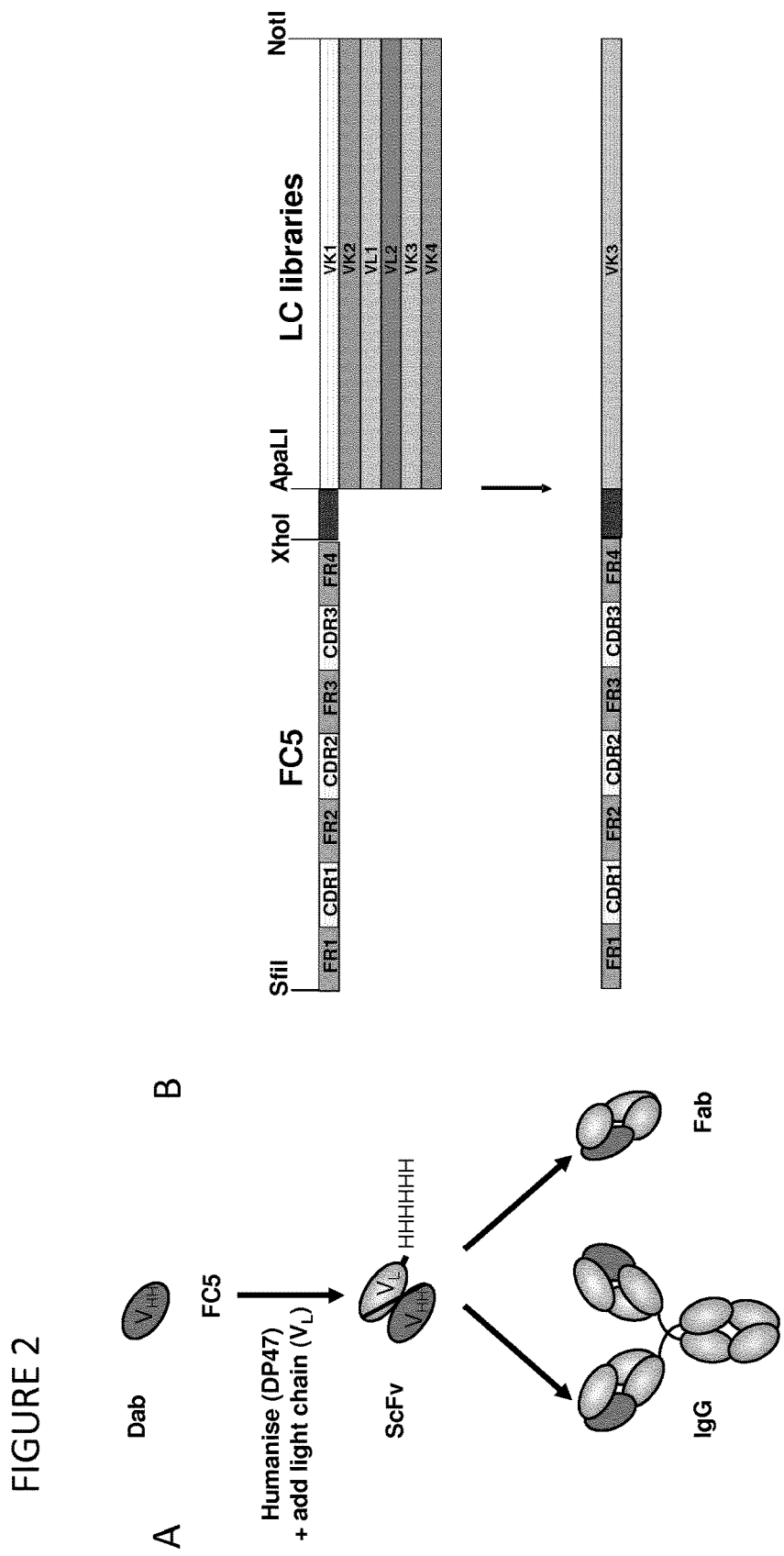

FIG. 2A shows a schematic of construction of single-chain Fv (scFv) Bbbt0241, a humanized version of FC5, and subsequent addition of human IgG1 and kappa constant regions to form a full IgG molecule or a Fab molecule. FIG. 2B shows the construction of a scFv library. FC5 domain antibody was directionally cloned via SfiI and XhoI endonuclease restriction sites into a heavy chain acceptor vector containing a library of light chains previously described during the CAT 2.0 library build (Lloyd C, et al., Protein Eng Des Sel 2009; 22 (3); 159-68).

Figure 3:
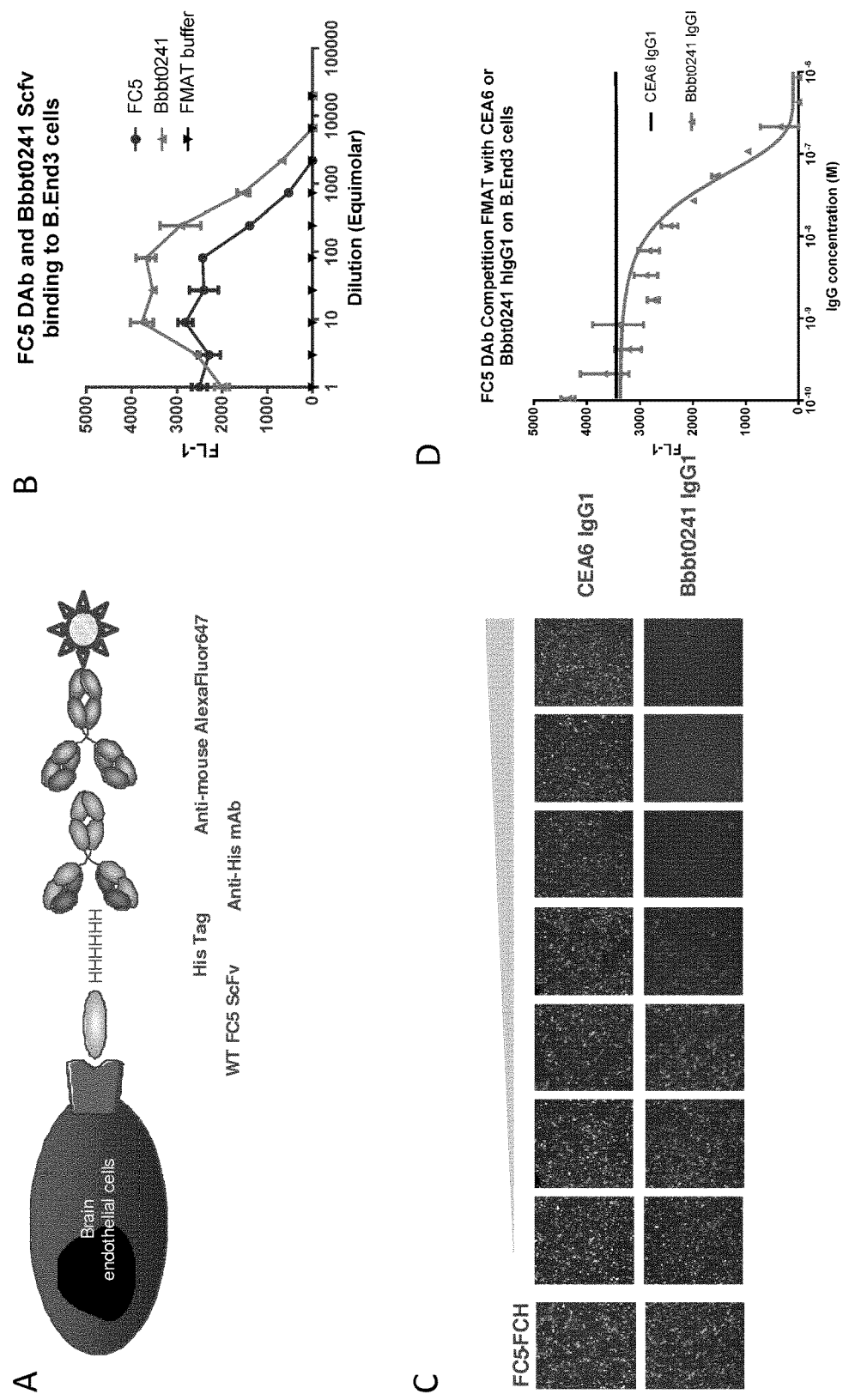

FIG. 3A shows a schematic of the Fluorescence Microvolume Assay Technology (FMAT) assay (Miraglia S, et al., J Biomol Screen 1999; 4 (4); 193-204). The scFv of interest is depicted as an oval with a histidine tag, which is bound by a mouse anti-his monoclonal antibody, which is in turn bound by an anti-mouse monoclonal antibody labeled with AlexaFluor647. The complex, when bound to brain endothelial cells through the scFv, results in areas of fluorescence on the cells. This cell based fluorescence is gated and plotted as fluorescent units (FL-1) FIG. 3B shows binding of increasing dilutions of FC5 DAb and Bbbt0241 scFv to B.End3 cells in the FMAT assay. Results are expressed as fluorescent units (FL-1) FIG. 3C shows photographs of cells bound with FC5 Dab in the competition FMAT assay. A constant amount of FC5 Dab was incubated with increasing amounts of Bbbt0241 or control hIgG1. FIG. 3D is a graphical summary of the data presented in FIG. 3C.

Figure 4:
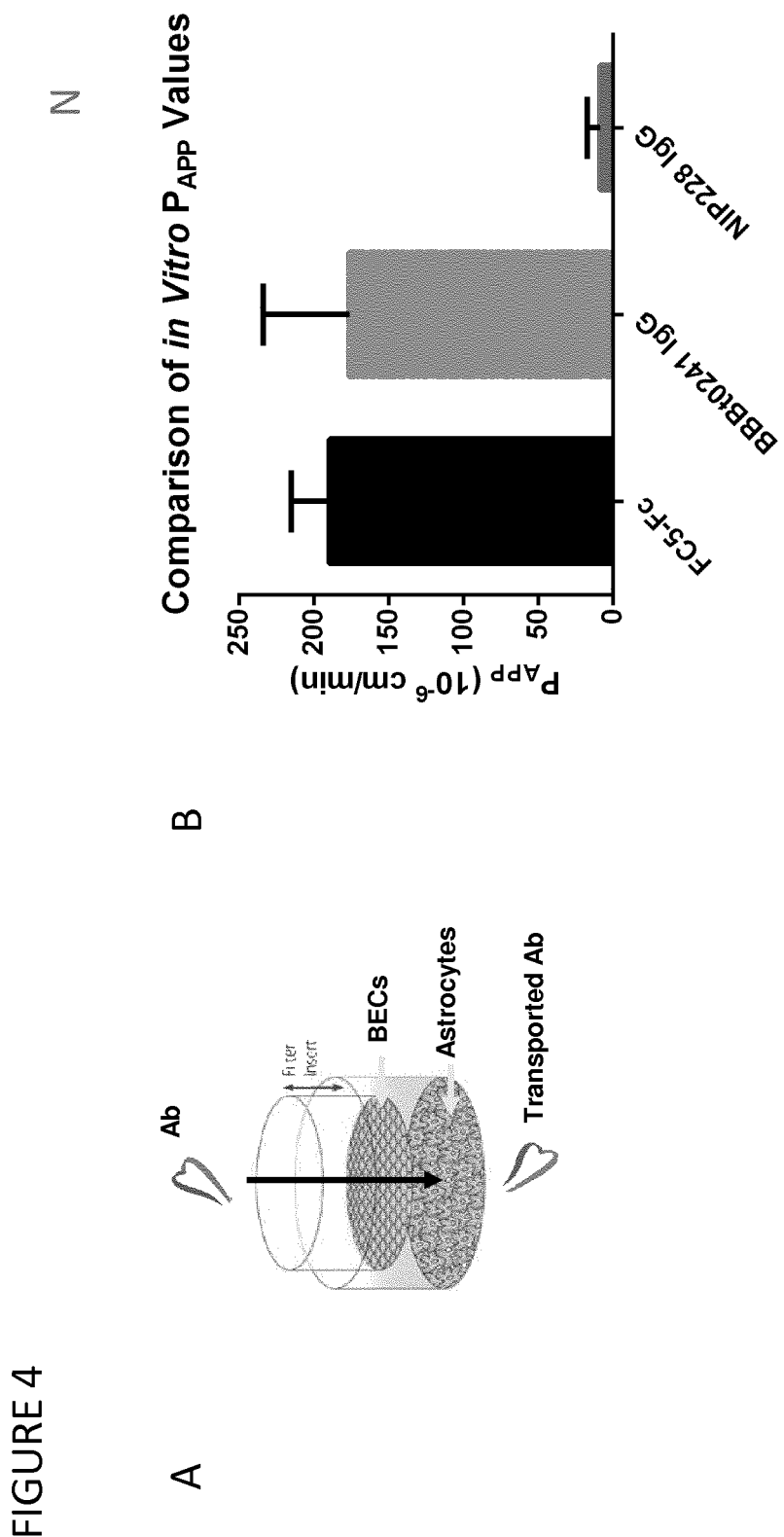

FIG. 4A shows a schematic of a single well in the in vitro transcytosis assay. FIG. 4B provides the $P_{APP}$ values that show the extent of in vitro transport of FC5-Fc, Bbbt0241 hIgG1, and NIP228 hIgG1, an isotype negative control IgG that was raised against a hapten (Nitrophenol conjugated to BSA) across SV-ARBEC cells in the in vitro transcytosis assay.

Figure 5:
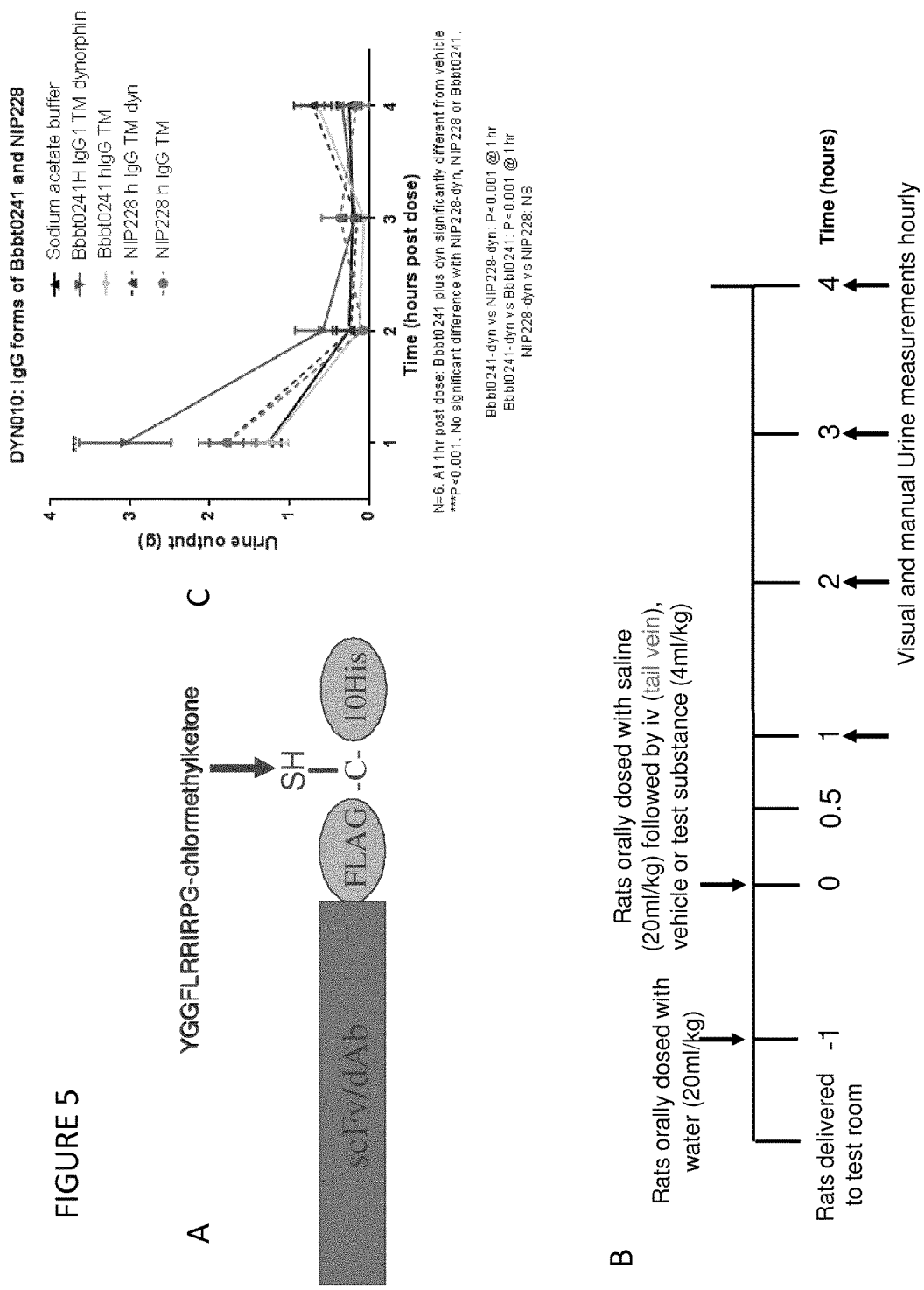

FIG. 5A is a schematic of a scFv molecule conjugated to the κ-opioid agonist dynorphin. FIG. 5B shows the study design for the diuresis model described in the Examples. FIG. 5C shows urine output over time in rats administered dynorphin-conjugated or free Bbbt0241 hIgG1TM, compared to dynorphin-conjugated or free negative control NIP228 hIgG1TM. n=6 for each group. P values are shown vs. vehicle and vs. the negative control. Data analyzed using 2-way ANOVA with time and treatment as dependent factors. Subsequent statistical significance obtained using Bonferroni's Post Hoc test.

FIG. 6A shows FMAT competition results using constant amounts of the FC5 mimetic ScFvs with increasing concentrations of Bbbt0241 IgG. FIG. 6B shows FMAT competition results using constant amounts of the FC5-like non-mimetic ScFvs with increasing concentrations of Bbbt0241 IgG.

Figure 7A:
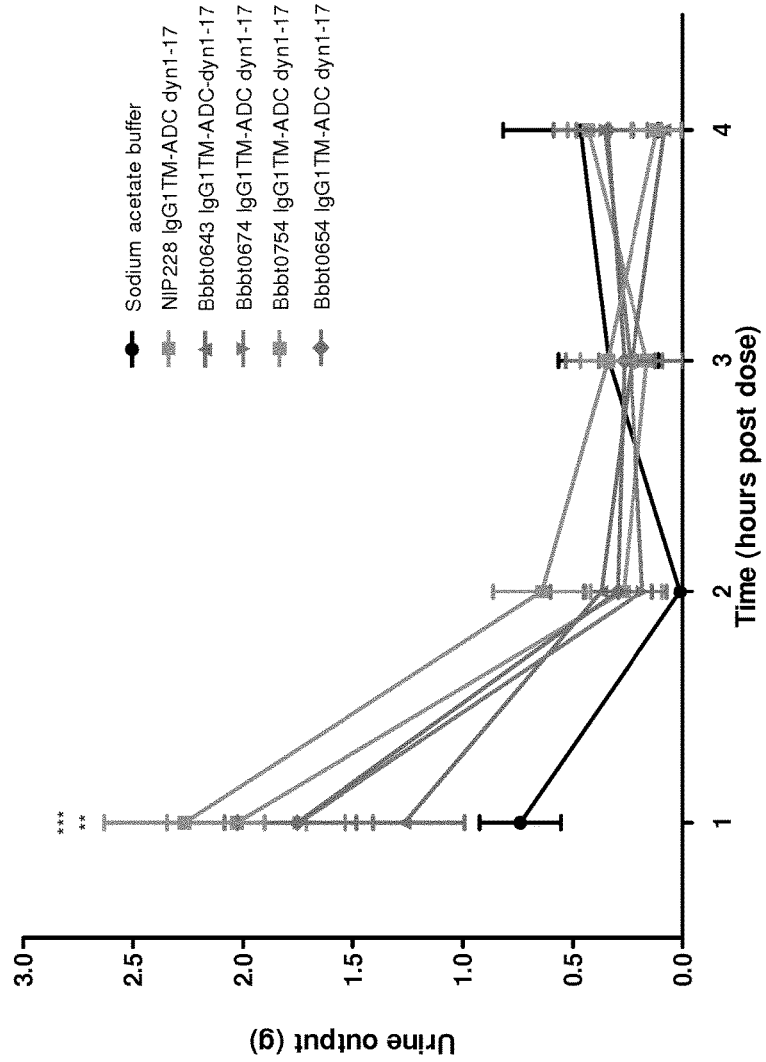
Figure 7B:
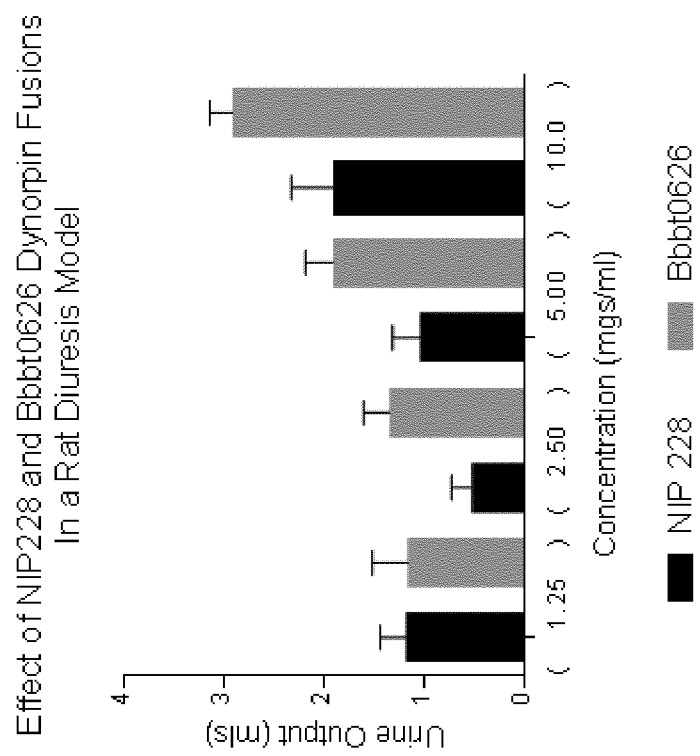

FIG. 7A shows urine output results upon administration of selected FC5 mimetic and non-mimetic dynorphin conjugates (IgG format) to rats. n=6. Data analyzed using 2-way ANOVA with time and treatment as dependent factors. Subsequent statistical significance obtained using Bonferroni's Post Hoc test. P values are shown. FIG. 7B shows urine output dose response curves upon administration of dynorphin-conjugated NIP228-IgG (black bars) and Bbbt0626-IgG (gray bars) to rats. n=6. Due to the number of animal being tested the experiment was run over 2 days. Results are presented as the combined data from both of those studies.

Figure 8:
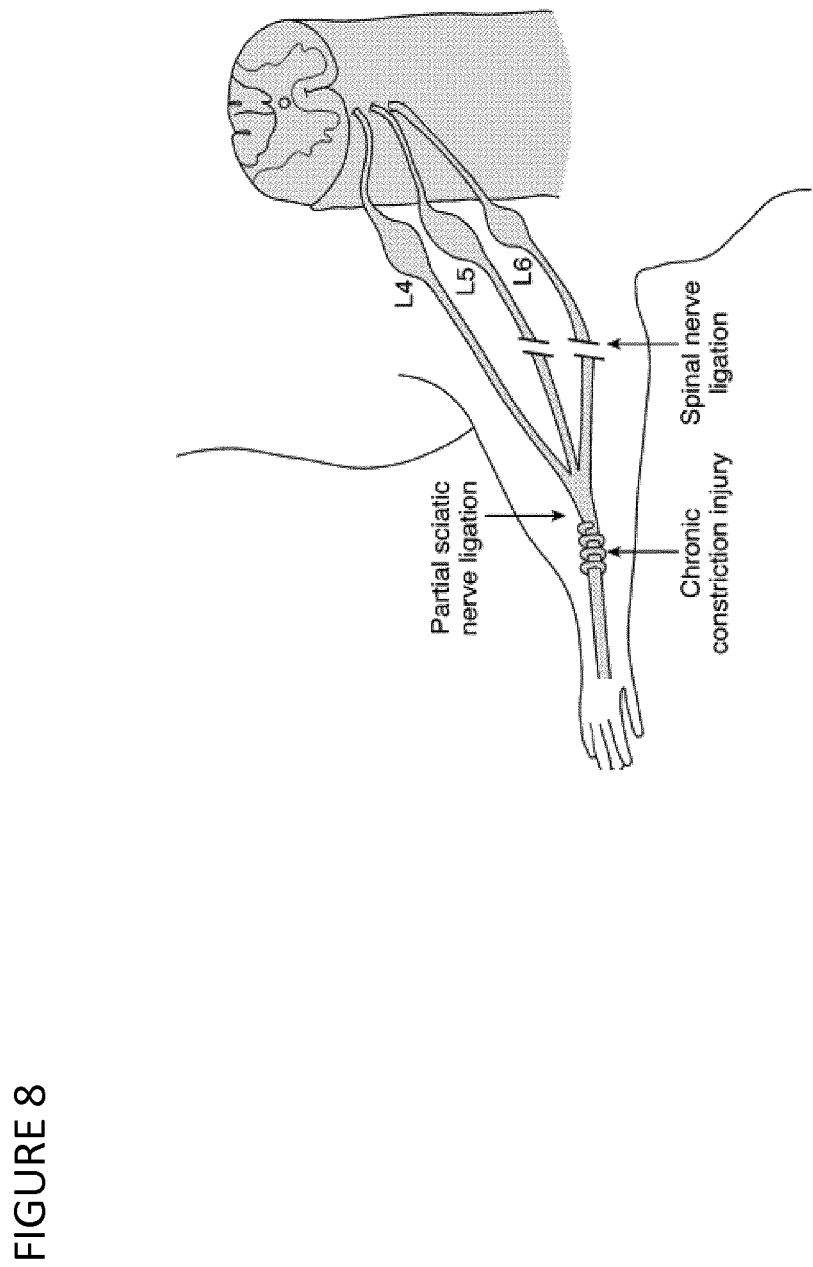

FIG. 8 is a cartoon showing a schematic surgery performed in the partial sciatic nerve ligation assay.

Figure 9:
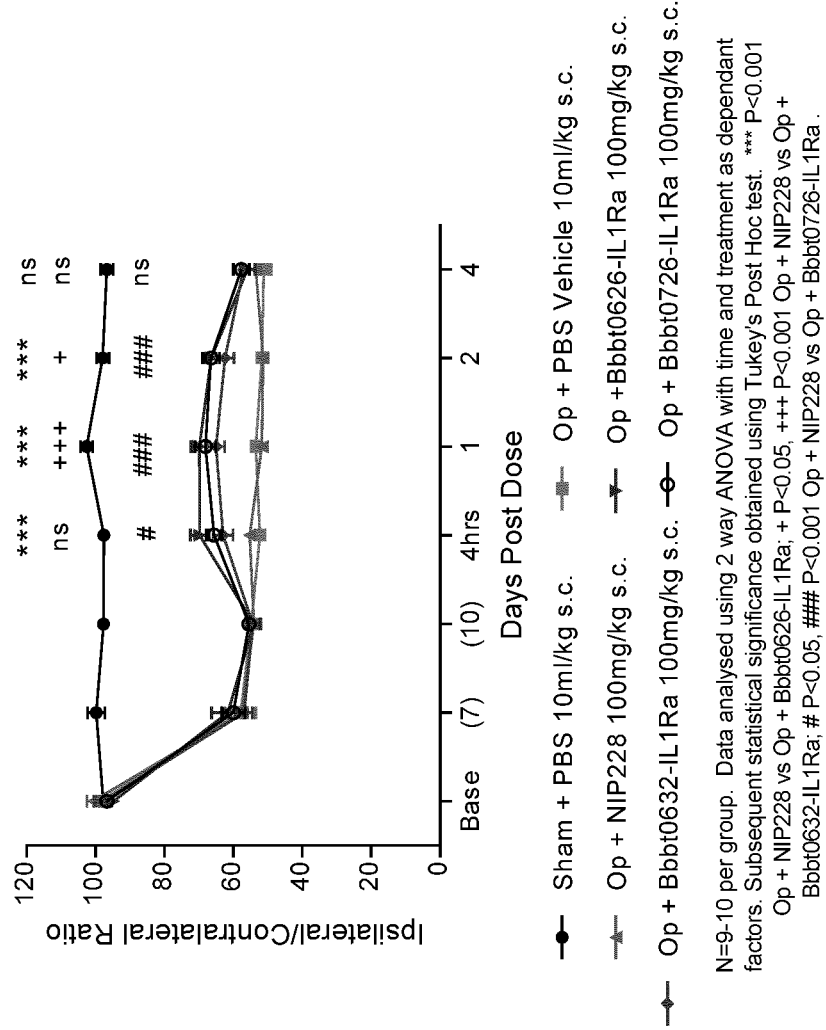

FIG. 9 shows the effect of FC5 mimetic-IL1Ra fusions on reversal of partial sciatic nerve ligation induced hyperalgesia in the rat. n=9-10 per group. Data analyzed using 2-way ANOVA with time and treatment as dependent factors. Subsequent statistical significance obtained using Tukey's Post Hoc test. P values are shown.

Figure 10:
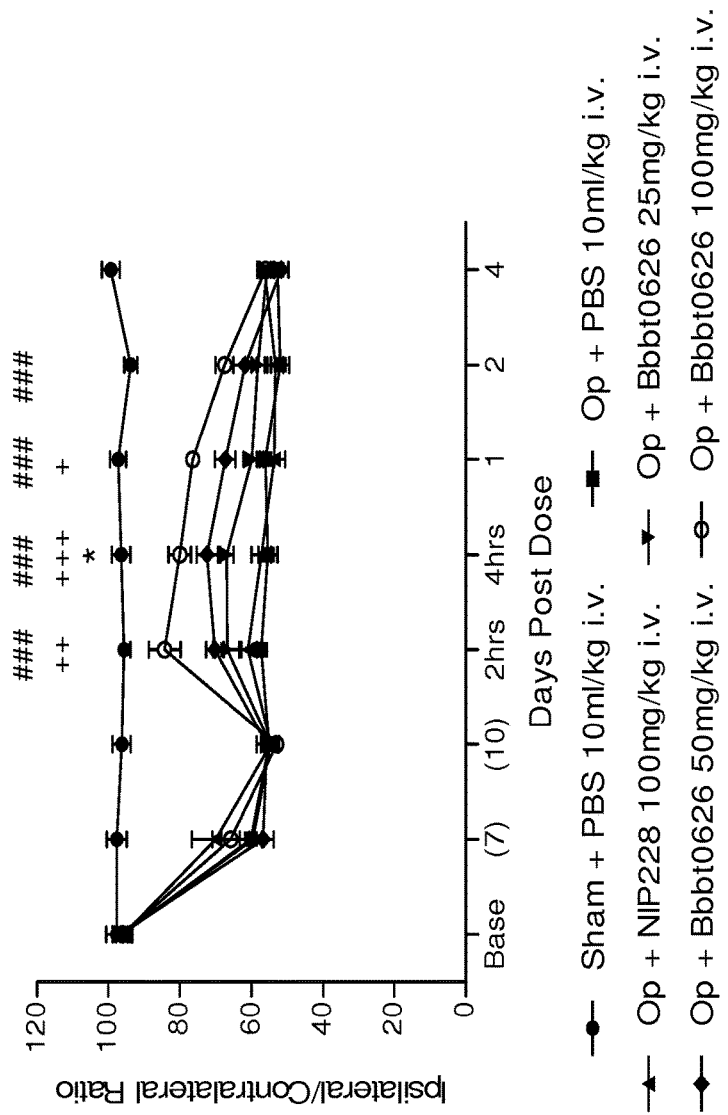

FIG. 10 shows the effect of increased doses of a Bbbt0626-IL1Ra fusion on partial nerve ligation-induced hyperalgesia. n=7-8 per group. Data analyzed using 2-way ANOVA with time and treatment as dependent factors. Subsequent statistical significance obtained using Bonferroni's Post Hoc test. P values are shown.

Figure 11A:
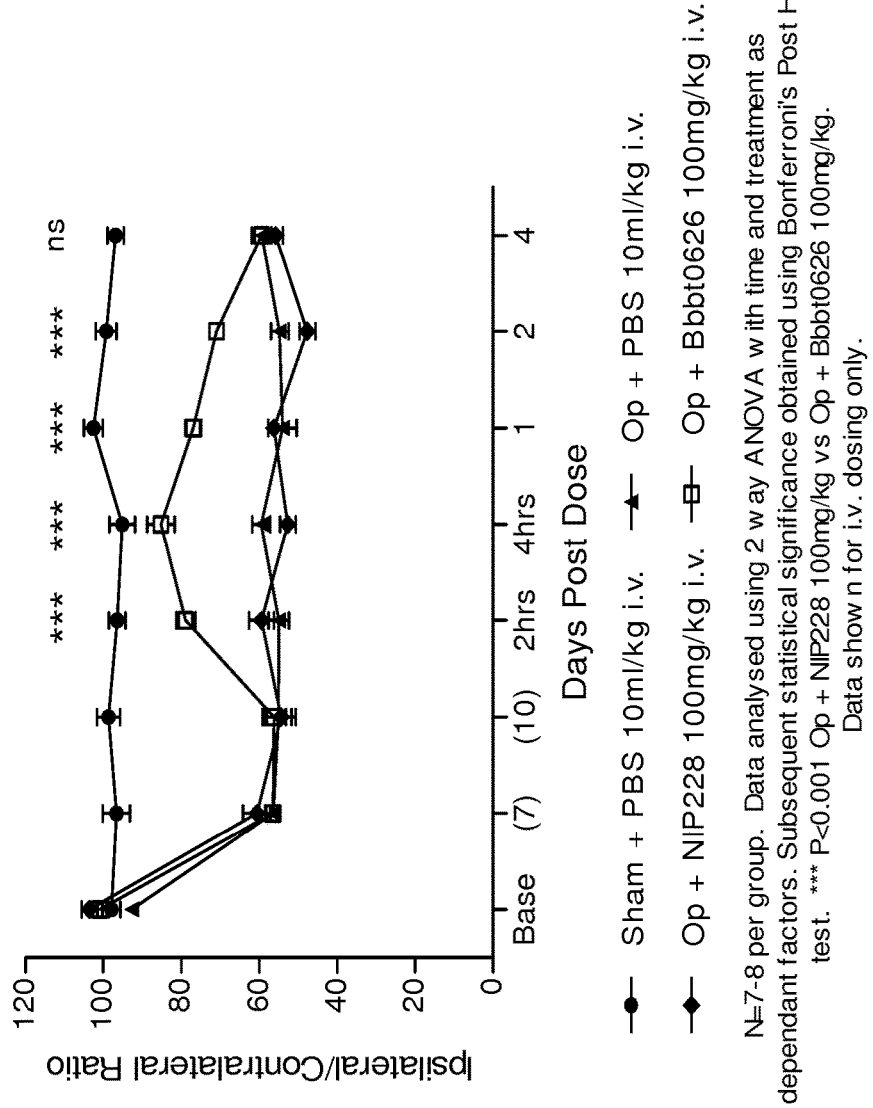
Figure 11B:
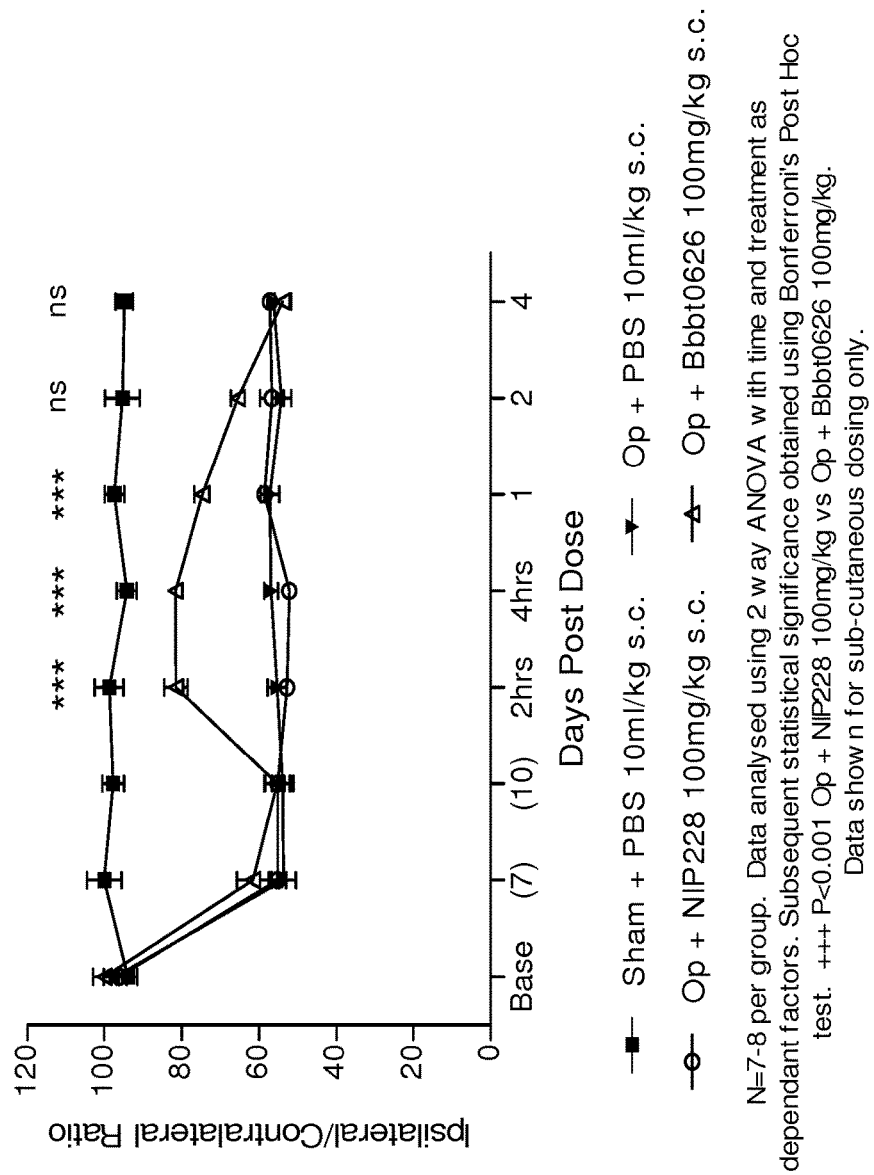

FIGS. 11A and 11B compare the effect of intravenous vs. subcutaneous administration of a Bbbt0626-IL1Ra fusion on partial nerve ligation-induced hyperalgesia. n=7-8 per group. Data analyzed using 2-way ANOVA with time and treatment as dependent factors. Subsequent statistical significance obtained using Bonferroni's Post Hoc test. P values are shown.

Figure 12A:
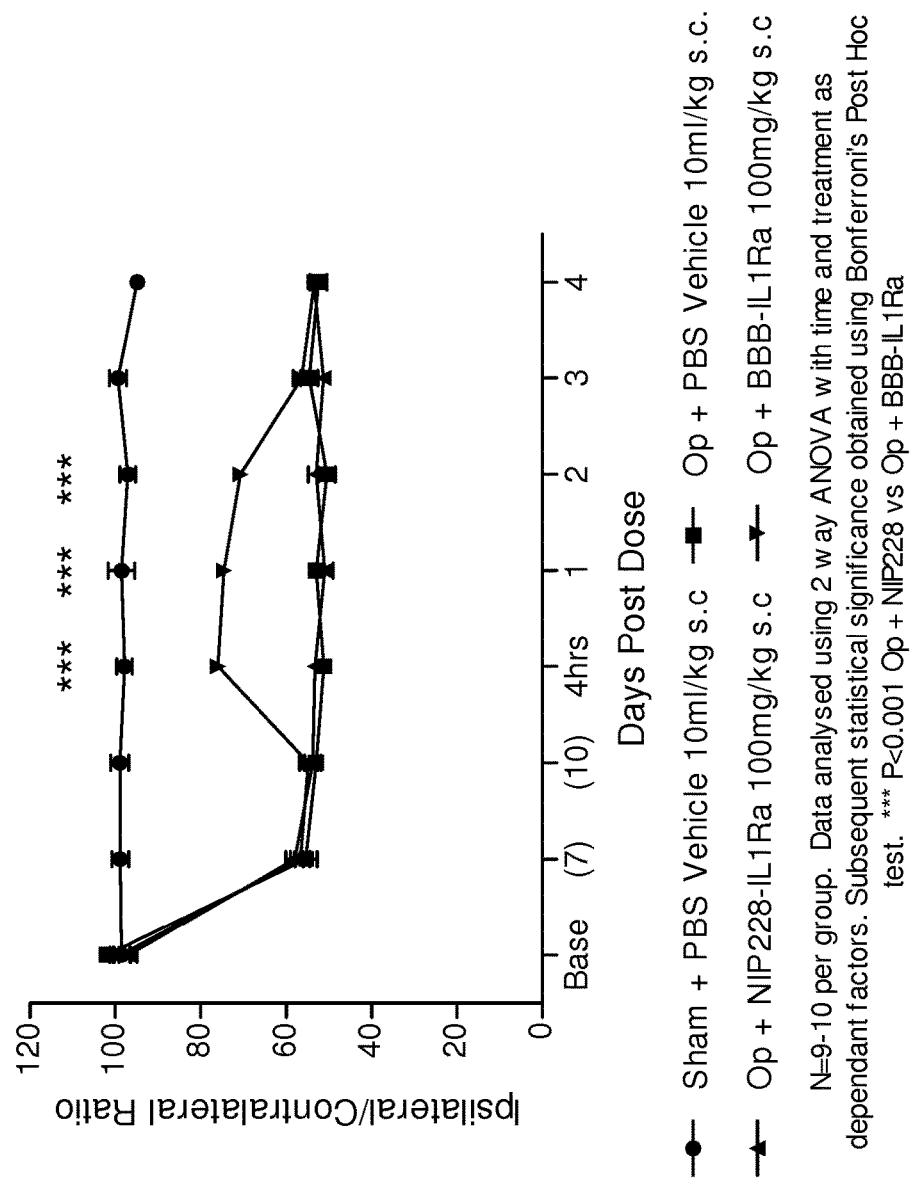
Figure 12B:
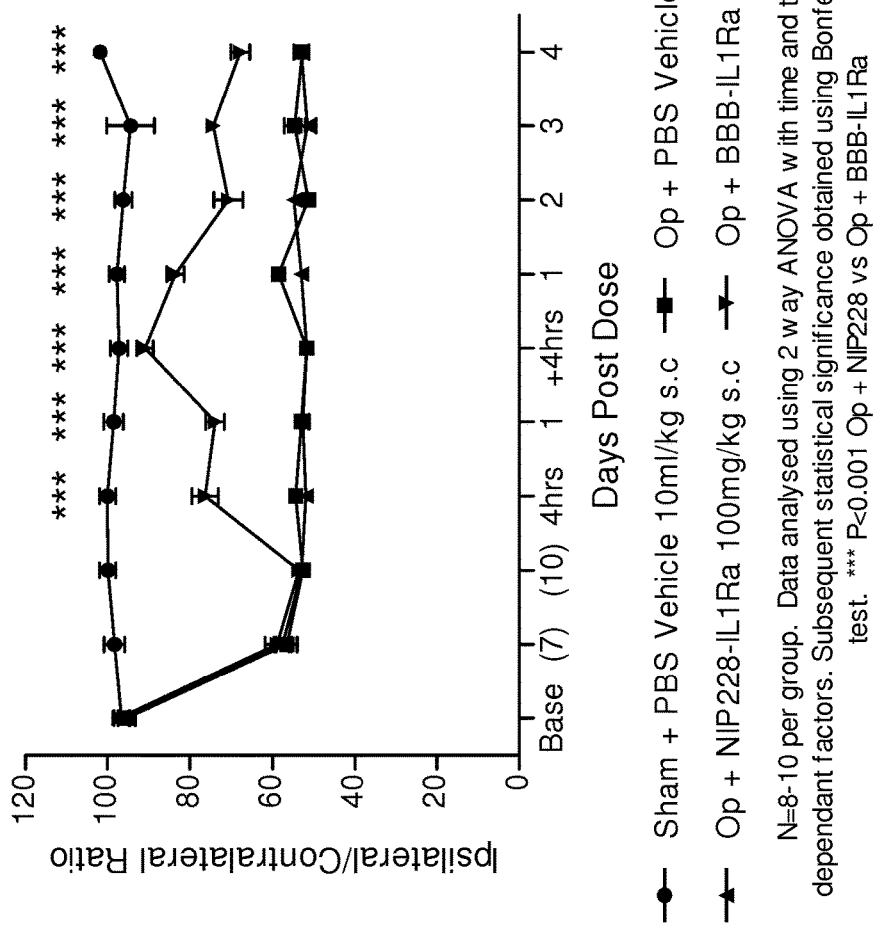

FIGS. 12A and 12B compare single and repeat dosing of a Bbbt0626-IL1Ra fusion on partial nerve ligation-induced hyperalgesia. n=8-10 per group. Data analyzed using 2-way ANOVA with time and treatment as dependent factors. Subsequent statistical significance obtained using Bonferroni's Post Hoc test. P values are shown.

DETAILED DESCRIPTION

Definitions

As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term and/or as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the disclosure, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are also provided.

Amino acids are referred to herein by their commonly known three letter symbols or by the one-letter symbols recommended by the IUPAC-IUB Biochemical Nomenclature Commission. Nucleotides, likewise, are referred to by their commonly accepted single-letter codes.

The terms "antibody" or "immunoglobulin," as used interchangeably herein, include whole antibodies and any antigen binding fragment or single chains thereof.

A typical antibody comprises at least two heavy (H) chains and two light (L) chains interconnected by disulfide bonds. Certain camelid antibodies as described herein comprise two H chains but no L chains. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, Cl. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "germlining" means that amino acids at specific positions in an antibody are mutated back to those in the germ line.

The term "antibody" can refer to an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies or antigen-binding fragments thereof, chimeric antibodies, humanized antibodies, human antibodies, fusion proteins comprising an antigen determination portion of an antibody, and any other modified immunoglobulin molecule comprising an antigen recognition site so long as the antibodies exhibit a particular biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules such as toxins, radioisotopes, etc.

The term "antigen binding fragment" refers to a portion of an intact antibody and refers to the complementarity determining variable regions of an intact antibody. Examples of antibody fragments include, but are not limited to Fab, Fab', F(ab')2, and Fv fragments, linear antibodies, single chain antibodies (e.g., ScFvs), and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have a specificity, an affinity, and/or a capability of interest (Jones et al., 1986, Nature, 321:522-525; Riechmann et al., 1988, Nature, 332:323-327; Verhoeyen et al., 1988, Science, 239:1534-1536). In some instances, the Fv framework region (FW) residues of a human immunoglobulin are replaced with the corresponding residues in an antibody from a non-human species that has a specificity, an affinity, and/or a capability of interest.

Humanized antibodies can be further modified by the substitution of additional residues either in the Fv framework region and/or within the replaced non-human residues to refine and optimize antibody specificity, affinity, and/or capability. In general, humanized antibodies will comprise substantially all of at least one, and typically two or three, variable domains containing all or substantially all of the CDR regions that correspond to the non-human immunoglobulin whereas all or substantially all of the FR regions are those of a human immunoglobulin consensus sequence. Humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

A "variable region" of an antibody refers to the variable region of the antibody light chain or the variable region of the antibody heavy chain, either alone or in combination. The variable regions of the heavy and light chain each consist of four framework regions (FW) connected by three complementarity-determining regions (CDRs) also known as hypervariable regions. The CDRs in each chain are held together in close proximity by the FW regions and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) J. Molec. Biol. 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g, Kabat et al., Sequences of Immunological Interest, 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). See Table 1 below. Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

TABLE 1

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See e.g., Lefranc, M. P. et al., Dev. Comp. Immunol. 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema H-CDR1 is at positions 26 to 35, H-CDR2 is at positions 51 to 57, H-CDR3 is at positions 93 to 102, L-CDR1 is at positions 27 to 32, L-CDR2 is at positions 50 to 52, and L-CDR3 is at positions 89 to 97.

As used throughout the specification the VH CDRs sequences described correspond to the classical Kabat numbering locations, namely Kabat H-CDR1 is at positions 31-35, H-CDR2 is a positions 50-65, and H-CDR3 is at positions 95-102. L-CDR2 and L-CDR3 also correspond to classical Kabat numbering locations, namely positions 50-56 and 89-97, respectively. As used herein, the terms "L-CDR1" or "light chain CDR1" correspond to sequences located at Kabat positions 23-34 in the VL (in contrast, the classical L-CDR1 location according to the Kabat numbering schema corresponds to positions 24-34).

As used herein the term "Fc region" includes the polypeptides comprising the constant region of an antibody excluding the first constant region immunoglobulin domain (e.g., CH1), and fragments thereof. Thus Fc refers to the last two constant domains of IgA, IgD, and IgG, and the last three constant domains of IgE and IgM, and optionally the flexible hinge region N-terminal to these domains. For IgA and IgM the Fc region can include the J chain. For IgG, Fc comprises immunoglobulin domains Cgamma2 and Cgamma3 (Cγ2 and Cγ3) and optionally the hinge region between Cgamma1 (Cγ1) and Cgamma2 (Cγ2).

Although the boundaries of the Fc region can vary, the human IgG heavy chain Fc region is usually defined to comprise residues C226 or P230 to its carboxyl-terminus, wherein the numbering is according to the EU index as set forth in Kabat (Kabat et al., Sequences of Proteins of Immunological Interest, 5th Ed. Public Health Service, National Institutes of Health, Bethesda, Md. (1991)). Fc can refer to this region in isolation, or this region in the context of an antibody, antibody fragment, or Fc fusion protein.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211). It is contemplated that the antibodies of the present disclosure can incorporate any allotype, isoallotype, or haplotype of any immunoglobulin gene, and are thus not limited to the allotype, isoallotype or haplotype of the sequences provided herein.

As used herein, the term "Fc fusion protein" encompasses proteins (e.g., conjugate compounds of the present disclosure) comprising a full length Fc domain as well as proteins comprising Fc domain fragments (e.g., a full CH2 domain, a full CH3 domain, a CH2 fragment, a CH3 fragment, or combinations thereof). An Fc fusion protein can also comprise all or a portion of the hinge region.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc) with a specificity, an affinity, and/or a capability of interest while the constant regions are homologous to the sequences in antibodies derived from another (usually human) to avoid eliciting an immune response in that species.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

"Potency" is normally expressed as an $IC_{50}$ value, in nM or pM unless otherwise stated. $IC_{50}$ is the median inhibitory concentration of an antibody molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by any number of means known in the art.

The fold improvement in potency for the antibodies or polypeptides of the disclosure as compared to a reference antibody can be at least about 2-fold, at least about 4-fold, at least about 6-fold, at least about 8-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

A polypeptide, antibody, polynucleotide, vector, cell, or composition that is "isolated" is a polypeptide, antibody, polynucleotide, vector, cell, or composition that is in a form not found in nature. Isolated polypeptides, antibodies, polynucleotides, vectors, cells or compositions include those which have been purified to a degree that they are no longer in a form in which they are found in nature. In some embodiments, an antibody, polynucleotide, vector, cell, or composition that is isolated is substantially pure.

By "subject" or "individual" or "animal" or "patient" or "mammal," is meant any subject, particularly a mammalian subject, for whom diagnosis, prognosis, or therapy is indicated. Mammalian subjects include humans, domestic animals, farm animals, sports animals, and zoo animals including, e.g., humans, non-human primates, dogs, cats, guinea pigs, rabbits, rats, mice, horses, cattle, bears, and so on.

The term "pharmaceutical composition" refers to a preparation which is in such form as to permit the biological activity of the active ingredient to be effective, and which contains no additional components which are unacceptably toxic to a subject to which the composition would be administered. Such composition can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" or "prevent" a disease or disorder in a subject or mammal.

The word "label" when used herein refers to a detectable compound or composition that is conjugated directly or indirectly to the antibody so as to generate a "labeled" antibody. The label can be detectable by itself (e.g., radioisotope labels or fluorescent labels) or, in the case of an enzymatic label, can catalyze chemical alteration of a substrate compound or composition that is detectable.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for an inflammatory or autoimmune disease or disorder according to the methods provided herein if the patient shows, e.g., total, partial, or transient alleviation or elimination of symptoms associated with the disease or disorder.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "expression" as used herein refers to a process by which a gene produces a biochemical, for example, transporter molecule provided herein. The process includes any manifestation of the functional presence of the gene within the cell including, without limitation, gene knockdown as well as both transient expression and stable expression. It includes without limitation transcription of the gene into one or more mRNAs, and the translation of such mRNAs into one or more polypeptides. If the final product is a biochemical, expression includes the creation of that biochemical and any precursors.

An "expression product" can be either a nucleic acid, e.g., a messenger RNA produced by transcription of a gene, or a polypeptide. Expression products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "vector" or "expression vector" is used herein to mean vectors used as a vehicle for introducing into and expressing an expression product of interest in a host cell. As known to those skilled in the art, such vectors can easily be selected from the group consisting of plasmids, phages, viruses and retroviruses. In general, vectors can comprise a selection marker, appropriate restriction sites to facilitate cloning of a particular nucleic acid and the ability to enter and/or replicate in eukaryotic or prokaryotic cells. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "host cell" refers to a cell that harbors a vector constructed using recombinant DNA techniques and encoding at least one expression product. In descriptions of processes for the isolation of an expression product from recombinant hosts, the terms "cell" and "cell culture" are used interchangeably to denote the source of the expression product unless it is clearly specified otherwise, i.e., recovery of the expression product from the "cells" means either recovery from spun down whole cells, or recovery from the cell culture containing both the medium and the suspended cells.

The terms "polypeptide," "peptide," and "protein" are used interchangeably herein to refer to polymers of amino acids of any length. The polymer can be linear or branched, it can comprise modified amino acids, and non-amino acids can interrupt it. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

One such non-limiting example of a sequence alignment algorithm is the algorithm described in Karlin et al., 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)) can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with a residue table, a gap length penalty of 12 and a gap penalty of 4. One skilled in the art can determine appropriate parameters for maximal alignment by particular alignment software. In certain embodiments, the default parameters of the alignment software are used.

In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the disclosure do not abrogate the binding of the polypeptide or antibody containing the amino acid sequence, to the antigen(s), i.e., the IL-21 to which the polypeptide or antibody binds. Methods of identifying nucleotide and amino acid conservative substitutions which do not eliminate antigen binding are well-known in the art (see, e.g., Brummell et al., *Biochem.* 32: 1180-1 187 (1993); Kobayashi et al., *Protein Eng.* 12(10):879-884 (1999); and Burks et al., *Proc. Natl. Acad. Sci. USA* 94:412-417 (1997)).

The term "consensus sequence," as used herein with respect to light chain (VL) and heavy chain (VH) variable regions, refers to a composite or genericized VL or VH sequence defined based on information as to which amino acid residues within the VL or VH chain are amenable to modification without detriment to antigen binding. Thus, in a "consensus sequence" for a VL or VH chain, certain amino acid positions are occupied by one of multiple possible amino acid residues at that position. For example, if an arginine (R) or a serine (S) occur at a particular position, then that particular position within the consensus sequence can be either arginine or serine (R or S). Consensus sequences for VH and VL chain can be defined, for example, by in vitro affinity maturation (e.g., randomizing every amino acid position in a certain CDR using degenerate coding primers), by scanning mutagenesis (e.g., alanine scanning mutagenesis) of amino acid residues within the antibody CDRs, or any other methods known in the art, followed by evaluation of the binding of the mutants to the antigen to determine whether the mutated amino acid position affects antigen binding. In some embodiments, mutations are introduced in the CDR regions. In other embodiments, mutations are introduced in framework regions. In some other embodiments, mutations are introduced in CDR and framework regions.

Blood Brain Barrier Transporter Molecules

This disclosure provides compositions for delivery of a substance of interest, e.g., a therapeutic or diagnostic agent or "payload" across the blood-brain barrier (BBB) using a transporter molecule that can cross brain endothelial cells while associated with the payload, e.g., while fused or conjugated to the payload. As used herein, the term "payload" is used as shorthand for any substance whose transport across the BBB can be facilitated by a transporter molecule as provided herein. A payload can be part of a transporter molecule, e.g., as a fusion polypeptide, or joined to the polypeptide through disulfide bonds or other covalent bonds. Alternatively the payload can be associated with the transporter molecule in any way that will allow the transporter molecule to facilitate its transport across the BBB, as further described below. In certain aspects the payload remains part of the transporter molecule following BBB transport, and retains central nervous system (CNS) activity in that form. Alternatively the payload can be associated with the transporter molecule during BBB transport, but in a way that allows it to disassociate with the transporter molecule following BBB transport. Exemplary, non-limiting examples of payload moieties are provided elsewhere herein. The disclosure further provides methods for the treatment or diagnosis of a disease or disorder of the CNS, comprising the use of such transporter molecules.

In certain aspects, this disclosure provides an isolated transporter molecule comprising an immunoglobulin-derived polypeptide. In certain aspects the polypeptide is a humanized version of the camelid antibody FC5, identified and isolated using Fluorescence Micro-volume Assay Technology (FMAT) to detect binding to brain microvascular endothelial cells (BMVEC), e.g., mouse B.End3 cells. In certain aspects the polypeptide comprises an antibody VH and an antibody VL isolated from a naïve scFv phage library, or a scFv phage library comprising two heavy chain complementarity determining regions (CDRs) from FC5, again identified and isolated using FMAT to detect binding to BMVEC. In certain aspects, the immunoglobulin-derived polypeptide is an antibody or an active fragment thereof, where "active" means that the transporter molecule can, e.g., bind to BMVEC in one or more species, e.g., mouse BMVEC, rat BMVEC, cynomolgus monkey BMVEC, or human BMVEC, internalize into BMVEC of one or more species, and/or cross the blood brain barrier either alone, or associated with a payload. In certain aspects, the transporter molecule comprises one or more of Bbbt0241, Bbbt0351, Bbbt0626, Bbbt0632, Bbbt0654, Bbbt0726, Bbbt0727, Bbbt0732, Bbbt0754, Bbbt0674, Bbbt0755, Bbbt0643, Bbbt0579 or Bbbt0671.

In certain aspects, the transporter molecule does not bind to BMVEC but is still capable of transporting across the BBB as indicated in the in vitro transcytosis assay. In certain aspects this transporter molecule crosses the BBB with greater efficiency than FC5. In certain aspects this transporter molecule is identical to the FC5 amino acid sequence except for two amino acid substitutions, a T97A substitution at Kabat position 97, and a T100aD substitution at Kabat position 100a, and has the amino acid sequence of Bbbt0351 (SEQ ID NO: 200).

In certain aspects, the immunoglobulin-derived polypeptide comprises immunoglobulin heavy chain complementarity determining regions (CDRs). For example the immunoglobulin-derived polypeptide can include an immunoglobulin heavy chain complementarity-determining region-1 (H-CDR1), an immunoglobulin heavy chain complementarity-determining region-2 (H-CDR2), an immunoglobulin heavy chain complementarity-determining region-3 (H-CDR3). In certain aspects, the immunoglobulin-derived polypeptide can further comprise, or alternatively comprise, immunoglobulin light chain CDRs. For example, the immunoglobulin-derived polypeptide can include an complementarity-determining region-1 (L-CDR1), an immunoglobulin light chain complementarity-determining region-2 (L-CDR2), and an immunoglobulin light chain complementarity-determining region-3 (L-CDR3). In certain aspects, the immunoglobulin-derived polypeptide can contain an H-CDR1, an H-CDR2, an H-CDR3, an L-CDR1, an L-CDR2, and an L-CDR3 with the following amino acid sequences, respectively:
- (a) SEQ ID NO: 3, SEQ ID NO: 4, SEQ ID NO: 5, SEQ ID NO: 12, SEQ ID NO: 13, and SEQ ID NO: 14, the CDRs of Bbbt0241;
- (b) SEQ ID NO: 21, SEQ ID NO: 22, SEQ ID NO: 23, Q G D S L $X_2$ $X_3$ Y Y $X_4$ $X_5$, where $X_2$=T or R; $X_3$, S, R, or T; $X_4$=A or T; and $X_5$=N or S (SEQ ID NO: 229), G $X_8$ $X_9$ N R P s, where $X_8$=K or E and $X_9$=N or D (SEQ ID NO: 230), and N S R D $X_{13}$ $X_{14}$ G $X_{15}$ $X_{16}$ $X_{17}$ V, where $X_{13}$=S or N; $X_{14}$=S or T; $X_{15}$=N, K, or H; $X_{16}$=H or P; and $X_{17}$=V or W, (SEQ ID NO: 231), CDRs similar to those of Bbbt0626;
- (c) SEQ ID NO: 39, SEQ ID NO: 40, SEQ ID NO: 41, SEQ ID NO: 229, SEQ ID NO: 230, and SEQ ID NO: 231, CDRs similar to those of Bbbt0632;
- (d) SEQ ID NO: 57, SEQ ID NO: 58, SEQ ID NO: 59, SEQ ID NO: 66, SEQ ID NO: 67, and SEQ ID NO: 68, the CDRs of Bbbt0654;
- (e) SEQ ID NO: 75, SEQ ID NO: 76, SEQ ID NO: 77, SEQ ID NO: 229, SEQ ID NO: 230, and SEQ ID NO: 231, CDRs similar to those of Bbbt0726;
- (f) SEQ ID NO: 93, SEQ ID NO: 94, SEQ ID NO: 95, SEQ ID NO: 229, SEQ ID NO: 230, and SEQ ID NO: 231, CDRs similar to those of Bbbt0727;
- (g) SEQ ID NO: 111, SEQ ID NO: 112, SEQ ID NO: 113, SEQ ID NO: 229, SEQ ID NO: 230, and SEQ ID NO: 231, CDRs similar to those of Bbbt0732;
- (h) SEQ ID NO: 129, SEQ ID NO: 130, SEQ ID NO: 131, SEQ ID NO: 138, SEQ ID NO: 139, and SEQ ID NO: 140, the CDRs of Bbbt0754;
- (i) SEQ ID NO: 147, SEQ ID NO: 148, SEQ ID NO: 149, SEQ ID NO: 156, SEQ ID NO: 157, and SEQ ID NO: 158, the CDRs of Bbbt0674;
- (j) SEQ ID NO: 165, SEQ ID NO: 166, SEQ ID NO: 167, SEQ ID NO: 174, SEQ ID NO: 175, and SEQ ID NO: 176, the CDRs of Bbbt0755;
- (k) SEQ ID NO: 183, SEQ ID NO: 184, SEQ ID NO: 185, SEQ ID NO: 192, SEQ ID NO: 193, and SEQ ID NO: 194, the CDRs of Bbbt0643; or
- (l) SEQ ID NO: 210, SEQ ID NO: 211, SEQ ID NO: 212, SEQ ID NO: 219, SEQ ID NO: 220, SEQ ID NO: 221, the CDRs of Bbbt0579.

In certain alternative embodiments, one or more CDRs as described above are identical to the recited CDRs, except for, e.g., 1, 2, 3, 4, or 5 single amino acid deletions, substitutions, or insertions. In certain embodiments, the transporter molecule as provided above can cross the blood brain barrier. In certain aspects, the H-CDR3 of the Bbbt0241 variant Bbbt0241m comprises two substitutions, a T97A substitution at Kabat position 97, and a T100aD substitution at Kabat position 100a.

In certain aspects, the immunoglobulin-derived polypeptide can contain an H-CDR1, an H-CDR2, an H-CDR3, an L-CDR1, an L-CDR2, and an L-CDR3 with the following amino acid sequences, respectively:
- (b) SEQ ID NO: 21, SEQ ID NO: 22, SEQ ID NO: 23, SEQ ID NO: 30, SEQ ID NO: 31, and SEQ ID NO: 32, the CDRs of Bbbt0626;
- (c) SEQ ID NO: 39, SEQ ID NO: 40, SEQ ID NO: 41, SEQ ID NO: 48, SEQ ID NO: 49, and SEQ ID NO: 50, the CDRs of Bbbt0632;
- (e) SEQ ID NO: 75, SEQ ID NO: 76, SEQ ID NO: 77, SEQ ID NO: 84, SEQ ID NO: 85, and SEQ ID NO: 86, the CDRs of Bbbt0726;
- (f) SEQ ID NO: 93, SEQ ID NO: 94, SEQ ID NO: 95, SEQ ID NO: 102, SEQ ID NO: 103, and SEQ ID NO: 104, the CDRs of Bbbt0727; or
- (g) SEQ ID NO: 111, SEQ ID NO: 112, SEQ ID NO: 113, SEQ ID NO: 120, SEQ ID NO: 121, and SEQ ID NO: 122, the CDRs of Bbbt0732.

In certain alternative embodiments, one or more CDRs as described above are identical to the recited CDRs, except for, e.g., 1, 2, 3, 4, or 5 single amino acid deletions, substitutions, or insertions. In certain embodiments, the transporter molecule as provided above can cross the blood brain barrier.

In certain aspects, the H-CDR1, the H-CDR2, the H-CDR3, the L-CDR1, the L-CDR2, and the L-CDR3 can be situated in immunoglobulin framework regions to produce an antibody VH and an antibody VL. In certain aspects the framework regions can be human-derived framework regions. In certain aspects the antibody VH and antibody VL are fused together, e.g., through a flexible peptide linker, to form a scFv molecule. In certain aspects the VH and VL further comprise one or more immunoglobulin constant domains, e.g., a CH1 domain, a hinge region, a CH3 domain, a CH3 domain, a CL-kappa domain, and/or a CL lambda domain. In certain aspects the one or more immunoglobulin constant domains are derived from a human immunoglobulin, e.g., a human IgG1 immunoglobulin. In certain aspects the VH, VL, and/or constant domains can comprise mutations to facilitate, e.g., longer or shorter half-life, increased or reduced effector functions, or the ability to attach a payload molecule either via peptide fusion, a disulfide bond, or chemical conjugation.

In certain aspects, this disclosure provides an isolated transporter molecule comprising an immunoglobulin-derived polypeptide, where the polypeptide comprises an immunoglobulin heavy chain variable region (VH) region, an immunoglobulin light chain variable region (VL) region or an immunoglobulin VH region and an immunoglobulin VL region. In certain aspects the immunoglobulin-derived polypeptide comprises:

(a) an VH amino acid sequence at least 80%, 84%, 85%, 90%, 95%, 96%, 97%, 98%, or 99% identical to SEQ ID NO: 2 and a VL amino acid sequence at least 80%, 84%, 85%, 90%, 95%, 96%, 97%, 98%, or 99% identical to SEQ ID NO: 11, where SEQ ID NO: 2 and SEQ ID NO: 11 encode the VH and VL regions of Bbbt0241;

(b) a VH amino acid sequence at least 80%, 84%, 85%, 90%, 95%, 96%, 97%, 98%, or 99% identical to SEQ ID NO: 20 and a VL amino acid sequence at least 80%, 84%, 85%, 90%, 95%, 96%, 97%, 98%, or 99% identical to SEQ ID NO: 29, where SEQ ID NO: 20 and SEQ ID NO: 29 encode the VH and VL regions of Bbbt0626;

(c) a VH amino acid sequence at least 80%, 84%, 85%, 90%, 95%, 96%, 97%, 98%, or 99% identical to SEQ ID NO: 38 and a VL amino acid sequence at least 80%, 84%, 85%, 90%, 95%, 96%, 97%, 98%, or 99% identical to SEQ ID NO: 47, where SEQ ID NO: 38 and SEQ ID NO: 47 encode the VH and VL regions of Bbbt0632;

(d) a VH amino acid sequence at least 80%, 84%, 85%, 90%, 95%, 96%, 97%, 98%, or 99% identical to SEQ ID NO: 56 and a VL amino acid sequence at least 80%, 84%, 85%, 90%, 95%, 96%, 97%, 98%, or 99% identical to SEQ ID NO: 65, where SEQ ID NO: 56 and SEQ ID NO: 65 encode the VH and VL regions of Bbbt0654;

(e) a VH amino acid sequence at least 80%, 84%, 85%, 90%, 95%, 96%, 97%, 98%, or 99% identical to SEQ ID NO: 74 and a VL amino acid sequence at least 80%, 84%, 85%, 90%, 95%, 96%, 97%, 98%, or 99% identical to SEQ ID NO: 83, where SEQ ID NO: 74 and SEQ ID NO: 83 encode the VH and VL regions of Bbbt0726;

(f) a VH amino acid sequence at least 80%, 84%, 85%, 90%, 95%, 96%, 97%, 98%, or 99% identical to SEQ ID NO: 92 and a VL amino acid sequence at least 80%, 84%, 85%, 90%, 95%, 96%, 97%, 98%, or 99% identical to SEQ ID NO: 101, where SEQ ID NO: 92 and SEQ ID NO: 101 encode the VH and VL regions of Bbbt0727;

(g) a VH amino acid sequence at least 80%, 84%, 85%, 90%, 95%, 96%, 97%, 98%, or 99% identical to SEQ ID NO: 110 and a VL amino acid sequence at least 80%, 84%, 85%, 90%, 95%, 96%, 97%, 98%, or 99% identical to SEQ ID NO: 119, where SEQ ID NO: 110 and SEQ ID NO: 119 encode the VH and VL regions of Bbbt0732;

(h) a VH amino acid sequence at least 80%, 84%, 85%, 90%, 95%, 96%, 97%, 98%, or 99% identical to SEQ ID NO: 128 and a VL amino acid sequence at least 80%, 84%, 85%, 90%, 95%, 96%, 97%, 98%, or 99% identical to SEQ ID NO: 137, where SEQ ID NO: 128 and SEQ ID NO: 137 encode the VH and VL regions of Bbbt0754;

(i) a VH amino acid sequence at least 80%, 84%, 85%, 90%, 95%, 96%, 97%, 98%, or 99% identical to SEQ ID NO: 146 and a VL amino acid sequence at least 80%, 84%, 85%, 90%, 95%, 96%, 97%, 98%, or 99% identical to SEQ ID NO: 155, where SEQ ID NO: 146 and SEQ ID NO: 155 encode the VH and VL regions of Bbbt0674;

(j) a VH amino acid sequence at least 80%, 84%, 85%, 90%, 95%, 96%, 97%, 98%, or 99% identical to SEQ ID NO: 164 and a VL amino acid sequence at least 80%, 84%, 85%, 90%, 95%, 96%, 97%, 98%, or 99% identical to SEQ ID NO: 173, where SEQ ID NO: 164 and SEQ ID NO: 173 encode the VH and VL regions of Bbbt0755;

(k) a VH amino acid sequence at least 80%, 84%, 85%, 90%, 95%, 96%, 97%, 98%, or 99% identical to SEQ ID NO: 182 and a VL amino acid sequence at least 80%, 84%, 85%, 90%, 95%, 96%, 97%, 98%, or 99% identical to SEQ ID NO: 191, where SEQ ID NO: 182 and SEQ ID NO: 191 encode the VH and VL regions of Bbbt0643;

(l) an VH amino acid sequence at least 80%, 84%, 85%, 90%, 95%, 96%, 97%, 98%, or 99% identical to SEQ ID NO: 209 and a VL amino acid sequence at least 80%, 84%, 85%, 90%, 95%, 96%, 97%, 98%, or 99% identical to SEQ ID NO: 218, where SEQ ID NO: 209 and SEQ ID NO: 218 encode the VH and VL regions of Bbbt0579; or (m) an VH amino acid sequence at least 80%, 84%, 85%, 90%, 95%, 96%, 97%, 98%, or 99% identical to SEQ ID NO: 226 and a VL amino acid sequence at least 80%, 84%, 85%, 90%, 95%, 96%, 97%, 98%, or 99% identical to SEQ ID NO: 227, where SEQ ID NO: 226 and SEQ ID NO: 227 encode the VH and VL regions of Bbbt0671;

In certain aspects, the transporter molecule provided above has transporter activity, e.g., it can bind to BMVEC from one or more species, e.g., mouse, rat, cynomolgus monkey, or human BMVEC, it can internalize into BMVEC of one or more species, or it can cross the blood brain barrier.

In certain aspects, this disclosure provides an isolated transporter molecule comprising an immunoglobulin-derived polypeptide, where the polypeptide comprises a VH region and a VL region, where:

(a) the VH comprises SEQ ID NO: 2 and the VL comprises SEQ ID NO: 11;

(b) the VH comprises SEQ ID NO: 20 and the VL comprises S S E L T Q D P A V S V A L $X_1$ Q T V R I T C Q G D S L $X_2$ $X_3$ Y Y $X_4$ $X_5$ W Y Q $X_6$ K P G Q A P V L V $X_7$ Y G $X_8$ $X_9$ N R P S G $X_{10}$ P D R F S G S $X_{11}$ S G $X_{12}$ T A S L T I T G A Q A E D E A D Y Y C N S R D $X_{13}$ $X_{14}$ G $X_{15}$ $X_{16}$ $X_{17}$ V F G G G T K L T V L; where $X_1$=R or G; $X_2$=T or R; $X_3$=S, R, or T; $X_4$=A or T; $X_5$=N or S; $X_6$=H or Q; $X_7$=M or I; $X_8$=K or E; $X_9$=N or D; $X_{10}$=V or I; $X_{11}$=S or R; $X_{12}$=N or T; $X_{13}$=S or N; $X_{14}$=S or T; $X_{15}$=N, K, or H; $X_{16}$=H or P; and $X_{17}$=V or W (SEQ ID NO: 228) or SEQ ID NO: 29;

(c) the VH comprises SEQ ID NO: 38 and the VL comprises SEQ ID NO: 228 or SEQ ID NO: 47;

(d) the VH comprises SEQ ID NO: 56 and the VL comprises SEQ ID NO: 65;

(e) the VH comprises SEQ ID NO: 74 and the VL comprises SEQ ID NO: 228 or SEQ ID NO: 83;

(f) the VH comprises SEQ ID NO: 92 and the VL comprises SEQ ID NO: 228 or SEQ ID NO: 101;

(g) the VH comprises SEQ ID NO: 110 and the VL comprises SEQ ID NO: 228 or SEQ ID NO: 119;

(h) the VH comprises SEQ ID NO: 128 and the VL comprises SEQ ID NO: 137;

(i) the VH comprises SEQ ID NO: 146 and the VL comprises SEQ ID NO: 155;

(j) the VH comprises SEQ ID NO: 164 and the VL comprises SEQ ID NO: 173; or (k) the VH comprises SEQ ID NO: 182 and the VL comprises SEQ ID NO: 191.

In certain aspects, the transporter molecule provided above has transporter activity, e.g., it can bind to BMVEC from one or more species, e.g., mouse, rat, cynomolgus monkey, or human BMVEC, it can internalize into BMVEC of one or more species, or it can cross the blood brain barrier.

In certain aspects, a transporter molecule as provided herein comprises an immunoglobulin-derived polypeptide, where the immunoglobulin-derived polypeptide comprises an antibody or a BBB-penetrable fragment thereof. A "BBB-penetrable fragment" as described herein is a fragment of the transporter molecule that can specifically bind to BMVEC of one or more species and cross through BMVEC in vitro or in vivo from the peripheral vasculature into the CNS vasculature. Whether a given fragment is a BBB-penetrable fragment can be tested by a variety of in vitro or in vivo assays known to persons of ordinary skill in the art. For example, the transporter molecule can be tested in the in vitro transcytosis assay described elsewhere herein, or in an in vivo assay such as the diuresis assay described elsewhere herein. Other assays that could be used to measure in vivo delivery of payloads across the BBB include, without limitation, chronic constriction injury (CCI); spared nerve injury model (SNI) or spinal nerve ligation (SNL), all of which can be measured via paw flick, or the Hargreaves method (Hargreaves K, et al., Pain; 1988; 32; 77-88).

In certain aspects, a transporter molecule as provided herein comprises an antibody or BBB-penetrable fragment thereof that comprises or consists of two or more subunits, e.g., a heavy chain or fragment thereof and a light chain or fragment thereof, where the heavy chain and light chain are associated, e.g., as a single fusion protein (e.g., a scFv), or as two subunits held together by one or more disulfide bonds. In certain aspects the heavy chain comprises a VH domain or region and the light chain comprises a VL domain or region.

In certain aspects the heavy chain further comprises a heavy chain constant domain, e.g., a CH1 domain, a hinge, a CH2 domain, and/or a CH3 domain, or fragment thereof. In certain aspects the heavy chain constant domain is an IgG constant domain or fragment thereof, e.g., a human IgG constant domain, e.g., a human IgG1, IgG2, IgG3 or IgG4 constant domain. In certain aspects, the IgG constant domain or fragment thereof comprises an altered glycosylation and/or one or more amino acid substitutions relative to a wild-type IgG constant domain wherein the modified IgG has a particular property, e.g., an increased or decreased half-life compared to the half-life of an IgG having the wild-type IgG constant domain, either increased or decreased effector functions relative to a wild-type IgG constant domain, or the ability to attach heterologous moieties via, e.g., a peptide bond, a disulfide bond, or a chemical conjugation. In certain aspects, the IgG constant domain or fragment thereof has an altered glycosylation relative to a wild-type IgG constant domain wherein the modified IgG has a particular property, e.g., an increased or decreased half-life compared to the half-life of an IgG having the wild-type IgG constant domain, either increased or decreased effector functions relative to a wild-type IgG constant domain.

Various effector functions can be facilitated by immunoglobulin constant domains including without limitation antibody-dependent cell-mediated cytotoxicity (ADCC), complement-dependent cytotoxicity (CDC), or antibody-dependent cellular phagocytosis (ADCP).

Numerous specific IgG constant domain substitutions capable of increasing or decrease half-life are known in the art. For example, the substitutions 252Y, 254T, 256E, and combinations thereof, as numbered by the EU index as set forth in Kabat have been shown to increase half-life (see, e.g., U.S. Pat. No. 7,083,784). Substitutions at residues 250, 252, 254, 256, 257, 309, 311, 428, 433, 434 and combinations thereof have also been reported to alter half-life (see, e.g., U.S. Pat. Nos. 6,277,375, 7,083,784; 7,217,797, 8,088, 376; US2002/0147311; US2007/0148164; WO9823289 and WO09058492). Similarly, IgG constant domain substitutions capable of increasing or decreasing effector functions have been described in the art. For example, the substitutions 239S and/or 332E, as numbered by the EU index as set forth in Kabat have been shown to increase ADCC activity (see, e.g., WO2004099249, U.S. Pat. No. 7,317,091), while the substitutions 234F, 235E, 235F, 235Q, 235Y, 239A, 332Q, 331S, 332Q and combinations thereof, as numbered by the EU index as set forth in Kabat have been shown to decrease ADCC. Numerous other substitutions which alter effector function (increase or decrease) can be used, for example, see the mutations described in WO8807089, WO9958572, WO9951642, WO2012175751, WO2011149999, WO2011066501, WO2000042072, WO2011120134.

Effector functions (e.g., ADCC) elicited by molecules comprising IgG constant domains or fragments thereof strongly depend on the carbohydrate moiety linked to the CH2 region of the IgG constant domain (Claudia Ferrara et al., 2006, Biotechnology and Bioengineering 93:851-861). Thus, glycosylation of the CH2 domain of the IgG constant can be modified to increase or decrease effector function (see for example, Umana et al, 1999, Nat. Biotechnol 17:176-180; Davies et al., 2001, Biotechnol Bioeng 74:288-294; Shields et al, 2002, J Biol Chem 277:26733-26740; Shinkawa et al., 2003, J Biol Chem 278:3466-3473; U.S. Pat. Nos. 6,602,684; 6,946,292; 7,064,191; 7,214,775; 7,393,683; 7,425,446; 7,504,256; U.S. Publication. Nos. 2003/0157108; 2003/0003097; 2009/0010921; POTILLE-GENT™ technology (Biowa, Inc); GLYCOMAB™ glycosylation engineering technology (Roche)). In particular, IgG constant regions having reduced fucosylation have increased binding to FcγRIIIA and enhanced ADCC activity. Methods for generating IgG constant regions have reduced or no fucosylation have been described (see, e.g., US2005/0226867; Mori et al., 2004, Biotechnol Bioeng 88:901-908; Cox et al., 2006, Nat Biotechnol., 24:1591-7, and references provided supra). Alternatively, IgG constant regions lacking glycosylation have been shown to have reduced effector function (Walker et al., 1989, Biochem. J. 259:347-353) and can be generated, for example using bacterial host cells (see, e.g., Simmons et al. 2002, J. Immunol. Methods, 263:133-147).

In certain aspects, a transporter molecule as provided herein comprises an IgG constant domain or fragment thereof comprising an altered glycosylation and/or one or more amino acid substitutions relative to a wild-type IgG constant domain wherein at least one effector function (e.g., ADCC) of the transporter molecule is reduced or eliminated. In a specific aspect ADCC activity, CDC activity, or both ADCC and CDC activity are reduced or eliminated.

In certain aspects the light chain further comprise a light chain constant domain or fragment thereof, e.g., a Ckappa domain or a Clambda domain, e.g., a human kappa constant domain or fragment thereof, or a human lambda constant region or fragment thereof.

In certain aspects, a transporter molecule as provided herein comprises an antibody or BBB-penetrable fragment thereof that comprises or consists of a murine antibody, a humanized antibody, a chimeric antibody, a monoclonal antibody, a polyclonal antibody, a recombinant antibody, a multispecific antibody, any combination thereof, or any antigen-binding fragment thereof. In certain aspects, the antibody or fragment thereof is a complete IgG immunoglobulin, e.g., a human IgG1 immunoglobulin, comprising two heavy chains and two light chains. In certain aspects the transporter molecule comprises or consists of an antibody fragment, e.g., an Fv fragment, an Fab fragment, an F(ab')2 fragment, an Fab' fragment, a dsFv fragment, a scFv fragment, or an sc(Fv)2 fragment.

In certain embodiments, a transporter molecule as provided herein comprises an antibody scFv fragment, where the scFv comprises a VH domain or region and a VL domain or region, fused to each other either directly or via a linker, e.g., a flexible linker. The VH and VL in a scFv can be arranged such that the VH is at the N terminus and the VL is at the C terminus, or vice versa. Where the VH and VL are fused via a linker, the scFv can comprise, from the amino terminus: VH-L-VL, wherein L is the linker, or VL-L-VH, where L is the linker.

Various linkers suitable for preparing scFvs are known to the person of ordinary skill in the art. Some non-limiting examples include the linker (Gly$_4$Ser)n, where n is a positive integer selected from the group consisting of 1, 2, 3, 4, 5, 6, 7, 8, 9 and 10 (SEQ ID NO: 232), Ser(Gly$_4$Ser)n, where n is a positive integer selected from the group consisting of 1, 2, 3, 4, 5, 6, 7, 8, 9 and 10 (SEQ ID NO: 233), GGGGSGGGGSGGGGS (SEQ ID NO: 234), GGGGSGGGGSGGGG (SEQ ID NO: 235), GGGGSGGGGSGGGGSAL (SEQ ID NO: 236), or GGGGSGGGGSGGGGSA (SEQ ID NO: 237).

In certain aspects the transporter molecule provided herein comprises a scFv, where the scFv comprises the VH and VL of Bbbt0241, the Bbbt0626, Bbbt0632, Bbbt0654, Bbbt0726, Bbbt0727, Bbbt0732, Bbbt0754, Bbbt0674, Bbbt0755, Bbbt0643, Bbbt0579, or Bbbt0671.

In certain aspects, a transporter molecule as provided herein is associated with a payload, such that the transporter molecule can facilitate transport of the payload across the BBB. In certain aspects, the payload is a peptide or polypeptide, and is fused, via a peptide bond, to the immunoglobulin-derived polypeptide. The fusion can be, for example to the N-terminus of either the heavy chain or the light chain, to the C-terminus of either the heavy chain or the light chain, or any combination thereof. In certain aspects, the payload is a peptide or polypeptide attached to one or more sites on the immunoglobulin-derived polypeptide via disulfide bonds. In certain aspects the immunoglobulin-derived polypeptide can be engineered to contain more or fewer cysteine residues to facilitate precise and/or dense attachment of one or more copies of the payload to the immunoglobulin-derived polypeptide. In certain aspects, the payload is chemically conjugated to the immunoglobulin-derived polypeptide for example, via CMK (chloromethylketone) coupling via free cysteines; Maleimide coupling via free cysteines; NHS coupling to free amine groups; 'Click' chemistry (alkyne+azide); 'Oxime ligation' (hydrazide or hydroxylamine+aldehyde) or 'Kent Ligation' (thioester+native cysteine). Native or engineered cysteine residues are particularly useful as they allow conjugation through a thiol reactive group such as maleimide or haloacetyl.

In certain aspects, the payload is associated with the immunoglobulin-derived polypeptide via non-covalent bonds.

Any type of payload for which there is a need to transport into the CNS can be associated with a transporter molecule as provided herein. For example, the payload can be a peptide or polypeptide, e.g., a peptide tag, hormone or derivative thereof, an enzyme, a cytokine, a lymphokine, or a heterologous antibody or fragment thereof; a polynucleotide, e.g., a microRNA, a microRNA inhibitor, an antisense molecule, and RNAi molecule, a cDNA, or a gene therapy agent; a carbohydrate, a polymer such as polyethylene glycol, a small molecule drug such as a chemotherapeutic agent or an antimicrobial or antiviral agent, a prodrug, a lipid, a biological response modifier, a detectable label, or a combination of two or more of the agents.

In certain aspects, the payload comprises interleukin-1 receptor antagonist (IL-1Ra) or an active fragment thereof. As described elsewhere herein, IL-1Ra, upon entry into the CNS, can confer an analgesic effect on a subject experiencing neuropathic pain (Gabay E1, et al., Eur J Pain. 2011 March; 15(3):242-8). The antagonist must reach the CNS, however, before any effect is observed. Coupling of IL-1Ra to a BBB transporter is a way to facilitate delivery of IL-1Ra to the CNS rather than intrathecal delivery. Accordingly, this disclosure provides transporter molecules comprising an immunoglobulin-derived polypeptide fused, or otherwise associated with IL-1Ra or an active fragment thereof. IL-1Ra can be attached to a transporter molecule as provided herein by any suitable means, for example the IL-1Ra polypeptide can be fused to the immunoglobulin-derived polypeptide as provided herein, at the N-terminus or at the C terminus of either the heavy chain or the light chain. For example, this disclosure provides a transporter molecule fused to IL-1Ra, comprising a VH having the amino acid sequence SEQ ID NO: 38 (Bbbt0632) fused to IL-1Ra (SEQ ID NO: 223) fused to the C terminus of SEQ ID NO: 38 via a linker having the amino acid sequence SEQ ID NO: 222, and a VL having the amino acid sequence SEQ ID NO: 47, or a VH having the amino acid sequence SEQ ID NO: 2 (Bbbt0241) fused to IL-1Ra (SEQ ID NO: 223) fused to the C terminus of SEQ ID NO: 2 via a linker having the amino acid sequence SEQ ID NO: 222, and a VL having the amino acid sequence SEQ ID NO: 11. Based on this disclosure, a person of ordinary skill in the art could contemplate myriad other transporter molecules comprising an immunoglobulin-derived polypeptide provided herein fused to IL-1Ra, such that the transporter molecule retains activity, e.g., the transporter molecule can specifically bind to BMVEC, can internalize into BMVEC, or can transport across BMVEC either in vivo or in vitro.

Enkephalins are naturally occurring peptides that are released by neurons in the CNS which have potent analgesic effects. Enkephalin analogs such as dalargin have been described and can confer an analgesic effect on a subject experiencing neuropathic pain, but must reach the CNS, before any effect is observed (Rousselle et al. (2003) J. Pharm. Exper. Ther. 306:371-376). Coupling encephalins and analogs to a BBB transporter is a way to facilitate the delivery of enkephalins and analogs across the BBB. Accordingly, this disclosure provides transporter molecules comprising an immunoglobulin-derived polypeptide fused, or otherwise associated with an enkephalins or enkephalin analog.

In certain aspects, the payload comprises a tumor necrosis factor alpha (TNF-α) inhibitor. It has been shown that TNF-α inhibitors delivered across the BBB are neuroprotective and can be used to treat Alzheimer's disease (Zhou et al. (2011) J. Pharm. Exp. Ther. 339:618-23; Tobinck and Gross (2008) J. NeuroInflam 5:2). Coupling of a TNF-α inhibitor to a BBB transporter is a way to facilitate the delivery of such inhibitors across the BBB. Accordingly, this disclosure provides transporter molecules comprising an immunoglobulin-derived polypeptide fused, or otherwise associated with a TNF-α inhibitor. A TNF-α inhibitor can be attached to a transporter molecule as provided herein by any suitable means, for example a polypeptide TNF-α inhibitor can be fused to the immunoglobulin-derived polypeptide as provided herein, at the N-terminus or at the C terminus of either the heavy chain or the light chain. A number of suitable TNF-α inhibitors have been described in the art, and include but are not limited to the ligand-binding portion of the TNF receptor (TNFR), e.g., etanercept (ENBREL®); and antibodies that bind TNF-α, e.g., adalimumab (HUMIRA®), infliximab (REMICADE®), golimumab (SIMPONI®).

In certain aspects, the payload comprises an interferon-β, Glial-derived neurotrophic factor (GDNF), tumor necrosis factor receptor (TNFR), nerve growth factor (NGF), brain derived neurotrophic factor (BDNF), neurotrophin-4/5, neurotrophin (NT)-3, a neurturin, neuregulin, a netrin, ciliary neurotrophic factor (CNTF), stem cell factor (SCF), a semaphorin, hepatocyte growth factor (HGF), epidermal growth factor (EGF), transforming growth factor (TGF)-cx, TGF-B, vascular endothelial growth factor (VEGF), platelet-derived growth factor (PDGF), heregulin, artemin, persephin, interleukins, granulocyte-colony stimulating factor (CSF), granulocyte-macrophage-CSF, cardiotrophin-1, hedgehogs, leukemia inhibitory factor (LIF), midkine, pleiotrophin, erythropoietin (EPO), bone morphogenetic proteins (BMPs), netrins, saposins, or a combination thereof.

Transporter Molecule Activity

Certain transporter molecules as provided herein possess the ability to transport across the BBB, either alone or associated with a heterologous payload molecule. Activity can be demonstrated by a number of assays. For example, in certain aspects, a transporter molecule as provided herein can bind to BMVEC from one or more species, e.g., human, cynomolgus monkey, murine, rat, or bovine BMVEC. Binding can be demonstrated in various ways known to persons of ordinary skill in the art, e.g., the FMAT assay described elsewhere herein. In certain aspects, the BMVEC are brain capillary endothelial cells (BCEC). In certain aspects, a transporter molecule as provided herein can pass through a monolayer of BCEC in an in vitro transcytosis assay. Moreover, in certain aspects, a transporter molecule as provided herein can compete with the single-domain antibody FC5 (see, e.g., PCT publication WO02/057445) or Bbbt0241 for binding to BMVEC in the competition FMAT assay, explained in detail elsewhere herein. Examples of transporter molecules which compete for BMVEC binding to FC5 or Bbbt0241 include those transporter molecules comprising the VH and VL domains of Bbbt0626, Bbbt0727, Bbbt0632, Bbbt0654, Bbbt0726, Bbbt0732, or Bbbt0754. In certain alternative aspects, a transporter molecule as provided herein binds to BMVEC, but does not compete with the single-domain antibody FC5 or Bbbt0241 for binding to BMVEC in the competition FMAT assay. Examples of transporter molecules which do not compete for BMVEC binding with FC5 or Bbbt0241 include those transporter molecules comprising the VH and VL domains of Bbbt0643, Bbbt0674, Bbbt0755, Bbbt0579 or Bbbt0671.

In certain aspects, transporter molecule activity can be demonstrated in vivo. For example, the κ-opioid peptide dynorphin, can cause diuresis in an animal model, but only if it reaches the CNS. Accordingly, a transporter molecule as provided herein can be conjugated to one or more dynorphin molecules and administered peripherally, e.g., intravenously, to a subject, e.g., in a rat model, and activity can be demonstrated by increased urine output in the animals.

In another example, IL-1Ra, can reduce hyperalgesia brought on by neuropathic pain, but only if it reaches the CNS. Accordingly a transporter molecule as provided herein can be fused to IL-1Ra and administered peripherally, e.g., intravenously or subcutaneously, in a neuropathic pain model, e.g., in a rat partial sciatic nerve ligation assay. An analgesic effect demonstrates that the transporter molecule can cross the BBB thereby reducing neuropathic pain.

In certain aspects, transporter molecule activity can be demonstrated by visualization of the transporter molecule in the CNS. For example, a tritium-labeled transporter molecule can be delivered to a subject, e.g., a mouse peripherally, e.g., intravenously, and then visualized in the CNS via quantitative whole body radiography. In certain aspects, the transporter molecule localizes in specific regions of the CNS, e.g., the cortex of cerebellum, the gray matter of the cerebrum, the gray matter of the spinal cord, the pons, or a combination thereof.

Polynucleotides

This disclosure provides polynucleotides encoding any transporter molecule provided herein. In certain aspects an isolated polynucleotide or a polynucleotide composition comprising two or more polynucleotides is provided, which singly or collectively encodes a transporter molecule can encode the immunoglobulin-derived polypeptide, as well as the payload to be transported across the BBB. In certain aspects, an isolated polynucleotide, or a polynucleotide composition comprising two or more isolated polynucleotides is provided, where the polynucleotide or polynucleotides comprise one or more nucleic acid molecules singly or collectively encoding an immunoglobulin-derived polypeptide comprising one or more of Bbbt0241, Bbbt0351, Bbbt0626, Bbbt0632, Bbbt0654, Bbbt0726, Bbbt0727, Bbbt0732, Bbbt0754, Bbbt0674, Bbbt0755, Bbbt0643, Bbbt0579, or Bbbt0671.

In certain aspects, an isolated polynucleotide is provided, where the polynucleotide comprises a nucleic acid molecule encoding an immunoglobulin-derived polypeptide transporter molecule or a fragment or subunit thereof, where the transporter molecule comprises a VH, a VL, or a VH and a VL, and where the nucleic acid molecule encodes SEQ ID NO: 2, SEQ ID NO: 11, or SEQ ID NO: 2 and SEQ ID NO: 11; SEQ ID NO: 20, SEQ ID NO: 29, or SEQ ID NO: 20 and SEQ ID NO: 29; SEQ ID NO: 38, SEQ ID NO: 47, or SEQ ID NO: 38 and SEQ ID NO: 47; SEQ ID NO: 56, SEQ ID NO: 65, or SEQ ID NO: 66 and SEQ ID NO: 65; SEQ ID NO: 74, SEQ ID NO: 83, or SEQ ID NO: 74 and SEQ ID NO: 83; SEQ ID NO: 92, SEQ ID NO: 101, or SEQ ID NO: 92 and SEQ ID NO: 101; SEQ ID NO: 110, SEQ ID NO: 119, or SEQ ID NO: 110 and SEQ ID NO: 119; SEQ ID NO: 128, SEQ ID NO: 137, or SEQ ID NO: 128 and SEQ ID NO: 137; SEQ ID NO: 146, SEQ ID NO: 155, or SEQ ID NO: 146 and SEQ ID NO: 155; SEQ ID NO: 164, SEQ ID NO: 173, or SEQ ID NO: 164 and SEQ ID NO: 173; SEQ ID NO: 182, SEQ ID NO: 191, or SEQ ID NO: 182 and SEQ ID NO: 191; SEQ ID NO: 200; SEQ ID NO: 209, SEQ ID NO: 218, or SEQ ID NO: 209 and SEQ ID NO: 218; or SEQ ID NO: 226, SEQ ID NO: 227, or SEQ ID NO: 226 and 227.

In certain aspects, an isolated polynucleotide is provided, where the polynucleotide comprises a nucleic acid molecule encoding an immunoglobulin-derived polypeptide transporter molecule or a fragment or subunit thereof, where the transporter molecule comprises a VH, a VL, or a VH and a VL, and where the nucleic acid molecule comprises SEQ ID NO: 1, SEQ ID NO: 10, or SEQ ID NO: 1 and SEQ ID NO: 10; SEQ ID NO: 19, SEQ ID NO: 28, or SEQ ID NO: 19 and SEQ ID NO: 28; SEQ ID NO: 37, SEQ ID NO: 46, or SEQ ID NO: 37 and SEQ ID NO: 46; SEQ ID NO: 55, SEQ ID NO: 64, or SEQ ID NO: 55 and SEQ ID NO: 64; SEQ ID NO: 73, SEQ ID NO: 82, or SEQ ID NO: 73 and SEQ ID NO: 82; SEQ ID NO: 91, SEQ ID NO: 100, or SEQ ID NO: 91 and SEQ ID NO: 100; SEQ ID NO: 109, SEQ ID NO: 118, or SEQ ID NO: 109 and SEQ ID NO: 118; SEQ ID NO: 127, SEQ ID NO: 136, or SEQ ID NO: 127 and SEQ ID NO: 136; SEQ ID NO: 145, SEQ ID NO: 154, or SEQ ID NO: 145 and SEQ ID NO: 154; SEQ ID NO: 163, SEQ ID NO: 172, or SEQ ID NO: 163 and SEQ ID NO: 172; SEQ ID NO: 181, SEQ ID NO: 190, or SEQ ID NO: 181 and SEQ ID NO: 190; SEQ ID NO: 199; or SEQ ID NO: 208, SEQ ID NO: 217, or SEQ ID NO: 208 and SEQ ID NO: 217.

In certain aspects, the isolated polynucleotide further comprises a nucleic acid molecule that encodes a heterologous payload, e.g., a polypeptide or polynucleotide payload. Exemplary payloads are provided elsewhere herein.

In certain aspects, a polynucleotide composition comprising two or more isolated polynucleotides is provided, where the polynucleotides comprise two or more nucleic acid molecules encoding an immunoglobulin-derived polypeptide transporter molecule or a fragment or subunit thereof, where the transporter molecule comprises a VH and a VL, and where the nucleic acid molecules encodes, respectively, SEQ ID NO: 2 and SEQ ID NO: 11; SEQ ID NO: 20 and SEQ ID NO: 29; SEQ ID NO: 38 and SEQ ID NO: 47; SEQ ID NO: 56 and SEQ ID NO: 65; SEQ ID NO: 74 and SEQ ID NO: 83; SEQ ID NO: 92 and SEQ ID NO: 101; SEQ ID NO: 110 and SEQ ID NO: 119; SEQ ID NO: 128 and SEQ ID NO: 137; SEQ ID NO: 146 and SEQ ID NO: 155; SEQ ID NO: 164 and SEQ ID NO: 173; SEQ ID NO: 182 and SEQ ID NO: 191; SEQ ID NO: 209 and SEQ ID NO: 218; or SEQ ID NO: 226 and SEQ ID NO: 227.

In certain aspects, a polynucleotide composition comprising two or more isolated polynucleotides is provided, where the polynucleotides comprise two or more nucleic acid molecules encoding an immunoglobulin-derived polypeptide transporter molecule or a fragment or subunit thereof, where the transporter molecule comprises a VH and a VL, and where the nucleic acid molecules comprise, respectively, SEQ ID NO: 1 and SEQ ID NO: 10; SEQ ID NO: 19 and SEQ ID NO: 28; SEQ ID NO: 37 and SEQ ID NO: 46; SEQ ID NO: 55 and SEQ ID NO: 64; SEQ ID NO: 73 and SEQ ID NO: 82; SEQ ID NO: 91 and SEQ ID NO: 100; SEQ ID NO: 109 and SEQ ID NO: 118; SEQ ID NO: 127 and SEQ ID NO: 136; SEQ ID NO: 145 and SEQ ID NO: 154; SEQ ID NO: 163 and SEQ ID NO: 172; SEQ ID NO: 181 and SEQ ID NO: 190; or SEQ ID NO: 208 and SEQ ID NO: 217.

In certain aspects, the polynucleotide composition comprising two or more isolated polynucleotides further comprises a nucleic acid molecule that encodes a heterologous payload, e.g., a polypeptide or polynucleotide payload. Exemplary payloads are provided elsewhere herein.

In certain aspects, a vector, or two or more vectors are provided, to facilitate display, screening, isolation, cloning, and/or expression of a transporter molecule as provided herein. In certain aspects the vector or vectors is/are expression vectors.

In certain aspects, two or more nucleic acid molecules of a polynucleotide composition can be situated in the same vector. In certain aspects, the two or more nucleic acid molecules of the polynucleotide composition can be situated in at least two separate vectors.

Expression vectors are used express isolated polynucleotide(s) encoding a transporter molecule as provided herein. Recombinant expression vectors are replicable DNA constructs which have synthetic or cDNA-derived DNA fragments encoding a polypeptide chain of a transporter molecule, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated.

In certain aspects an isolated polynucleotide or composition comprising two or more isolated polynucleotides is provided, in which the nucleic acid molecule is operably associated with a promoter, or the two or more nucleic acid molecules are operably associated with two or more promoters, where the promoters can be the same or different.

DNA regions are "operably associated" when they are functionally related to each other. For example, DNA for a signal peptide (secretory leader) is operably associated with DNA for a polypeptide if it is expressed as a precursor which participates in the secretion of the polypeptide; a promoter is operably associated with a coding sequence if it controls the transcription of the sequence; or a ribosome binding site is operably associated with a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

In certain aspects an isolated host cell is provided that comprises a polynucleotide as provided herein. In certain aspects one or more isolated host cells are provided that comprise the two or more polynucleotides of the polynucleotide composition provided herein.

Suitable host cells for expression of transporter molecules provided herein include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems can also be employed to express transporter molecules. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer operably associated with the gene to be expressed, and other 5' or 3' flanking nontranscribed sequences, and 5' or 3' nontranslated sequences, such as ribosome binding sites, a polyadenylation site, splice donor and acceptor sites, and transcriptional termination sequences. Baculovirus systems for production of heterologous proteins in insect cells are reviewed by Luckow and Summers, BioTechnology 6:47 (1988).

Host cells provided herein can be utilized in a method of making a transporter molecule as provided herein, where the method includes (a) culturing the host cell and (b) isolating the transporter molecule expressed from the host cell. In certain aspects, a payload moiety is expressed as part of the transporter molecule. In certain aspects, the method further comprises associating the transporter molecule with a payload moiety, e.g., by chemical conjugation.

Pharmaceutical and Diagnostic Compositions

In another aspect, the disclosure provides a composition, for example, a pharmaceutical composition, containing one or a combination of transporter molecules as provided herein, where the one or more transporter molecules comprise one or more payload moieties for transport across the BBB, formulated together with a pharmaceutically acceptable carrier. Such compositions can include one or two or more different transporter molecules as provided herein.

Pharmaceutical compositions can also be administered in combination therapy and/or combined with other agents. For example, the combination therapy can include a transporter molecule as provided herein combined with at least one other therapy wherein the therapy can be, e.g., immunotherapy, chemotherapy, radiation treatment, or drug therapy.

The pharmaceutical compounds provided herein can include one or more pharmaceutically acceptable salts. Examples of such salts include acid addition salts and base addition salts.

A pharmaceutical composition provided herein can also include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that can be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of a certain particle size in the case of dispersions, and by the use of surfactants.

These compositions can also contain adjuvants such as preservatives, wetting agents, emulsifying agents and dispersing agents. Prevention of presence of microorganisms can be ensured both by sterilization procedures and by the inclusion of various antibacterial and antifungal agents, for example, paraben, chlorobutanol, phenol sorbic acid, and the like. Isotonic agents, such as sugars, sodium chloride, and the like can also be added into the compositions. In addition, prolonged absorption of the injectable pharmaceutical form can be brought about by the inclusion of agents which delay absorption such as aluminum monostearate and gelatin.

Suitable and exemplary compositions and formulations, and methods or preparing such compositions and formulations can be found, e.g., in PCT Publication No: WO 2009/058379, in PCT Publication No: WO 2011/130324, and in PCT Publication No: WO 2011/130328.

A composition as provided herein can also be a diagnostic composition, e.g., a composition for delivering an imaging payload to the CNS. Accordingly a diagnostic composition comprising a transporter molecule, a polynucleotide or polynucleotides encoding a transporter molecule, a vector vectors comprising the polynucleotide(s), or a host cell comprising the vector(s) is provided.

Methods of Using Transporter Molecules

Transporter molecules as provided herein have in vitro and in vivo diagnostic and therapeutic utilities. For example, these molecules can be administered to cells in culture, e.g. in vitro or ex vivo, or in a subject, e.g., in vivo, to treat, prevent or diagnose a variety of diseases or disorders of the CNS.

Accordingly this disclosure provides a method of treating, diagnosing, or preventing a disease, disorder, or injury of the CNS, where the method comprises peripherally administering to a subject in need of treatment a composition comprising a transporter molecule as provided herein, wherein the transporter molecule comprises a therapeutic or diagnostic payload moiety capable of diagnosing, preventing, or treating the disease, disorder, or injury upon exposure to the CNS following transport across the BBB, and wherein an amount of the therapeutic or diagnostic payload moiety is sufficient to diagnose, prevent, or treat the disease, disorder, or injury is transported across the BBB, thereby treating the disease, disorder, or injury.

The disclosure encompasses the use of a transporter molecule as provided herein conjugated or fused to a payload moiety (e.g., therapeutic agent or drug) for transport of the moiety across the BBB for prevention, management, treatment or amelioration of one or more symptoms associated with disease, disorder, or injury of the CNS, either alone or in combination with other therapies.

In certain aspects, the payload moiety is released from the transporter molecule following entry into the CNS. In certain aspects, the payload moiety remains associated with the transporter molecule without compromising its activity.

Any number of payload moieties can be employed to diagnose, prevent, or treat a disease, disorder or injury of the CNS, where the disease, disorder, or injury comprises multiple sclerosis (MS), amylotrophic lateral sclerosis (ALS), Huntington's disease, Alzheimer's disease (AD), Parkinson's disease, spinal cord injury, traumatic brain injury, stroke, neuropathic pain, neurodegeneration, neuroinflammation, dementia, progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease), Wallerian Degeneration, optic neuritis, transverse myelitis, post radiation injury, neurologic complications of chemotherapy, acute ischemic optic neuropathy, vitamin E deficiency, isolated vitamin E deficiency syndrome, Bassen-Kornzweig syndrome, Marchiafava-Bignami syndrome, metachromatic leukodystrophy, trigeminal neuralgia, Bell's palsy, primary tumors (e.g., glioblastoma) or secondary metastases, or any combination thereof.

In certain aspects, the therapeutic agent is interleukin-1 receptor antagonist (IL-1Ra), and the disease, disorder, or injury is neuropathic pain.

The disclosure also provides methods of diagnosing diseases. Transporter molecules as provided herein that carry moieties such as imaging agents can be implemented in a method used to diagnose the disease.

The disclosure further provides methods of imaging specific targets. In one embodiment, a transporter molecule as provided herein can be fused or conjugated to payloads that are imaging agents such as green fluorescent proteins, other fluorescent tags (Cγ3, Cγ5, Rhodamine and others), biotin, or radionuclides, in order to transport these payloads across the BBB in methods to image the presence, location, or progression of a specific target in the CNS. In other embodiments, the method of imaging a target via utilization of a transporter molecule as provided herein is performed by MRI, PET scanning, X-ray, fluorescence detection or by other detection methods known in the art.

The disclosure also provides method of monitoring disease progression, relapse, treatment, or amelioration using a transporter molecule as provided herein. In one embodiment, methods of monitoring disease progression, relapse, treatment, or amelioration is accomplished by the methods of imaging, diagnosing, or contacting a compound/target in the CNSs through utilization of a transporter molecule as provided herein.

Kits

Also within the scope of the disclosure are kits comprising compositions as provided herein (e.g. transporter molecules capable of delivering substances across the BBB) and instructions for use. The kit can further contain at least one additional reagent, or one or more additional transporter molecules. Kits typically include a label indicating the intended use of the contents of the kit. The term label includes any writing, or recorded material supplied on or with the kit, or which otherwise accompanies the kit.

EQUIVALENTS

Those skilled in the art will recognize, or be able to ascertain using no more than routine experimentation, many equivalents to the specific embodiments described herein. Such equivalents are intended to be encompassed by the following claims.

The practice of the appended claims will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1: Construction and Characterization of an Improved FC5 Variant, Bbbt0351

This example describes the construction of an improved camelid BBB transporter molecule from FC5, a camelid single domain antibody that crosses the blood brain barrier. Stanimirovic, et al., *J. Neurochem.* 95:1201 (2005). FC5 recognizes both rodent and human brain endothelial cells. The binding target for FC5 is reported to be TMEM30a, a glycosylated orphan receptor with two transmembrane domains. TMEM30a has three isoforms and is ubiquitously expressed in in most cell types.

FC5 was subjected to CDR3 alanine and parsimonious mutagenesis and a number of mutants were created in DAb format and tested for ability to express and to bind mouse brain endothelial cells. Those variants that expressed and yielded purified protein after purification over a HIS trap column, but that didn't provide a binding signal in the FMAT binding assay on mouse brain endothelial cells were further evaluated. Variant Bbbt0351 comprises two amino acid substitutions relative to the variable region of FC5, a T97A substitution at Kabat position 97, and a T100aD substitution at Kabat position 100a. The nucleotide and amino acid sequences of Bbbt0351 are presented as SEQ ID Nos 199-207 (Table 2). Bbbt0351, when expressed with an Fc domain, is genetically fused to the N-terminal end of the hIgG1 hinge region.

Bbbt0351 is a mutant form of FC5 that shows no binding to brain endothelial cells, but has an increased rate of transport compared to that of FC5 in vitro and in vivo. Transport of Bbbt0351-Fc across brain endothelial cells was compared to FC5-Fc in two rat in vitro BBB models. The primary rat brain endothelial cell BBB model is described (Watson P. M. D. et al., BMC Neuroscience 2013: 14, 59-79) and the method used to measure transcytosis across this model barrier is as follows: cell culture medium was removed from the upper and lower compartments of RBECs cultured in triplicate on cell culture inserts and replaced with Ringer's HEPES buffer (without BSA). The molecules of interest were added to the upper compartments to give the desired final concentration in each well. Cultures were incubated at 37° C. with shaking and transferred to another well with fresh buffer in the lower compartment after 30, 60 and 90 minutes. Samples were collected from the lower compartment and analyzed by nano-LC SRM mass spectrometry. The method for measuring transcytosis of molecules across a rat cell line BBB model is described (Haqqani A. S. et al., Method. Mol. Pharmaceutics. 2013; 10, 1542-1556). The transport of large molecules across primary rat brain endothelial cells or an immortalized rat brain endothelial cell line can be detected by the nano-LC SRM mass spectrometry technique.

The comparison of in vivo transport of Bbbt0351-Fc and FC5-Fc are shown in FIGS. 1A and B. The results are shown as apparent permeability ($P_{APP}$), which is calculated using the equation $(dQ_r/dT)/(A \times C_0)$ where $dQ_r/dT$ is the cumulative amount of molecule in the lower compartment vs time, A is the surface area of the cell culture insert, and $C_0$ is the starting concentration of the molecule in the upper compartment. These results show that, despite showing no signal in the FMAT binding assay, Bbbt0351-Fc shows better transport than FC5-Fc across in both in vitro BBB models.

Example 2: Construction and Characterization of Bbbt0241

This example describes the construction of Bbbt0241, a humanized BBB transporter molecule starting with FC5.

FC5 was humanized by addition of a light chain, according to the following methods (FIG. 2A). The FC5 based single chain Fv fragment (FC5-scFv) phage library was based upon the previously described CAT 2.0 library (Lloyd C. et al., Protein Eng Des Sel 2009; 22 (3); 159-68).

Briefly, VL gene segments were amplified using germline specific primers (Hutchings C. Antibody Engineering. Springer Laboratory Manuals. 2001; 93-108) and were subsequently cloned into a modified pCANTAB6 vector (McCafferty J. et al., J. Appl. Biochem. Biotechnol. 1994; 47; 157-171). This vector contains a [Gly$_4$Ser]$_3$ linker with flanking XhoI and ApaLI site to allow independent heavy and light chain cloning. An already cloned light chain library acted as the acceptor vector for the insertion of the FC5 V$_H$H upstream of the [Gly$_4$Ser]$_3$ via SfiI and XhoI directional cloning, creating FC5-scFv libraries ($10^8$ in diversity). FC5 was shown to bind protein A by ELISA (V$_H$3 family clones are able to bind protein A), and therefore, the libraries were selected on protein A to enrich for only those clones that formed complete scFvs and were still able to bind protein A.

Following protein A selection, the phage particles were allowed to infect *E. coli* and individual colonies were picked into 96 well plates for screening.

The initial screen of humanized FC5-scFv variants was via a fluorometric microvolume assay technology assay (FMAT) screening using crude periplasmic extracts (peripreps) of *E. coli* cells expressing soluble scFvs (FIG. 3A). These scFvs were allowed to incubate with detection antibodies, namely a mouse anti-HIS antibody that would bind the 6×HIS tag at the C-terminal end of the scFv followed by anti-mouse IgG labelled with Alexafluor647 that would detect the anti-HIS antibody. This tertiary complex was then added to a brain microvascular endothelial (BMVEC) cell line from mouse (B.End3) in homogenous solution and incubated. ScFvs that bound receptors on the surface of the cells was read as a concentration of fluorescent signal around the cell resulting in a positive binding event. The results of the FMAT assay for Bbbt0241 are shown in FIG. 3B.

Positive scFvs were termed as 'hits' and were subsequently expressed and purified as described (Dobson et al., MAbs 2009; 1 (6); 552-562). Briefly, scFv plasmids were cultured in *E. coli* TG1 cells, expression was induced with 1 mM isopropyl β-D-1-thiogalactoside (IPTG), and scFv proteins were isolated from the periplasm by osmotic shock using 50 mM Tris-HCl, 0.5 mM EDTA, 500 mM sucrose (TES) pH7.4 buffer and by capture of the C-terminal His-tag on Ni2_-nitrilotriacetic acid chromatography. The isolated plasmids were then re-expressed and purified by standard HIS purification procedures over Nickel columns. Binding of 'hits' was confirmed in the FMAT assay using the mouse B.End3 cell-line with known concentrations of purified scFv. Moreover, the ability of humanised FC5 hIgGs to compete with FC5 DAb for binding to B.End3 cells was tested in a competition FMAT assay. FIG. 3C shows photomicrographs of the B.End3 cells in a competition FMAT assay using a constant concentration of FC5 DAb and an increasing concentration of competitor hIgG1 e.g., Bbbt0241. CEA6 is a negative control hIgG1. FIG. 3D is a graph that quantitatively shows the competition. Confirmed 'hits' were then tested for binding to BMVECs from other species, e.g., rat and cynomolgus monkey. From the original screen of humanized FC5 variants, the scFv Bbbt0241 was identified as a lead candidate. The sequences of Bbbt0241 are presented as SEQ ID NOs 1-18 and 199 (Table 2).

Localization of Bbbt0241 administered to rats was analysed by a quantitative whole bodyautoradiography (QWBA) as follows. Bbbt0241 hIgG1TM was labelled with tritiated N-succinimidyl propionate (NSP). A single aliquot of NSP containing 1.6 mCi was dispensed into a vial. The solvent was evaporated under a gentle stream of nitrogen gas at room temperature. The residue was re-suspended in DMSO (Hybri-Max-Sigma) and mixed to ensure complete dissolution of radiolabelled material. A single aliquot (1 mL) of antibody solution was dispensed into the vial. The solution was then allowed to stand at +4° C. for approximately 16 hours (over night). The [3H]-antibody solution was then purified by gel filtration using MWCO 40000 Zebraspin desalting columns (Pierce). The specific activity of the material was determined following purification, based on the UV response of the purified Bbbt0241 in the solution following analysis by Size Exclusion Chromatography, and the radioactivity present. $[_{3H}]$-Bbbt0241 was formulated as an intravenous solution in phosphate buffered saline pH7.4.

Male Sprague Dawley rats were administered a single dose of tritiated Bbbt0241 intravenously at 30 mg/kg. Three animals were analysed at 24 hours after dosing for the levels of Bbbt0241 in brain tissue relative to the amount in plasma. At 24 hours post dose, the animals were anaesthetised using isofluorane and approx. 1 mL of blood was collected by cardiac puncture. Animals were then sacrificed by exsanguination through the left ventricle of the heart using approx. 50 mL of phosphate buffered saline (PBS), containing 10 IU/mL lithium heparin.

Brains were removed and frozen in isopentane cooled to between −20 to −30° C. The brain samples were stored at below −70° C. prior to analysis. The blood was processed to serum and levels of radioactivity were analysed by LSC. The whole rat brains were assessed for the degree of perfusion and then weighed. Approximately 5 volumes of cold (approximately 4° C.) PBS containing Complete® protease inhibitor (Roche Diagnostics) was added to the whole brain sample and they were then homogenised in a 10 mL Potter-Elvehjem mortar type glass homogeniser with PTFE pestle, using 2×10 clockwise strokes with a 5 second rest time. Aliquots of unprocessed brain homogenate were combusted in a Packard 306 sample combustor and the measured radioactivity levels used to calculate the recovery of radioactivity after sample processing.

The homogenate was transferred to LoBind tubes (Eppendorf) and processed into the soluble fragment containing the intracellular and extracellular proteins, by centrifugation at 16000 g for 1 hour at 4° C. Following removal of the soluble fraction, the resulting pellet, was homogenised in 5 volumes of cold PBS Complete® containing 0.5% Tween 20 (approximately 4° C.), using 1×10 clockwise strokes in the glass homogeniser. The homogenate was transferred to LoBind tubes and centrifuged at 16000 g at 4° C. for 1 hour. The resulting pellet fraction contained the radioactivity bound to membrane proteins and membrane bound target receptors from the parenchyma and BBB endothelium. Finally, any remaining radioactivity that was loosely bound to the pellet fraction was extracted with 5 volumes PBS Complete® containing 1% SDS at room temperature and following homogenisation and centrifugation in a LoBind tube, as described above. The total fraction weights were recorded for all samples and levels of radioactivity measured in weighed aliquots of the collected fractions. These samples were then analysed by liquid scintillation counting (LSC). Samples were kept on ice during all stages of tissue processing.

Four animals were screened for whole-body and brain exposure at 5 min, 4 hours, 24 hours, and 72 hours after dosing. The animals were sacrificed by immersion in hexane/solid $CO_2$ (ca. −70° C.) under isofluorane anaesthesia, at 5 minutes, 4, 24 and 72 hours post dose. Prior to sacrifice, blood samples (approximately 0.5 ml) were taken from a peripheral tail vein and processed to serum. After removal of limbs and tail, the carcass was embedded, with left lateral side uppermost, in a 1% aqueous solution of carboxymethyl cellulose and frozen for at least 30 minutes in hexane cooled to −70° C. with solid $CO_2$. The animal blocks were stored at −20° C. until required for sectioning. At sectioning each block was mounted in a Leica CM3600 Cryomacrotome (Leica Microsystems GmbH, Germany) maintained at approximately −20° C. Sagittal whole body sections (30 μm) were prepared at up to five different levels of the rat body to include as many tissues as possible:

Level 1: Exorbital lachrymal gland
Level 2: Intra-orbital lachrymal gland
Level 3: Harderian gland/adrenal gland
Level 4: Thyroid gland
Level 5: Brain and spinal cord The sections were mounted on sectioning tape (T410, TAAB) and labelled. All sections were freeze-dried for approximately 1 hour (LyoPro 3000 freeze drier) prior to exposure on phosphor-imaging plates. Sections were chosen for phosphor-imaging to best represent the tissues and organs of interest. Together with the calibration standards, the sections were placed against pre-erased phosphor-imaging plates. The imaging plates were exposed for 14 days at room temperature enclosed in light tight cassettes in a lead shielding box to protect from environmental radiation. Following exposure the imaging plates were scanned at a pixel size of 50 mm using a Fuji FLA-5100 Image Analyser (Raytek, UK). The tissues and organs of interest were quantified using Seescan version 2 (LabLogic, UK).

The quantitative whole body autoradiography (QWBA) study indicated that Bbbt0241 hIgG1TM was specifically transported to discrete regions of the brain and spinal cord, namely, the cortex of cerebellum, grey matter of cerebrum, grey matter of spinal cord and pons. Exposure studies demonstrated a 1-1.5% brain:plasma ratio of Bbbt0241 at 24 hours post intravenous (i.v.) dosing. (A similar exposure level has also been demonstrated with Bbbt0626 hIgG1TM in mice.).

Bbbt0241 was also tested in the in vitro transcytosis assay (FIG. 4A) alongside a negative control IgG (NIP228 IgG) using the method described in (Haqqani A. S., Caram-Salas N., Ding W., Brunette E., Delaney C. E., Baumann E., Boileau E., Stanimirovic D. Multiplexed Evaluation of Serum and CSF Pharmacokinetics of Brain-Targeting Single-Domain Antibodies Using a Nano-LC SRM-ILIS Method. Mol. Pharmaceutics. 2013; 10, 1542-1556). The results are shown in FIG. 4B.

The mutations identified in Example 1 as improving the transporter activity of Bbbt0351, a T97A substitution at Kabat position 97, and a T100aD substitution at Kabat position 100a are introduced into Bbbt0241, resulting in a mutated version Bbbt0241m. The modified scFv or IgG versions of Bbbt0241m are then tested for improved transporter activity using the in vitro transcytosis assay described in Example 1.

Example 3: Additional Library Screening for BBB Transporter Molecules

Competitive cell surface selections were performed using mouse brain endothelial (B.End3) cells to identify phage displayed scFvs from additional phage display libraries that compete with, or possess similar binding properties to, Bbbt0241 and FC5. Three naïve libraries were screened. B.End3 cells were punctured with detergent e.g. 2% formaldehyde for 15 min at room temperature followed by the addition of 0.2% triton in PBS and incubated at room temperature for 15 min before spinning cells and washing with PBS, which allowed access to a larger pool of FC5/Bbbt0241 antigen, thereby, creating better conditions for the enrichment of scFvs that bind to the FC5/Bbbt0241 target antigen. Following cell puncturing, the cells were incubated with the previously mentioned phage libraries for 1-2 hours at room temperature. The cells were subsequently washed up to 10 times in PBS to remove all non binding or weakly binding phage particles from the cells. Subsequently, Bbbt0241 hIgG was added to the washed cells and incubated again for 1-2 hours to allow this IgG to bind to the cells and compete off the bound scFvs from the selection. The cells were spun at 2000 rpm and the supernatant taken off and used to infect growing TG1 cells. A number of iterative rounds of competitive elution selections were performed to enrich for those scFvs that bind to the same or similar epitope as Bbbt0241.

Initial screening of the libraries was performed using *E. coli* peripreps as described in Example 1 in the FMAT assay on B.End3 cells to indicate binding of individual clones. Hits from this initial screening were selected and sequenced before unique scFvs being sent for purified protein preparation (HIS-preps) and used in a confirmatory binding FMAT assay.

Bbbt0241, and all of the FC5 derived ScFvs (mimetics and non-mimetics) that were assayed, possessed a unique binding profile whereby they were observed to only bind a subpopulation of cells (usually about 25-30%) at quite discreet punctate binding on the cell surface.

If either Bbbt0241 hIgG1 or FC5-Fc was able to compete, then the fluorescent signal provided by the bound scFv complexes decreased, indicating that that particular scFv competed for cell binding with Bbbt0241/FC5 (termed an FC5 mimetic, FIG. 6A). Initially, ten unique FC5 mimetic scFvs were identified. However, several were ruled out from further characterization due to reduced stability that rendered them unsuitable, as did lack of species cross-reactivity when tested in the FMAT binding assay with other cells e.g. primary rat or cyno macrovascular brain endothelial cells and human D3 brain endothelial cells. The remaining seven scFvs, termed FC5 mimetics, were further characterized: Bbbt0626, Bbbt0727, Bbbt0632, Bbbt0654, Bbbt0726, Bbbt0732, and Bbbt0754. Lead scFvs were converted to IgG1 format using human IgG1-TM—L234F/L235E/P331S (Oganesyan V et al., *Acta Crystallogr. D Biol. Crystallogr.* 2008: 64 (6); 700-704.), and competition FMAT was performed to determine if the IgG versions of these scFvs were able to compete for binding to the surface of the cell with all other FC5—mimetics tested. The seven FC5 mimetics fell into three competition bins: the first group including Bbbt0626 and Bbbt0727, the second group including Bbbt0632 and Bbbt0654, and the third group including Bbbt0726, Bbbt0732, and Bbbt0754 depending on the way that they were able to compete each other.

From the phage peripreps screened, another 15 unique scFvs were identified with binding profiles similar to Bbbt0241, but their binding to B.End3 cells was not competitively inhibited by Bbbt0241 hIgG1 or FC5-Fc (FIG. 6B). Of these, three were found to have acceptable stability, sequence and cross reactivity properties. These scFvs, Bbbt0643, Bbbt0674, and Bbbt0755, were termed FC5-like non-mimetics.

The DNA sequences of the VH and VL regions of these constructs as well as the amino acid sequences of the scFvs, VH, VL, and the various CDRs and frameworks are presented as the SEQ ID NOs shown in Table 2.

TABLE 2

| | BBB Transporter Molecule Sequences | | | | | | | | | | | | | |
|---|---|---|---|---|---|---|---|---|---|---|---|---|---|---|
| | Structure | | | | | | | | | | | | | |
| | Bbbt 0241 | Bbbt 0626 | Bbbt 0632 | Bbbt 0654 | Bbbt 0726 | Bbbt 0727 | Bbbt 0732 | Bbbt 0754 | Bbbt 0674 | Bbbt 0755 | Bbbt 0643 | Bbbt 0351 | Bbbt 0579 | Bbbt 0671 |
| DNA encoding VH region | 1 | 19 | 37 | 55 | 73 | 91 | 109 | 127 | 145 | 163 | 181 | 199 | 208 | |
| VH entire | 2 | 20 | 38 | 56 | 74 | 92 | 110 | 128 | 146 | 164 | 182 | 200 | 209 | 226 |
| VH CDR1 | 3 | 21 | 39 | 57 | 75 | 93 | 111 | 129 | 147 | 165 | 183 | 201 | 210 | |
| VH CDR2 | 4 | 22 | 40 | 58 | 76 | 94 | 112 | 130 | 148 | 166 | 184 | 202 | 211 | |
| VH CDR3 | 5 | 23 | 41 | 59 | 77 | 95 | 113 | 131 | 149 | 167 | 185 | 203 | 212 | |
| VH FW1 | 6 | 24 | 42 | 60 | 78 | 96 | 114 | 132 | 150 | 168 | 186 | 204 | 213 | |
| VH FW2 | 7 | 25 | 43 | 61 | 79 | 97 | 115 | 133 | 151 | 169 | 187 | 205 | 214 | |
| VH FW3 | 8 | 26 | 44 | 62 | 80 | 98 | 116 | 134 | 152 | 170 | 188 | 206 | 215 | |
| VH FW4 | 9 | 27 | 45 | 63 | 81 | 99 | 117 | 135 | 153 | 171 | 189 | 207 | 216 | |
| DNA encoding VL region | 10 | 28 | 46 | 64 | 82 | 100 | 118 | 136 | 154 | 172 | 190 | | 217 | |
| VL entire | 11 | 29 | 47 | 65 | 83 | 101 | 119 | 137 | 155 | 173 | 191 | | 218 | 227 |
| VL CDR1 | 12 | 30 | 48 | 66 | 84 | 102 | 120 | 138 | 156 | 174 | 192 | | 219 | |
| VL CDR2 | 13 | 31 | 49 | 67 | 85 | 103 | 121 | 139 | 157 | 175 | 193 | | 220 | |
| VL CDR3 | 14 | 32 | 50 | 68 | 86 | 104 | 122 | 140 | 158 | 176 | 194 | | 221 | |
| VL FW1 | 15 | 33 | 51 | 69 | 87 | 105 | 123 | 141 | 159 | 177 | 195 | | 222 | |
| VL FW1 | 16 | 34 | 52 | 70 | 88 | 106 | 124 | 142 | 160 | 178 | 196 | | 223 | |
| VL FW3 | 17 | 35 | 53 | 71 | 89 | 107 | 125 | 143 | 161 | 179 | 197 | | 224 | |
| VL FW4 | 18 | 36 | 54 | 72 | 90 | 108 | 126 | 144 | 162 | 180 | 198 | | 225 | |

The lead FC5 mimetic and non-mimetic candidates were converted to hIgG1TM and hIgG1TM+ADC format. Three residues (T289C, A339C & S442C) in the Fc domain were converted to cysteines to allow for attachment of payload (Dimasi N. et al., J. Mol. Biol. 2009; 393; 672-692

In the hIgG1TM format, peptides with chloromethylketone (CMK) reactive groups were attached via thiol chemistry to the cysteine residues at the inter-chain and intra-chain disulphide bonds in the hinge and CH1-CL1 regions of the hIgG1TM.

Example 4: In Vitro Characterization of FC5 Mimetics and FC5-Like Non-Mimetics FC5 mimetics and FC5-like non-mimetics were characterized by additional in vitro and in vivo assays. Hits were tested for thermal stability according to Sypro orange standard methods (Ericsson et al., 2006 Analytical Biochemistry 357 p 289-298), and for sequence liabilities such as possible N-linked or O-linked glycosylation or de-amidation sites. In addition to the testing of the scFv hits for binding to the mouse brain endothelial cell line B.end3 as described in Example 3, the scFvs were tested for internalization into B.end3 cells by the following FMAT method. Internalisation FMAT was performed similarly to the binding FMAT assay as previously described with the following alterations to the protocol: FMAT was performed at 37° C. and the anti-mouse detection antibody is labelled with CypHer5E and performed in Ringer HEPES buffer containing 0.1% BSA. The FC5 mimetics and FC5-like non-mimetics were tested in hIgG format for binding to primary rat brain endothelial cells (RBEC), primary cynomolgus monkey brain endothelial cells, and for binding to human D3 cells.

The results of these assays are shown in Tables 3 and 4.

at the free cysteine residue between the FLAG and 10×HIS tags at the C-terminal end of the scFv. ScFv transport was detected via ELISA, whereby the transported scFv was captured on a 96 well Ni-NTA plate via the HIS tag and the biotin was detected with Europium labelled streptavidin.

Example 5: In Vivo Characterization of FC5 Mimetics and FC5-Like Non-Mimetics Rat Diuresis Model The efficacy of the transporter polypeptides of the disclosure in transporting a payload comprising an analgesic agent across the BBB was demonstrated using a rat diuresis model as follows.

Dynorphins are a class of endogenous opioid peptides that arise from the precursor protein prodynorphin. They exhibit 6-10 times more potency than morphine on a per mole basis, exerting their effects primarily through the κ-opioid receptor (KOR). Dynorphins have been shown to be modulators of pain response: injecting dynorphin peptides into the subarachnoid space of the rat spinal cord produced dose-dependent analgesia, which was partially eliminated by naloxone treatment (Han J S et al., Sci. Sin., Ser. B, Chem. Biol. Agric. Med. Earth Sci. 27(2):169-77. (1984)). Dynorphin peptides are peripherally restricted in animals and cannot cross the BBB. However, a dynorphin peptide coupled to a BBB targeting moiety could be delivered across the BBB after i.v. administration and result in pain relief.

Towards that end, Bbbt0241 (both scFv and IgG format) was expressed, purified and coupled to a Kκ-opioid peptide (dynorphin) (FIG. 5A) by coupling the dynorphin peptide using a chloromethylketone active group on the to a cysteine residue on the Bbbt0241 scFv or hIgG. The scFv-dynorphin conjugates were injected (i.v.) into rats and diuresis mea-

TABLE 3

FC5 Mimetic Leads

| | scFv B.end3 binding | Bbbt0241 IgG competition | scFv B.End3 Internalization | IgG B.end3 binding | IgG RBEC binding | IgG CBEC binding | IgG D3 (Human) Binding | Thermo stability (scFv) | Library |
|---|---|---|---|---|---|---|---|---|---|
| Bbbt0626 | ✓ | ✓ | ✓ | ✓ | ✓ | ✓ | ✓ | ✓ | BMVtrp |
| Bbbt0727 | ✓ | ✓ | ✓ | ✓ | ✓ | ✓ | ✓ | ✓ | BMVtrp |
| Bbbt0632 | ✓ | ✓ | ✓ | ✓ | ✓ | ✓ | ✓ | ✓ | CStrp |
| Bbbt0654 | ✓ | ✓ | ✓ | ✓ | ✓ | ✓ | ✓ | ✓ | DP47 |
| Bbbt0726 | ✓ | ✓ | ✓ | ✓ | ✓ | ✓ | ✓ | ✓ | BMVtrp |
| Bbbt0732 | ✓ | ✓ | ✓ | ✓ | ✓ | ✓ | ✓ | ✓ | DP47 |
| Bbbt0754 | ✓ | ✓ | ✓ | ✓ | ✓ | ✓ | ✓ | ✓ | DP47 |

TABLE 4

FC5 Non-mimetic Leads

| | scFv B.end3 binding | Bbbt0241 IgG competition | scFv B.End3 Internalization | IgG B.end3 binding | IgG RBEC binding | IgG CBEC binding | IgG D3 (human) binding | Thermo stability (scFv) | Library |
|---|---|---|---|---|---|---|---|---|---|
| Bbbt0643 | ✓ | X | ✓ | ✓ | ✓ | ✓ | ✓ | ✓ | DP47 |
| Bbbt0674 | ✓ | X | ✓ | ✓ | ✓ | ✓ | ✓ | ✓ | DP47 |
| Bbbt0755 | ✓ | X | ✓ | ✓ | ✓ | ✓ | ✓ | ✓ | DP47 |

All lead clones (termed Bbbt) were then tested in rat, mouse and bovine transcytosis assays as described (Watson P. M. D. et al., BMC Neuroscience 2013: 14, 59-79; Coisne C. et al., Lab Invest. 2005: 85, 734-746; Dehouck M-P. et al., J. Neurochem. 1990: 54, 1798-1801) as transporting biotinylated purified scFvs. ScFvs were specifically biotinylated sured hourly over a period of 4 hours. The study design is shown in FIG. 5B. If the dynorphin is transported across the BBB then an increase in diuresis is observed. Peripheral administration of dynorphin alone shows no effect. FIG. 5C shows a significant increase in urine output observed upon administration of dynorphin-conjugated Bbbt0241 to rats.

Both scFv and IgG formats for the FC5 mimetics and non-mimetics were tested in the rat diuresis model. FIG. 7A shows a significant increase in urine output upon administration of IgG versions of Bbbt0643, Bbbt0674, Bbbt0754, and Bbbt0654 over vehicle. The IgG compounds were administered at 4 mls per 1 kg body weight. FIG. 7B, FIG. 7C and FIG. 7D show the effect of different doses of Bbbt0626 hIgG as compared to control (doses are shown on graphs in mgs/ml.). The results show that the effect increases with the dose of dynorphin-conjugated Bbbt0626. Subsequent assays demonstrated that all of the FC5 mimetics in Table 3 and all of the FC5 non-mimetics in Table 4 were positive in the diuresis model (data not shown).

Mouse Partial Sciatic Nerve Ligation Model

Neuropathic pain is centrally mediated and therefore a drug must reach the CNS to allow pain relief. A neuropathic pain model has been described (Seltzer Z et al., Pain 43: 205-218 (1990)) whereby the sciatic nerve of one leg of a mouse is partially ligated, resulting in the paw pressure pain threshold on the injured paw being reduced. An analgesic drug will reduce pain if it is able to reach the CNS and paw pressure ratio will become more equal. A schematic of the model is shown in FIG. 8.

The use of IL-1 receptor antagonism as a strategy for relieving neuropathic pain has been demonstrated (Gabay et al, Eur J Pain. 2011 March; 15(3):242-8 (2011). IL-1Ra is a naturally-occurring IL-1 receptor antagonist. The protein does not cross the BBB, and must be delivered intrathecally to achieve pain reduction as measured by the Seltzer model. However, IL-1Ra coupled to a BBB targeting moiety could be delivered across the BBB after i.v. administration and result in pain relief.

To this end Bbbt0241, Bbbt0632, Bbbt0626, and Bbbt0726 (and NIP228 control IgG) were expressed as fusion constructs with IL-1Ra fused to the C-terminus of the heavy chain constant regions via a linker. Construction of any of these fusion proteins from these or similar building blocks is well within the knowledge of a person of ordinary skill in the art. The fusion constructs were expressed in CHO-EBNA cells (Daramola et al., Biotechnol Prog. 2014 30:132-41). according to standard methods, and the resulting proteins were purified by protein-A affinity and gel filtration. The constructs were shown to retain IL1Ra activity in an in vitro assay (data not shown).

Animal subjects underwent surgery on day 0 and were tested for mechanical hyperalgesia on day 7 and day 10 post-operation. Following administration of the IL-1Ra fusion proteins or controls on day 13 post surgery the animals were again tested for mechanical hyperalgesia at 2 hours (some experiments), 4 hours, 1 day, 2 days and 4 days post-dose.

Mechanical hyperalgesia was determined using an analgysemeter (Randall L O et al., Arch Int Pharmacodyn Ther. 111:409-19 (1957)) (Ugo Basile). An increasing force was applied to the dorsal surface of each hind paw in turn until a withdrawal response was observed. The application of force was halted at this point and the weight in grams recorded. Data was expressed as withdrawal threshold in grams for ipsilateral and contralateral paws. Following the establishment of baseline readings mice were divided into 2 groups with approximately equal ipsilateral/contralateral ratios and underwent surgery. Mice were anaesthetized with 3% isoflurane. Following this approximately 1 cm of the left sciatic nerve was exposed by blunt dissection through an incision at the level of the mid-thigh. A suture (10/0 Virgin Silk: Ethicon) was then passed through the dorsal third of the nerve and tied tightly. The incision was closed using glue and the mice were allowed to recover for at least seven days prior to commencement of testing. Sham operated mice underwent the same protocol but following exposure of the nerve the wound was glued and allowed to recover.

Preliminary dose response studies in mice shown that intravenous (i.v.) administration of 40 mg/kg or 100 mg/kg of Bbbt0241 and Bbbt0632-IL-1Ra fusions showed significant analgesia model system (data note shown). FIG. 9 shows that significant analgesia was observed upon i.v. administration of 100 mg/kg of Bbbt0632, Bbbt0626, and Bbbt0726 IL-1Ra fusions, with the effect lasting more than two days post dose. Additional in vivo studies were carried out with the Bbbt0626 IL-1Ra fusion protein. The fusion protein was administered i.v. at 25 mg/kg, 50 mg/kg, and 100 mg/kg demonstrated a statistically significant dose-related effect (FIG. 10). Moreover, a comparison of i.v. administration to subcutaneous (s.c.) administration showed no difference in effect between the two delivery routes (FIGS. 11A and 11B).

Finally, the effect of repeat administrations was studied. In this study, the animals underwent surgery on day 0 and were tested for mechanical hyperalgesia on day 7 and day 10 post-operation. All animals were dosed with either Bbbt0626-IL-1Ra or NIP228-IL-1Ra on day 13, and were tested for mechanical hyperalgesia at 4 hours and 1 day post-dose. Some animals were re-dosed with either Bbbt0626-IL-1Ra or NIP228-IL-1Ra on day 14 and retested 4 hours later. The study was run in two identical halves due to the large number of animals. Animals were then tested up to 4 days post-dose.

The results (from the combined studies) are shown in FIGS. 12A and 12B. In the singe-dosed animals a peak analgesic effect was between at 4 hours and 1 day post dose as in the earlier studies. In the animals that received two doses the levels of analgesia increased further showing peak analgesia at 4 hours after the second dose. The effect remained statistically significant through 4 days after the second dose. In a further study in which the second dose was administered four days after the first dose (day 17), an increased effect was still observed, lasting out to at least 4 days after the second dose (data not shown).

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. An isolated transporter molecule comprising an immunoglobulin polypeptide, wherein the polypeptide comprises an immunoglobulin heavy chain complementarity-determining region-1 (H-CDR1), an immunoglobulin heavy chain complementarity-determining region-2 (H-CDR2), an immunoglobulin heavy chain complementarity-determining region-3 (H-CDR3), an immunoglobulin light chain complementarity-determining region-1 (L-CDR1), an immunoglobulin light chain complementarity-determining region-2 (L-CDR2), and an immunoglobulin light chain complementarity-determining region-3 (L-CDR3); wherein the H-CDR1, H-CDR2, H-CDR3, L-CDR1, L-CDR2, and L-CDR3 comprise, respectively:

(a) SEQ ID NO: 3, SEQ ID NO: 4, SEQ ID NO: 5, SEQ ID NO: 12, SEQ ID NO: 13, and SEQ ID NO: 14;

(b) SEQ ID NO: 21, SEQ ID NO: 22, SEQ ID NO: 23, SEQ ID NO: 229, SEQ ID NO: 230, and SEQ ID NO: 231;

(c) SEQ ID NO: 39, SEQ ID NO: 40, SEQ ID NO: 41, SEQ ID NO: 229, SEQ ID NO: 230, and SEQ ID NO: 231;

(d) SEQ ID NO: 57, SEQ ID NO: 58, SEQ ID NO: 59, SEQ ID NO: 66, SEQ ID NO: 67, and SEQ ID NO: 68;

(e) SEQ ID NO: 75, SEQ ID NO: 76, SEQ ID NO: 77, SEQ ID NO: 229, SEQ ID NO: 230, and SEQ ID NO: 231;

(f) SEQ ID NO: 93, SEQ ID NO: 94, SEQ ID NO: 95, SEQ ID NO: 229, SEQ ID NO: 230, and SEQ ID NO: 231;

(g) SEQ ID NO: 111, SEQ ID NO: 112, SEQ ID NO: 113, SEQ ID NO: 229, SEQ ID NO: 230, and SEQ ID NO: 231;

(h) SEQ ID NO: 129, SEQ ID NO: 130, SEQ ID NO: 131, SEQ ID NO: 138, SEQ ID NO: 139, and SEQ ID NO: 140;
(i) SEQ ID NO: 147, SEQ ID NO: 148, SEQ ID NO: 149, SEQ ID NO: 156, SEQ ID NO: 157, and SEQ ID NO: 158;
(j) SEQ ID NO: 165, SEQ ID NO: 166, SEQ ID NO: 167, SEQ ID NO: 174, SEQ ID NO: 175, and SEQ ID NO: 176;
(k) SEQ ID NO: 183, SEQ ID NO: 184, SEQ ID NO: 185, SEQ ID NO: 192, SEQ ID NO: 193, and SEQ ID NO: 194; or
(l) SEQ ID NO: 210, SEQ ID NO: 211, SEQ ID NO: 212, SEQ ID NO: 219, SEQ ID NO: 220, and SEQ ID NO: 220; and
wherein the transporter molecule can cross the blood brain barrier.

2. The transporter molecule of claim 1, wherein the H-CDR1, H-CDR2, H-CDR3, L-CDR1, L-CDR2, and L-CDR3 comprise, respectively:
(b) SEQ ID NO: 21, SEQ ID NO: 22, SEQ ID NO: 23, SEQ ID NO: 30, SEQ ID NO: 31, and SEQ ID NO: 32;
(c) SEQ ID NO: 39, SEQ ID NO: 40, SEQ ID NO: 41, SEQ ID NO: 48, SEQ ID NO: 49, and SEQ ID NO: 50;
(e) SEQ ID NO: 75, SEQ ID NO: 76, SEQ ID NO: 77, SEQ ID NO: 84, SEQ ID NO: 85, and SEQ ID NO: 86;
(f) SEQ ID NO: 93, SEQ ID NO: 94, SEQ ID NO: 95, SEQ ID NO: 102, SEQ ID NO: 103, and SEQ ID NO: 104;
(g) SEQ ID NO: 111, SEQ ID NO: 112, SEQ ID NO: 113, SEQ ID NO: 120, SEQ ID NO: 121, and SEQ ID NO: 122; or
(h) SEQ ID NO: 129, SEQ ID NO: 130, SEQ ID NO: 131, SEQ ID NO: 138, SEQ ID NO: 139, and SEQ ID NO: 140.

3. The transporter molecule of claim 1, wherein:
(a) the VH comprises SEQ ID NO: 2 and the VL comprises SEQ ID NO: 11;
(b) the VH comprises SEQ ID NO: 20 and the VL comprises SEQ ID NO: 228;
(c) the VH comprises SEQ ID NO: 38 and the VL comprises SEQ ID NO: 228;
(d) the VH comprises SEQ ID NO: 56 and the VL comprises SEQ ID NO: 65;
(e) the VH comprises SEQ ID NO: 74 and the VL comprises SEQ ID NO: 228;
(f) the VH comprises SEQ ID NO: 92 and the VL comprises SEQ ID NO: 228;
(g) the VH comprises SEQ ID NO: 110 and the VL comprises SEQ ID NO: 228;
(h) the VH comprises SEQ ID NO: 128 and the VL comprises SEQ ID NO: 137;
(i) the VH comprises SEQ ID NO: 146 and the VL comprises SEQ ID NO: 155;
(j) the VH comprises SEQ ID NO: 164 and the VL comprises SEQ ID NO: 173;
(k) the VH comprises SEQ ID NO: 182 and the VL comprises SEQ ID NO: 191;
(l) the VH comprises SEQ ID NO: 209 and the VL comprises SEQ ID NO: 218;
(m) the VH comprises SEQ ID NO: 226 and the VL comprises SEQ ID NO: 227;
(n) the VH comprises SEQ ID NO: 20 and the VL comprises SEQ ID NO: 29;
(o) the VH comprises SEQ ID NO: 38 and the VL comprises SEQ ID NO: 47;
(p) the VH comprises SEQ ID NO: 74 and the VL comprises SEQ ID NO: 83;
(q) the VH comprises SEQ ID NO: 92 and the VL comprises SEQ ID NO: 101;
or
(r) the VH comprises SEQ ID NO: 110 and the VL comprises SEQ ID NO: 119.

4. The transporter molecule of claim 1, wherein the immunoglobulin polypeptide comprises an antibody or a BBB-penetrable fragment thereof.

5. The transporter molecule of claim 3, comprising a heavy chain and a light chain associated via disulfide bonds.

6. The transporter molecule of claim 5, wherein the heavy chain constant region of the heavy chain, or fragment thereof is an IgG constant region or fragment thereof, or an Fc region.

7. The transporter molecule of claim 6, wherein
(a) the IgG constant domain or fragment thereof comprises one or more amino acid substitutions relative to a wild-type IgG constant domain wherein the modified IgG has an altered half-life and/or altered binding affinity for FcRn compared to the half-life of an IgG having the wild-type IgG constant domain; or
(b) the IgG constant domain or fragment thereof comprises one or more amino acid substitutions relative to a wild-type IgG constant domain, and wherein the modified IgG has reduced effector function and/or reduced binding to at least one effector molecule compared to the half-life of an IgG having the wild-type IgG constant domain; or
(c) the IgG constant domain or fragment thereof has an altered glycosylation relative to a wild-type IgG constant domain, and wherein the modified IgG has reduced effector function and/or reduced binding to at least one effector molecule compared to the half-life of an IgG having the wild-type IgG constant domain.

8. The transporter molecule of claim 1, wherein (a) the modified IgG has an increased half-life and/or an increased binding affinity for FcRn compared to the half-life of an IgG having the wild-type IgG constant domain; or (b) the modified IgG has a decreased half-life and/or a decreased binding affinity for FcRn compared to the half-life of an IgG having the wild-type IgG constant domain.

9. The transporter molecule of claim 6, further comprising a light chain constant domain or fragment thereof; optionally wherein the light chain constant domain or fragment thereof comprises a human kappa constant domain or fragment thereof, or a human lambda constant region or fragment thereof.

10. The transporter molecule claim 4, which is an Fv fragment, an Fab fragment, an F(ab')2 fragment, an Fab' fragment, a dsFv fragment, a scFv fragment, or an sc(Fv)2 fragment.

11. The transporter molecule of claim 10, comprising (a) a scFv fragment, wherein the scFv comprises a VH and a VL fused together via a linker; or (b) a dsFv fragment, wherein the dsFv comprises a VH and a VL fused together via a linker.

12. The transporter molecule of claim 11, wherein the VH, VL and linker are arranged from the amino terminus: VH-L-VL; optionally wherein the linker is (Gly4Ser)n, where n is a positive integer selected from the group consisting of 1 (SEQ ID NO: 232), 2, 3, 4, 5, 6, 7, 8, 9 and 10, Ser(Gly4Ser)n, where n is a positive integer selected from the group consisting of 1 (SEQ ID NO: 233), 2, 3, 4, 5, 6, 7, 8, 9 and 10, GGGGSGGGGSGGGGS (SEQ ID NO: 234), GGGGSGGGGSGGGG (SEQ ID NO: 235), GGGGSGGGGSGGGGSAL (SEQ ID NO: 236), or GGGGSGGGGSGGGGSA (SEQ ID NO: 237).

13. The transporter molecule of claim 1, further comprising an associated payload, wherein the transporter molecule can transport the payload across the BBB.

14. The transporter molecule of claim 13, wherein the payload (a) is fused, via a peptide bond, to the immunoglobulin-derived polypeptide; (b) is chemically conjugated to the immunoglobulin-derived polypeptide; or (c) is associated with the immunoglobulin-derived polypeptide via non-covalent bonds.

15. The transporter molecule of claim 13, wherein
   (a) the payload comprises an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a polyethylene glycol (PEG) molecule, or a combination of two or more of the agents;
   (b) the payload comprises a neuroactive polypeptide selected from the group consisting of: neurotrophic factors, endocrine factors, growth factors, paracrine factors, hypothalamic release factors, neurotransmitter polypeptides, polypeptide agonists for a receptor expressed by a CNS cell, and polypeptides involved in lysosomal storage disease; or
   (c) the payload comprises an IL-1 receptor antagonist (IL-1Ra), dalargin, an interferon-β, Glial-derived neurotrophic factor (GDNF), tumor necrosis factor receptor (TNFR), nerve growth factor (NGF), brain derived neurotrophic factor (BDNF), neurotrophin-4/5, neurotrophin (NT)-3, a neurturin, neuregulin, a netrin, ciliary neurotrophic factor (CNTF), stem cell factor (SCF), a semaphorin, hepatocyte growth factor (HGF), epidermal growth factor (EGF), transforming growth factor (TGF)-cx, TGF-B, vascular endothelial growth factor (VEGF), platelet-derived growth factor (PDGF), heregulin, artemin, persephin, interleukins, granulocyte-colony stimulating factor (CSF), granulocyte-macrophage-CSF, cardiotrophin-1, hedgehogs, leukemia inhibitory factor (LIF), midkine, pleiotrophin, erythropoietin (EPO), bone morphogenetic proteins (BMPs), netrins, saposins, any fragment thereof, or any combination thereof.

16. The transporter molecule of claim 15, wherein the payload comprises a heterologous antibody or fragment thereof.

17. The transporter molecule of claim 16, wherein the heterologous antibody or fragment thereof specifically binds to beta-secretase 1 (BACE1), CD20, CD25, CD52, CD33, CTLA-4, tenascin, alpha-4 (a4) integrin, IL-12, IL-23, the p40 subunit of IL-12/IL-23, amyloid-13 (AI3), Huntingtin, nerve growth factor (NGF), epidermal growth factor receptor (EGFR/HER1), human epidermal growth factor receptor 2 (HER2/neu), vascular endothelial growth factor (VEGF), TrkA, TNF-a, TNF-13, α-synuclein, Tau, apolipoprotein E4 (ApoE4), prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), caspase 6, a neurotrophic factor or a neurotrophic factor receptor.

18. The transporter molecule of claim 1, wherein the transporter molecule binds to human, cynomolgus monkey, murine, rat, or bovine brain microvascular endothelial cells (BMVECs).

19. A composition comprising the transporter molecule of claim 1, and a carrier.

20. An isolated polynucleotide comprising a nucleic acid molecule encoding the transporter molecule of claim 1, or a BBB-penetrable fragment of said transporter molecule, wherein said transporter molecule or fragment comprises the H-CDR1, H-CDR2, H-CDR3, L-CDR1, L-CDR2, and L-CDR3 of claim 1.

21. The isolated polynucleotide of claim 20, further comprising a nucleic acid that encodes a payload.

22. A vector comprising the isolated polynucleotide of claim 21.

23. An isolated host cell comprising the vector of claim 22.

24. A method of making an isolated transporter molecule comprising an immunoglobulin polypeptide, wherein the polypeptide comprises an immunoglobulin heavy chain complementarity-determining region-and 1 (H-CDR1), an immunoglobulin heavy chain complementarity-determining region-2 (H-CDR2), an immunoglobulin heavy chain complementarity-determining region-3 (H-CDR3), an immunoglobulin light chain complementarity-determining region-1 (L-CDR1), an immunoglobulin light chain complementarity-determining region-2 (L-CDR2), and an immunoglobulin light chain complementarity-determining region-3 (L-CDR3); wherein the H-CDR1, H-CDR2, H-CDR3, L-CDR1, L-CDR2, and L-CDR3 comprise, respectively:
   (a) SEQ ID NO: 3, SEQ ID NO: 4, SEQ ID NO: 5, SEQ ID NO: 12, SEQ ID NO: 13, and SEQ ID NO: 14;
   (b) SEQ ID NO: 21, SEQ ID NO: 22, SEQ ID NO: 23, SEQ ID NO: 229, SEQ ID NO: 230, and SEQ ID NO: 231;
   (c) SEQ ID NO: 39, SEQ ID NO: 40, SEQ ID NO: 41, SEQ ID NO: 229, SEQ ID NO: 230, and SEQ ID NO: 231;
   (d) SEQ ID NO: 57, SEQ ID NO: 58, SEQ ID NO: 59, SEQ ID NO: 66, SEQ ID NO: 67, and SEQ ID NO: 68;
   (e) SEQ ID NO: 75, SEQ ID NO: 76, SEQ ID NO: 77, SEQ ID NO: 229, SEQ ID NO: 230, and SEQ ID NO: 231;
   (f) SEQ ID NO: 93, SEQ ID NO: 94, SEQ ID NO: 95, SEQ ID NO: 229, SEQ ID NO: 230, and SEQ ID NO: 231;
   (g) SEQ ID NO: 111, SEQ ID NO: 112, SEQ ID NO: 113, SEQ ID NO: 229, SEQ ID NO: 230, and SEQ ID NO: 231;
   (h) SEQ ID NO: 129, SEQ ID NO: 130, SEQ ID NO: 131, SEQ ID NO: 138, SEQ ID NO: 139, and SEQ ID NO: 140;
   (i) SEQ ID NO: 147, SEQ ID NO: 148, SEQ ID NO: 149, SEQ ID NO: 156, SEQ ID NO: 157, and SEQ ID NO: 158;
   (j) SEQ ID NO: 165, SEQ ID NO: 166, SEQ ID NO: 167, SEQ ID NO: 174, SEQ ID NO: 175, and SEQ ID NO: 176;
   (k) SEQ ID NO: 183, SEQ ID NO: 184, SEQ ID NO: 185, SEQ ID NO: 192, SEQ ID NO: 193, and SEQ ID NO: 194; or
   (l) SEQ ID NO: 210, SEQ ID NO: 211, SEQ ID NO: 212, SEQ ID NO: 219, SEQ ID NO: 220, and SEQ ID NO: 220; and
wherein the transporter molecule can cross the blood brain barrier,
the method comprising (a) culturing the host cell of claim 23; and (b) isolating the transporter molecule or fragment or subunit thereof.

25. The method of claim 24, further comprising (c) conjugating the transporter molecule or fragment or subunit thereof to a payload.

26. A method of increasing the exposure of the CNS of a subject to an agent comprising coupling the agent to the transporter molecule of claim 1 and peripherally administering the coupled agent.

27. A method of transporting an agent across the BBB comprising coupling the agent to the transporter molecule of claim 1 such that the transporter molecule transports the agent coupled thereto across the BBB.

* * * * *

SEQUENCE LISTING

<160> NUMBER OF SEQ ID NOS: 237

<210> SEQ ID NO 1
<211> LENGTH: 366
<212> TYPE: DNA
<213> ORGANISM: Homo sapiens
<220> FEATURE:
<223> OTHER INFORMATION: Bbbt0241 VH

<400> SEQUENCE: 1

```
gaagttcaac tgcaggcgtc cggcggtggc ctggtgcagg ctggcggctc tctgcgtctg      60
tcctgtgctg ccagcggctt taaaatcact cactatacta tgggctggtt ccgccaggca     120
ccgggcaaag agcgtgaatt cgtgagccgc atcacctggg gcggtgacaa caccttttac     180
tccaactccg ttaagggtcg ttttactatc tctcgtgata cgctaaaaa caccgtttac      240 ctgcagatga acagcctgaa accagaggac actgctgact actattgtgc tgcaggttcc     300
acctctacgg ctaccccact gcgcgtcgac tattggggca aaggcaccca ggtgaccgtc     360
tcgagt                                                               366
```

<210> SEQ ID NO 2
<211> LENGTH: 122
<212> TYPE: PRT
<213> ORGANISM: Homo sapiens
<220> FEATURE:
<223> OTHER INFORMATION: Bbbt0241 VH

<400> SEQUENCE: 2

Glu Val Gln Leu Gln Ala Ser Gly Gly Gly Leu Val Gln Ala Gly Gly
                5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Ser Thr Ala Thr Pro Leu Arg Val Asp Tyr Trp
            100                 105                 110

Gly Lys Gly Thr Gln Val Thr Val Ser Ser
        115                 120

<210> SEQ ID NO 3
<211> LENGTH: 5
<212> TYPE: PRT
<213> ORGANISM: Homo sapiens
<220> FEATURE:
<223> OTHER INFORMATION: Bbbt0241 VH CDR1

<400> SEQUENCE: 3

His Tyr Thr Met Gly
                5

<210> SEQ ID NO 4
<211> LENGTH: 17
<212> TYPE: PRT
<213> ORGANISM: Homo sapiens
<220> FEATURE:

<223> OTHER INFORMATION: Bbbt0241 VH CDR2

<400> SEQUENCE: 4

Arg Ile Thr Trp Gly Gly Asp Asn Thr Phe Tyr Ser Asn Ser Val Lys
                5                   10                  15
Gly

<210> SEQ ID NO 5
<211> LENGTH: 13
<212> TYPE: PRT
<213> ORGANISM: Homo sapiens
<220> FEATURE:
<223> OTHER INFORMATION: Bbbt0241 VH CDR3

<400> SEQUENCE: 5

Gly Ser Thr Ser Thr Ala Thr Pro Leu Arg Val Asp Tyr
                5                   10

<210> SEQ ID NO 6
<211> LENGTH: 30
<212> TYPE: PRT
<213> ORGANISM: Homo sapiens
<220> FEATURE:
<223> OTHER INFORMATION: Bbbt0241 VH FW1

<400> SEQUENCE: 6

Glu Val Gln Leu Gln Ala Ser Gly Gly Gly Leu Val Gln Ala Gly Gly
                5                   10                  15
Ser Leu Arg Leu Ser Cys Ala Ala Ser Gly Phe Lys Ile Thr
            20                  25                  30

<210> SEQ ID NO 7
<211> LENGTH: 14
<212> TYPE: PRT
<213> ORGANISM: Homo sapiens
<220> FEATURE:
<223> OTHER INFORMATION: Bbbt0241 VH FW2

<400> SEQUENCE: 7

Trp Phe Arg Gln Ala Pro Gly Lys Glu Arg Glu Phe Val Ser
                5                   10

<210> SEQ ID NO 8
<211> LENGTH: 32
<212> TYPE: PRT
<213> ORGANISM: Homo sapiens
<220> FEATURE:
<223> OTHER INFORMATION: Bbbt0241 VH FW3

<400> SEQUENCE: 8

Arg Phe Thr Ile Ser Arg Asp Asn Ala Lys Asn Thr Val Tyr Leu Gln
                5                   10                  15
Met Asn Ser Leu Lys Pro Glu Asp Thr Ala Asp Tyr Tyr Cys Ala Ala
            20                  25                  30

<210> SEQ ID NO 9
<211> LENGTH: 11
<212> TYPE: PRT
<213> ORGANISM: Homo sapiens
<220> FEATURE:
<223> OTHER INFORMATION: Bbbt0241 VH FW4

<400> SEQUENCE: 9

Trp Gly Lys Gly Thr Gln Val Thr Val Ser Ser
                5                   10

<210> SEQ ID NO 10
<211> LENGTH: 324
<212> TYPE: DNA
<213> ORGANISM: Homo sapiens
<220> FEATURE:
<223> OTHER INFORMATION: Bbbt0241 VL

<400> SEQUENCE: 10

```
gaaacgacac tcacgcagtc tccagacacc ctgtctttgt ctccagggga aagagccacc      60
ctctcctgcc gggccagtca gagtcttagc aacaacttct tagcctggta ccagcagaaa    120
tctggccagg ctcccaggct cctcatctat gctgcatcca gcagggccac tggcatccca    180
gacagattca gtggcagtgg gtctgggaca gacttcactc tcaccatcag cagactggag    240
cctgaagatt ttgcagttta ttactgtcag cagtatgctg cctcagcgat caccttcggc    300
caagggacac gactggagat taaa                                            324
```

<210> SEQ ID NO 11
<211> LENGTH: 108
<212> TYPE: PRT
<213> ORGANISM: Homo sapiens
<220> FEATURE:
<223> OTHER INFORMATION: Bbbt0241 VL

<400> SEQUENCE: 11

Glu Thr Thr Leu Thr Gln Ser Pro Asp Thr Leu Ser Leu Ser Pro Gly
1               5                   10                  15

Glu Arg Ala Thr Leu Ser Cys Arg Ala Ser Gln Ser Leu Ser Asn Asn
            20                  25                  30

Phe Leu Ala Trp Tyr Gln Gln Lys Ser Gly Gln Ala Pro Arg Leu Leu
        35                  40                  45

Ile Tyr Ala Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Ala Ser Ala
                85                  90                  95

Ile Thr Phe Gly Gln Gly Thr Arg Leu Glu Ile Lys
            100                 105

<210> SEQ ID NO 12
<211> LENGTH: 12
<212> TYPE: PRT
<213> ORGANISM: Homo sapiens
<220> FEATURE:
<223> OTHER INFORMATION: Bbbt0241 VL CDR1

<400> SEQUENCE: 12

Arg Ala Ser Gln Ser Leu Ser Asn Asn Phe Leu Ala
1               5                   10

<210> SEQ ID NO 13
<211> LENGTH: 7
<212> TYPE: PRT
<213> ORGANISM: Homo sapiens
<220> FEATURE:
<223> OTHER INFORMATION: Bbbt0241 VL CDR2

<400> SEQUENCE: 13

Ala Ala Ser Ser Arg Ala Thr
1               5

```
<210> SEQ ID NO 14
<211> LENGTH: 9
<212> TYPE: PRT
<213> ORGANISM: Homo sapiens
<220> FEATURE:
<223> OTHER INFORMATION: Bbbt0241 VL CDR3

<400> SEQUENCE: 14

Gln Gln Tyr Ala Ala Ser Ala Ile Thr
                5

<210> SEQ ID NO 15
<211> LENGTH: 23
<212> TYPE: PRT
<213> ORGANISM: Homo sapiens
<220> FEATURE:
<223> OTHER INFORMATION: Bbbt0241 VL FW1

<400> SEQUENCE: 15

Glu Thr Thr Leu Thr Gln Ser Pro Asp Thr Leu Ser Leu Ser Pro Gly
                5                  10                  15

Glu Arg Ala Thr Leu Ser Cys
            20

<210> SEQ ID NO 16
<211> LENGTH: 15
<212> TYPE: PRT
<213> ORGANISM: Homo sapiens
<220> FEATURE:
<223> OTHER INFORMATION: Bbbt0241 VL FW2

<400> SEQUENCE: 16

Trp Tyr Gln Gln Lys Ser Gly Gln Ala Pro Arg Leu Leu Ile Tyr
                5                  10                  15

<210> SEQ ID NO 17
<211> LENGTH: 32
<212> TYPE: PRT
<213> ORGANISM: Homo sapiens
<220> FEATURE:
<223> OTHER INFORMATION: Bbbt0241 VL FW3

<400> SEQUENCE: 17

Gly Ile Pro Asp Arg Phe Ser Gly Ser Gly Ser Gly Thr Asp Phe Thr
                5                  10                  15

Leu Thr Ile Ser Arg Leu Glu Pro Glu Asp Phe Ala Val Tyr Tyr Cys
            20                  25                  30

<210> SEQ ID NO 18
<211> LENGTH: 10
<212> TYPE: PRT
<213> ORGANISM: Homo sapiens
<220> FEATURE:
<223> OTHER INFORMATION: Bbbt0241 VL FW4

<400> SEQUENCE: 18

Phe Gly Gln Gly Thr Arg Leu Glu Ile Lys
                5                  10

<210> SEQ ID NO 19
<211> LENGTH: 369
<212> TYPE: DNA
<213> ORGANISM: Homo sapiens
<220> FEATURE:
<223> OTHER INFORMATION: Bbbt0626 VH
```

<400> SEQUENCE: 19

```
ggggtccagc tggtgcagtc tggggcagag ctgaagaagc ctgggtcctc ggtgaaggtc      60
tcctgtaagg cttctggagg caccttcagc agttatgcta tcagctgggt gcgacaggcc     120
cctggacaag gcttgagtg gatgggaagg atcatcccta ttcttggtac atcaaactac     180
gcacagaagt tccagggcag agtcacgatt accgcggacg aacgtacgag cacagcctac     240
atggagctga gcagcctgag atctgaggac acggccgtat attactgtgc gagaaggagt     300
agtttagcag cagcggatag ggggctttt gatatctggg gccaggggac aatggtcacc     360
gtctcgagt                                                             369
```

<210> SEQ ID NO 20
<211> LENGTH: 123
<212> TYPE: PRT
<213> ORGANISM: Homo sapiens
<220> FEATURE:
<223> OTHER INFORMATION: Bbbt0626 VH

<400> SEQUENCE: 20

```
Gly Val Gln Leu Val Gln Ser Gly Ala Glu Leu Lys Lys Pro Gly Ser
                 5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Thr Ser Asn Tyr Ala Gln Lys Phe
    50                  55                  60

Gln Gly Arg Val Thr Ile Thr Ala Asp Glu Arg Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ser Ser Leu Ala Ala Ala Asp Arg Gly Ala Phe Asp Ile
            100                 105                 110

Trp Gly Gln Gly Thr Met Val Thr Val Ser Ser
        115                 120
```

<210> SEQ ID NO 21
<211> LENGTH: 5
<212> TYPE: PRT
<213> ORGANISM: Homo sapiens
<220> FEATURE:
<223> OTHER INFORMATION: Bbbt0626 VH CDR1

<400> SEQUENCE: 21

```
Ser Tyr Ala Ile Ser
                 5
```

<210> SEQ ID NO 22
<211> LENGTH: 17
<212> TYPE: PRT
<213> ORGANISM: Homo sapiens
<220> FEATURE:
<223> OTHER INFORMATION: Bbbt0626 VH CDR2

<400> SEQUENCE: 22

```
Arg Ile Ile Pro Ile Leu Gly Thr Ser Asn Tyr Ala Gln Lys Phe Gln
                 5                  10                  15

Gly
```

<210> SEQ ID NO 23
<211> LENGTH: 14
<212> TYPE: PRT
<213> ORGANISM: Homo sapiens
<220> FEATURE:
<223> OTHER INFORMATION: Bbbt0626 VH CDR3

<400> SEQUENCE: 23

Arg Ser Ser Leu Ala Ala Ala Asp Arg Gly Ala Phe Asp Ile
                5                  10

<210> SEQ ID NO 24
<211> LENGTH: 30
<212> TYPE: PRT
<213> ORGANISM: Homo sapiens
<220> FEATURE:
<223> OTHER INFORMATION: Bbbt0626  VH FW1

<400> SEQUENCE: 24

Gly Val Gln Leu Val Gln Ser Gly Ala Glu Leu Lys Lys Pro Gly Ser
                5                  10                  15

Ser Val Lys Val Ser Cys Lys Ala Ser Gly Gly Thr Phe Ser
            20                  25                  30

<210> SEQ ID NO 25
<211> LENGTH: 14
<212> TYPE: PRT
<213> ORGANISM: Homo sapiens
<220> FEATURE:
<223> OTHER INFORMATION: Bbbt0626  VH FW2

<400> SEQUENCE: 25

Trp Val Arg Gln Ala Pro Gly Gln Gly Leu Glu Trp Met Gly
                5                  10

<210> SEQ ID NO 26
<211> LENGTH: 32
<212> TYPE: PRT
<213> ORGANISM: Homo sapiens
<220> FEATURE:
<223> OTHER INFORMATION: Bbbt0626  VH FW3

<400> SEQUENCE: 26

Arg Val Thr Ile Thr Ala Asp Glu Arg Thr Ser Thr Ala Tyr Met Glu
                5                  10                  15

Leu Ser Ser Leu Arg Ser Glu Asp Thr Ala Val Tyr Tyr Cys Ala Arg
            20                  25                  30

<210> SEQ ID NO 27
<211> LENGTH: 11
<212> TYPE: PRT
<213> ORGANISM: Homo sapiens
<220> FEATURE:
<223> OTHER INFORMATION: Bbbt0626  VH FW4

<400> SEQUENCE: 27

Trp Gly Gln Gly Thr Met Val Thr Val Ser Ser
                5                  10

<210> SEQ ID NO 28
<211> LENGTH: 324
<212> TYPE: DNA
<213> ORGANISM: Homo sapiens
<220> FEATURE:
<223> OTHER INFORMATION: Bbbt0626  VL

<400> SEQUENCE: 28

```
tcgtctgagc tgactcagga ccctgctgtg tctgtggcct tgggacagac agtcaggatc    60
acatgccaag gagacagcct cagaagctat atgcaagct ggtaccagca aaagccagga   120
caggcccctg tacttgtcat ctatggtaaa acaaccggc cctcagggat cccagaccga   180
ttctctggct ccagctcagg aaacacagct tccttgacca tcactggggc tcaggcggaa   240
gatgaggctg actattactg taactcccgg gacagcagtg gtaaccatgt ggtattcggc   300
ggagggacca agctgaccgt ccta                                          324
```

<210> SEQ ID NO 29
<211> LENGTH: 108
<212> TYPE: PRT
<213> ORGANISM: Homo sapiens
<220> FEATURE:
<223> OTHER INFORMATION: Bbbt0626 VL

<400> SEQUENCE: 29

```
Ser Ser Glu Leu Thr Gln Asp Pro Ala Val Ser Val Ala Leu Gly Gln
                 5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Val Val Phe Gly Gly Gly Thr Lys Leu Thr Val Leu
            100                 105
```

<210> SEQ ID NO 30
<211> LENGTH: 11
<212> TYPE: PRT
<213> ORGANISM: Homo sapiens
<220> FEATURE:
<223> OTHER INFORMATION: Bbbt0626 VL CDR1

<400> SEQUENCE: 30

```
Gln Gly Asp Ser Leu Arg Ser Tyr Tyr Ala Ser
                 5                  10
```

<210> SEQ ID NO 31
<211> LENGTH: 7
<212> TYPE: PRT
<213> ORGANISM: Homo sapiens
<220> FEATURE:
<223> OTHER INFORMATION: Bbbt0626 VL CDR2

<400> SEQUENCE: 31

```
Gly Lys Asn Asn Arg Pro Ser
                 5
```

<210> SEQ ID NO 32
<211> LENGTH: 11
<212> TYPE: PRT
<213> ORGANISM: Homo sapiens
<220> FEATURE:
<223> OTHER INFORMATION: Bbbt0626 VL CDR3

<400> SEQUENCE: 32

Asn Ser Arg Asp Ser Ser Gly Asn His Val Val
                5                   10

<210> SEQ ID NO 33
<211> LENGTH: 22
<212> TYPE: PRT
<213> ORGANISM: Homo sapiens
<220> FEATURE:
<223> OTHER INFORMATION: Bbbt0626 VL FW1

<400> SEQUENCE: 33

Ser Ser Glu Leu Thr Gln Asp Pro Ala Val Ser Val Ala Leu Gly Gln
                5                   10                  15

Thr Val Arg Ile Thr Cys
            20

<210> SEQ ID NO 34
<211> LENGTH: 15
<212> TYPE: PRT
<213> ORGANISM: Homo sapiens
<220> FEATURE:
<223> OTHER INFORMATION: Bbbt0626 VL FW2

<400> SEQUENCE: 34

Trp Tyr Gln Gln Lys Pro Gly Gln Ala Pro Val Leu Val Ile Tyr
                5                   10                  15

<210> SEQ ID NO 35
<211> LENGTH: 32
<212> TYPE: PRT
<213> ORGANISM: Homo sapiens
<220> FEATURE:
<223> OTHER INFORMATION: Bbbt0626 VL FW3

<400> SEQUENCE: 35

Gly Ile Pro Asp Arg Phe Ser Gly Ser Ser Ser Gly Asn Thr Ala Ser
                5                   10                  15

Leu Thr Ile Thr Gly Ala Gln Ala Glu Asp Glu Ala Asp Tyr Tyr Cys
            20                  25                  30

<210> SEQ ID NO 36
<211> LENGTH: 10
<212> TYPE: PRT
<213> ORGANISM: Homo sapiens
<220> FEATURE:
<223> OTHER INFORMATION: Bbbt0626 VL FW4

<400> SEQUENCE: 36

Phe Gly Gly Gly Thr Lys Leu Thr Val Leu
                5                   10

<210> SEQ ID NO 37
<211> LENGTH: 366
<212> TYPE: DNA
<213> ORGANISM: Homo sapiens
<220> FEATURE:
<223> OTHER INFORMATION: Bbbt0632 VH

<400> SEQUENCE: 37
caggtgcagc tggtgcagtc tggggctgag gtgaagaagc ctgggtcctc ggtgaaggtc      60
tcctgcaaga cttctggagg caccttcggc acctattcta tcacctgggt gcgacaggcc     120
cctggacaag ggcttgagtg gatgggagac atcgtcccta tctttggaac accaaactac     180

```
gcacagaatt tccagggcag agtcactatc tccgcggacg tatccacggc gacagtctac    240
atggagctga gcagcctaac atccgacgac acggccgtct acttctgtgc taagaggggg    300
agttactacg gccggggagg ttggttcgac ccctgggccg ggggacaatg gtcaccgtc    360 tcgagt                                                               366
```

<210> SEQ ID NO 38
<211> LENGTH: 122
<212> TYPE: PRT
<213> ORGANISM: Homo sapiens
<220> FEATURE:
<223> OTHER INFORMATION: Bbbt0632 VH

<400> SEQUENCE: 38

Gln Val Gln Leu Val Gln Ser Gly Ala Glu Val Lys Lys Pro Gly Ser
             5                  10                  15

Ser Val Lys Val Ser Cys Lys Thr Ser Gly Gly Thr Phe Gly Thr Tyr
         20                  25                  30

Ser Ile Thr Trp Val Arg Gln Ala Pro Gly Gln Gly Leu Glu Trp Met
     35                  40                  45

Gly Asp Ile Val Pro Ile Phe Gly Thr Pro Asn Tyr Ala Gln Asn Phe
 50                  55                  60

Gln Gly Arg Val Thr Ile Ser Ala Asp Val Ser Thr Ala Thr Val Tyr
65                  70                  75                  80

Met Glu Leu Ser Ser Leu Thr Ser Asp Asp Thr Ala Val Tyr Phe Cys
                 85                  90                  95

Ala Lys Arg Gly Ser Tyr Tyr Gly Arg Gly Gly Trp Phe Asp Pro Trp
            100                 105                 110

Gly Arg Gly Thr Met Val Thr Val Ser Ser
        115                 120

<210> SEQ ID NO 39
<211> LENGTH: 5
<212> TYPE: PRT
<213> ORGANISM: Homo sapiens
<220> FEATURE:
<223> OTHER INFORMATION: Bbbt0632 VH CDR1

<400> SEQUENCE: 39

Thr Tyr Ser Ile Thr
             5

<210> SEQ ID NO 40
<211> LENGTH: 17
<212> TYPE: PRT
<213> ORGANISM: Homo sapiens
<220> FEATURE:
<223> OTHER INFORMATION: Bbbt0632 VH CDR2

<400> SEQUENCE: 40

Asp Ile Val Pro Ile Phe Gly Thr Pro Asn Tyr Ala Gln Asn Phe Gln
             5                  10                  15

Gly

<210> SEQ ID NO 41
<211> LENGTH: 13
<212> TYPE: PRT
<213> ORGANISM: Homo sapiens
<220> FEATURE:
<223> OTHER INFORMATION: Bbbt0632 VH CDR3

<400> SEQUENCE: 41

Arg Gly Ser Tyr Tyr Gly Arg Gly Gly Trp Phe Asp Pro
                5                   10

<210> SEQ ID NO 42
<211> LENGTH: 30
<212> TYPE: PRT
<213> ORGANISM: Homo sapiens
<220> FEATURE:
<223> OTHER INFORMATION: Bbbt0632 VH FW1

<400> SEQUENCE: 42

Gln Val Gln Leu Val Gln Ser Gly Ala Glu Val Lys Lys Pro Gly Ser
                5                   10                  15

Ser Val Lys Val Ser Cys Lys Thr Ser Gly Gly Thr Phe Gly
            20                  25                  30

<210> SEQ ID NO 43
<211> LENGTH: 14
<212> TYPE: PRT
<213> ORGANISM: Homo sapiens
<220> FEATURE:
<223> OTHER INFORMATION: Bbbt0632 VH FW2

<400> SEQUENCE: 43

Trp Val Arg Gln Ala Pro Gly Gln Gly Leu Glu Trp Met Gly
                5                   10

<210> SEQ ID NO 44
<211> LENGTH: 32
<212> TYPE: PRT
<213> ORGANISM: Homo sapiens
<220> FEATURE:
<223> OTHER INFORMATION: Bbbt0632 VH FW3

<400> SEQUENCE: 44

Arg Val Thr Ile Ser Ala Asp Val Ser Thr Ala Thr Val Tyr Met Glu
                5                   10                  15

Leu Ser Ser Leu Thr Ser Asp Asp Thr Ala Val Tyr Phe Cys Ala Lys
            20                  25                  30

<210> SEQ ID NO 45
<211> LENGTH: 11
<212> TYPE: PRT
<213> ORGANISM: Homo sapiens
<220> FEATURE:
<223> OTHER INFORMATION: Bbbt0632 VH FW4

<400> SEQUENCE: 45

Trp Gly Arg Gly Thr Met Val Thr Val Ser Ser
                5                   10

<210> SEQ ID NO 46
<211> LENGTH: 324
<212> TYPE: DNA
<213> ORGANISM: Homo sapiens
<220> FEATURE:
<223> OTHER INFORMATION: Bbbt0632 VL

<400> SEQUENCE: 46
tcttctgagc tgactcagga ccctgctgtg tctgtggcct tgagacagac agtcaggatc    60
acatgccaag agacagcct cacaaggtat tatacaaact ggtaccagca gaagccagga   120
caggccccta tacttgtcat ctatggtgaa acaaccggc cctcagggat cccagaccga   180
ttctctggct ccagatcagg aaacacagct tccttgacca tcactggggc tcaggcggaa   240
gatgaggctg actattactg taactcccgg gacaatactg gtaaacattg ggtgttcggc    300
ggagggacca agctgaccgt ccta    324

<210> SEQ ID NO 47
<211> LENGTH: 108
<212> TYPE: PRT
<213> ORGANISM: Homo sapiens
<220> FEATURE:
<223> OTHER INFORMATION: Bbbt0632 VL

<400> SEQUENCE: 47

Ser Ser Glu Leu Thr Gln Asp Pro Ala Val Ser Val Ala Leu Arg Gln
1               5                   10                  15

Thr Val Arg Ile Thr Cys Gln Gly Asp Ser Leu Thr Arg Tyr Tyr Thr
            20                  25                  30

Asn Trp Tyr Gln Gln Lys Pro Gly Gln Ala Pro Ile Leu Val Ile Tyr
        35                  40                  45

Gly Glu Asn Asn Arg Pro Ser Gly Ile Pro Asp Arg Phe Ser Gly Ser
    50                  55                  60

Arg Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Asn Thr Gly Lys His
                85                  90                  95

Trp Val Phe Gly Gly Gly Thr Lys Leu Thr Val Leu
            100                 105

<210> SEQ ID NO 48
<211> LENGTH: 11
<212> TYPE: PRT
<213> ORGANISM: Homo sapiens
<220> FEATURE:
<223> OTHER INFORMATION: Bbbt0632 VL CDR1

<400> SEQUENCE: 48

Gln Gly Asp Ser Leu Thr Arg Tyr Tyr Thr Asn
1               5                   10

<210> SEQ ID NO 49
<211> LENGTH: 7
<212> TYPE: PRT
<213> ORGANISM: Homo sapiens
<220> FEATURE:
<223> OTHER INFORMATION: Bbbt0632 VL CDR2

<400> SEQUENCE: 49

Gly Glu Asn Asn Arg Pro Ser
1               5

<210> SEQ ID NO 50
<211> LENGTH: 11
<212> TYPE: PRT
<213> ORGANISM: Homo sapiens
<220> FEATURE:
<223> OTHER INFORMATION: Bbbt0632 VL CDR3

<400> SEQUENCE: 50

Asn Ser Arg Asp Asn Thr Gly Lys His Trp Val
1               5                   10

<210> SEQ ID NO 51
<211> LENGTH: 22
<212> TYPE: PRT

<213> ORGANISM: Homo sapiens
<220> FEATURE:
<223> OTHER INFORMATION: Bbbt0632 VL FW1

<400> SEQUENCE: 51

Ser Ser Glu Leu Thr Gln Asp Pro Ala Val Ser Val Ala Leu Arg Gln
1               5                   10                  15
Thr Val Arg Ile Thr Cys
            20

<210> SEQ ID NO 52
<211> LENGTH: 15
<212> TYPE: PRT
<213> ORGANISM: Homo sapiens
<220> FEATURE:
<223> OTHER INFORMATION: Bbbt0632 VL FW2

<400> SEQUENCE: 52

Trp Tyr Gln Gln Lys Pro Gly Gln Ala Pro Ile Leu Val Ile Tyr
1               5                   10                  15

<210> SEQ ID NO 53
<211> LENGTH: 32
<212> TYPE: PRT
<213> ORGANISM: Homo sapiens
<220> FEATURE:
<223> OTHER INFORMATION: Bbbt0632 VL FW3

<400> SEQUENCE: 53

Gly Ile Pro Asp Arg Phe Ser Gly Ser Arg Ser Gly Asn Thr Ala Ser
1               5                   10                  15
Leu Thr Ile Thr Gly Ala Gln Ala Glu Asp Glu Ala Asp Tyr Tyr Cys
            20                  25                  30

<210> SEQ ID NO 54
<211> LENGTH: 10
<212> TYPE: PRT
<213> ORGANISM: Homo sapiens
<220> FEATURE:
<223> OTHER INFORMATION: Bbbt0632 VL FW4

<400> SEQUENCE: 54

Phe Gly Gly Gly Thr Lys Leu Thr Val Leu
1               5                   10

<210> SEQ ID NO 55
<211> LENGTH: 384
<212> TYPE: DNA
<213> ORGANISM: Homo sapiens
<220> FEATURE:
<223> OTHER INFORMATION: Bbbt0654 VH

<400> SEQUENCE: 55
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggccgtgt attactgtgc gaaaaattat     300
tactatgata ctagtgctta ttactacgta gggtccgact actttgacta ctggggccaa     360
gggacaatgg tcaccgtctc gagt                                             384

```
<210> SEQ ID NO 56
<211> LENGTH: 128
<212> TYPE: PRT
<213> ORGANISM: Homo sapiens
<220> FEATURE:
<223> OTHER INFORMATION: Bbbt0654 VH

<400> SEQUENCE: 56

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asn Tyr Tyr Tyr Asp Thr Ser Ala Tyr Tyr Val Gly Ser
            100                 105                 110

Asp Tyr Phe Asp Tyr Trp Gly Gln Gly Thr Met Val Thr Val Ser Ser
        115                 120                 125

<210> SEQ ID NO 57
<211> LENGTH: 5
<212> TYPE: PRT
<213> ORGANISM: Homo sapiens
<220> FEATURE:
<223> OTHER INFORMATION: Bbbt0654  VH CDR1

<400> SEQUENCE: 57

Ser Tyr Ala Met Ser
                 5

<210> SEQ ID NO 58
<211> LENGTH: 17
<212> TYPE: PRT
<213> ORGANISM: Homo sapiens
<220> FEATURE:
<223> OTHER INFORMATION: Bbbt0654  VH CDR2

<400> SEQUENCE: 58

Ala Ile Ser Gly Ser Gly Gly Ser Thr Tyr Tyr Ala Asp Ser Val Lys
                 5                  10                  15

Gly

<210> SEQ ID NO 59
<211> LENGTH: 19
<212> TYPE: PRT
<213> ORGANISM: Homo sapiens
<220> FEATURE:
<223> OTHER INFORMATION: Bbbt0654  VH CDR3

<400> SEQUENCE: 59

Asn Tyr Tyr Tyr Asp Thr Ser Ala Tyr Tyr Val Gly Ser Asp Tyr
                 5                  10                  15

Phe Asp Tyr

<210> SEQ ID NO 60
<211> LENGTH: 30
```

```
<212> TYPE: PRT
<213> ORGANISM: Homo sapiens
<220> FEATURE:
<223> OTHER INFORMATION: Bbbt0654 VH FW1

<400> SEQUENCE: 60

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser
             20                  25                  30

<210> SEQ ID NO 61
<211> LENGTH: 14
<212> TYPE: PRT
<213> ORGANISM: Homo sapiens
<220> FEATURE:
<223> OTHER INFORMATION: Bbbt0654 VH FW2

<400> SEQUENCE: 61

Trp Val Arg Gln Ala Pro Gly Lys Gly Leu Glu Trp Val Ser
                 5                  10

<210> SEQ ID NO 62
<211> LENGTH: 32
<212> TYPE: PRT
<213> ORGANISM: Homo sapiens
<220> FEATURE:
<223> OTHER INFORMATION: Bbbt0654 VH FW3

<400> SEQUENCE: 62

Arg Phe Thr Ile Ser Arg Asp Asn Ser Lys Asn Thr Leu Tyr Leu Gln
                 5                  10                  15

Met Asn Ser Leu Arg Ala Glu Asp Thr Ala Val Tyr Tyr Cys Ala Lys
             20                  25                  30

<210> SEQ ID NO 63
<211> LENGTH: 11
<212> TYPE: PRT
<213> ORGANISM: Homo sapiens
<220> FEATURE:
<223> OTHER INFORMATION: Bbbt0654 VH FW 4

<400> SEQUENCE: 63

Trp Gly Gln Gly Thr Met Val Thr Val Ser Ser
                 5                  10

<210> SEQ ID NO 64
<211> LENGTH: 330
<212> TYPE: DNA
<213> ORGANISM: Homo sapiens
<220> FEATURE:
<223> OTHER INFORMATION: Bbbt0654 VL

<400> SEQUENCE: 64
cagtctgccc tgactcagcc tgcctccgtg tctgggtctc ctggacagtc gataaccatc      60
tcctgcactg caaccagcag taacgttggc gcttataact tgtctcctg gtaccaacaa      120 cacccaggca agccccccaa agtcctgatt tatagggtca gtaatcggcc ttcagggggtt    180 tctaatcgct ctctggctc caagtctggc aacacggccc cctgaccat ctctgggctc       240 caggctgacg acgaggctga ttattattgc agctcatata caaccgacta catttgggtg     300
ttcggcggag ggaccaagct gaccgtccta                                      330

<210> SEQ ID NO 65
```

-continued

```
<211> LENGTH: 110
<212> TYPE: PRT
<213> ORGANISM: Homo sapiens
<220> FEATURE:
<223> OTHER INFORMATION: Bbbt0654 VL

<400> SEQUENCE: 65

Gln Ser Ala Leu Thr Gln Pro Ala Ser Val Ser Gly Ser Pro Gly Gln
  1               5                  10                  15

Ser Ile Thr Ile Ser Cys Thr Ala Thr Ser Ser Asn Val Gly Ala Tyr
             20                  25                  30

Asn Phe Val Ser Trp Tyr Gln Gln His Pro Gly Lys Ala Pro Lys Val
         35                  40                  45

Leu Ile Tyr Arg Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Asp Asp Glu Ala Asp Tyr Tyr Cys Ser Ser Tyr Thr Thr Asp
                 85                  90                  95

Tyr Ile Trp Val Phe Gly Gly Gly Thr Lys Leu Thr Val Leu
            100                 105                 110

<210> SEQ ID NO 66
<211> LENGTH: 14
<212> TYPE: PRT
<213> ORGANISM: Homo sapiens
<220> FEATURE:
<223> OTHER INFORMATION: Bbbt0654 VL CDR1

<400> SEQUENCE: 66

Thr Ala Thr Ser Ser Asn Val Gly Ala Tyr Asn Phe Val Ser
  1               5                  10

<210> SEQ ID NO 67
<211> LENGTH: 7
<212> TYPE: PRT
<213> ORGANISM: Homo sapiens
<220> FEATURE:
<223> OTHER INFORMATION: Bbbt0654 VL CDR2

<400> SEQUENCE: 67

Arg Val Ser Asn Arg Pro Ser
  1               5

<210> SEQ ID NO 68
<211> LENGTH: 10
<212> TYPE: PRT
<213> ORGANISM: Homo sapiens
<220> FEATURE:
<223> OTHER INFORMATION: Bbbt0654 VL CDR3

<400> SEQUENCE: 68

Ser Ser Tyr Thr Thr Asp Tyr Ile Trp Val
  1               5                  10

<210> SEQ ID NO 69
<211> LENGTH: 22
<212> TYPE: PRT
<213> ORGANISM: Homo sapiens
<220> FEATURE:
<223> OTHER INFORMATION: Bbbt0654 VL FW1

<400> SEQUENCE: 69

Gln Ser Ala Leu Thr Gln Pro Ala Ser Val Ser Gly Ser Pro Gly Gln
```

Ser Ile Thr Ile Ser Cys
            20

<210> SEQ ID NO 70
<211> LENGTH: 15
<212> TYPE: PRT
<213> ORGANISM: Homo sapiens
<220> FEATURE:
<223> OTHER INFORMATION: Bbbt0654 VL FW2

<400> SEQUENCE: 70

Trp Tyr Gln Gln His Pro Gly Lys Ala Pro Lys Val Leu Ile Tyr
                5                  10                  15

<210> SEQ ID NO 71
<211> LENGTH: 32
<212> TYPE: PRT
<213> ORGANISM: Homo sapiens
<220> FEATURE:
<223> OTHER INFORMATION: Bbbt0654 VL FW3

<400> SEQUENCE: 71

Gly Val Ser Asn Arg Phe Ser Gly Ser Lys Ser Gly Asn Thr Ala Ser
                5                  10                  15

Leu Thr Ile Ser Gly Leu Gln Ala Asp Asp Glu Ala Asp Tyr Tyr Cys
            20                  25                  30

<210> SEQ ID NO 72
<211> LENGTH: 10
<212> TYPE: PRT
<213> ORGANISM: Homo sapiens
<220> FEATURE:
<223> OTHER INFORMATION: Bbbt0654 VL FW4

<400> SEQUENCE: 72

Phe Gly Gly Gly Thr Lys Leu Thr Val Leu
                5                  10

<210> SEQ ID NO 73
<211> LENGTH: 360
<212> TYPE: DNA
<213> ORGANISM: Homo sapiens
<220> FEATURE:
<223> OTHER INFORMATION: Bbbt0726 VH

<400> SEQUENCE: 73
caggtacagc tgcagcagtc aggggctgag gtgaagaagc ctgggtcctc ggtgagggtc       60
tcctgcaagg cttctggagg caccttcaac agttatgcta tcaactgggt gcgacaggcc     120
cctggacaag gcttgagtg gatgggaggg atcatcactt tctttggtac aacaacctac     180
gcacagaagt tccagggcag agtcacgatt accgcggacg aatccacgag cacagcctac     240
atggagctga gcagcctgag atctgacgac acggccgtgt attattgtgc gaggaatccc     300
cgtattgtgg gcggagcttt tgatatctgg gggaaaggga ccacggtcac cgtctcgagt     360

<210> SEQ ID NO 74
<211> LENGTH: 120
<212> TYPE: PRT
<213> ORGANISM: Homo sapiens
<220> FEATURE:
<223> OTHER INFORMATION: Bbbt0726 VH

<400> SEQUENCE: 74

Gln Val Gln Leu Gln Gln Ser Gly Ala Glu Val Lys Lys Pro Gly Ser
                5                  10                  15

Ser Val Arg Val Ser Cys Lys Ala Ser Gly Gly Thr Phe Asn Ser Tyr
            20                  25                  30

Ala Ile Asn Trp Val Arg Gln Ala Pro Gly Gln Gly Leu Glu Trp Met
        35                  40                  45

Gly Gly Ile Ile Thr Phe Phe Gly Thr Thr Thr Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asn Pro Arg Ile Val Gly Gly Ala Phe Asp Ile Trp Gly Lys
            100                 105                 110

Gly Thr Thr Val Thr Val Ser Ser
        115                 120

<210> SEQ ID NO 75
<211> LENGTH: 5
<212> TYPE: PRT
<213> ORGANISM: Homo sapiens
<220> FEATURE:
<223> OTHER INFORMATION: Bbbt0726 VH CDR1

<400> SEQUENCE: 75

Ser Tyr Ala Ile Asn
                5

<210> SEQ ID NO 76
<211> LENGTH: 17
<212> TYPE: PRT
<213> ORGANISM: Homo sapiens
<220> FEATURE:
<223> OTHER INFORMATION: Bbbt0726 VH CDR2

<400> SEQUENCE: 76

Gly Ile Ile Thr Phe Phe Gly Thr Thr Thr Tyr Ala Gln Lys Phe Gln
                5                  10                  15

Gly

<210> SEQ ID NO 77
<211> LENGTH: 11
<212> TYPE: PRT
<213> ORGANISM: Homo sapiens
<220> FEATURE:
<223> OTHER INFORMATION: Bbbt0726 VH CDR3

<400> SEQUENCE: 77

Asn Pro Arg Ile Val Gly Gly Ala Phe Asp Ile
                5                  10

<210> SEQ ID NO 78
<211> LENGTH: 30
<212> TYPE: PRT
<213> ORGANISM: Homo sapiens
<220> FEATURE:
<223> OTHER INFORMATION: Bbbt0726 VH FW1

<400> SEQUENCE: 78

Gln Val Gln Leu Gln Gln Ser Gly Ala Glu Val Lys Lys Pro Gly Ser
                5                  10                  15

Ser Val Arg Val Ser Cys Lys Ala Ser Gly Gly Thr Phe Asn
            20                  25

<210> SEQ ID NO 79
<211> LENGTH: 14
<212> TYPE: PRT
<213> ORGANISM: Homo sapiens
<220> FEATURE:
<223> OTHER INFORMATION: Bbbt0726 VH FW2

<400> SEQUENCE: 79

Trp Val Arg Gln Ala Pro Gly Gln Gly Leu Glu Trp Met Gly
                5                   10

<210> SEQ ID NO 80
<211> LENGTH: 32
<212> TYPE: PRT
<213> ORGANISM: Homo sapiens
<220> FEATURE:
<223> OTHER INFORMATION: Bbbt0726 VH FW3

<400> SEQUENCE: 80

Arg Val Thr Ile Thr Ala Asp Glu Ser Thr Ser Thr Ala Tyr Met Glu
                5                   10                  15
Leu Ser Ser Leu Arg Ser Asp Asp Thr Ala Val Tyr Tyr Cys Ala Arg
            20                  25                  30

<210> SEQ ID NO 81
<211> LENGTH: 11
<212> TYPE: PRT
<213> ORGANISM: Homo sapiens
<220> FEATURE:
<223> OTHER INFORMATION: Bbbt0726 VH FW4

<400> SEQUENCE: 81

Trp Gly Lys Gly Thr Thr Val Thr Val Ser Ser
                5                   10

<210> SEQ ID NO 82
<211> LENGTH: 324
<212> TYPE: DNA
<213> ORGANISM: Homo sapiens
<220> FEATURE:
<223> OTHER INFORMATION: Bbbt0726 VL

<400> SEQUENCE: 82
tcgtctgagc tgactcagga ccctgctgtg tctgtggcct tgggacagac agtcaggatc      60
acatgccaag agacagcct cagaagctat tatgcaagct ggtaccagca gaagccagga     120 caggccctg tacttgtcat ctatggtaaa acaaccggc cctcaggggt cccagaccga      180
ttctctggct ccagctcagg aaacacagct tccttgacca tcactgggc tcaggcggaa     240 gatgaggctg actattactg taactcccgg gacagcagtg gtaaccatgt ggtattcggc     300
ggagggacca agctgaccgt ccta                                            324

<210> SEQ ID NO 83
<211> LENGTH: 108
<212> TYPE: PRT
<213> ORGANISM: Homo sapiens
<220> FEATURE:
<223> OTHER INFORMATION: Bbbt0726 VL

<400> SEQUENCE: 83

Ser Ser Glu Leu Thr Gln Asp Pro Ala Val Ser Val Ala Leu Gly Gln
                5                   10                  15

-continued

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Val Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105

<210> SEQ ID NO 84
<211> LENGTH: 11
<212> TYPE: PRT
<213> ORGANISM: Homo sapiens
<220> FEATURE:
<223> OTHER INFORMATION: Bbbt0726 VL CDR1

<400> SEQUENCE: 84

Gln Gly Asp Ser Leu Arg Ser Tyr Tyr Ala Ser
            5                   10

<210> SEQ ID NO 85
<211> LENGTH: 7
<212> TYPE: PRT
<213> ORGANISM: Homo sapiens
<220> FEATURE:
<223> OTHER INFORMATION: Bbbt0726 VL CDR2

<400> SEQUENCE: 85

Gly Lys Asn Asn Arg Pro Ser
            5

<210> SEQ ID NO 86
<211> LENGTH: 11
<212> TYPE: PRT
<213> ORGANISM: Homo sapiens
<220> FEATURE:
<223> OTHER INFORMATION: Bbbt0726 VL CDR3

<400> SEQUENCE: 86

Asn Ser Arg Asp Ser Ser Gly Asn His Val Val
            5                   10

<210> SEQ ID NO 87
<211> LENGTH: 22
<212> TYPE: PRT
<213> ORGANISM: Homo sapiens
<220> FEATURE:
<223> OTHER INFORMATION: Bbbt0726 VL FW1

<400> SEQUENCE: 87

Ser Ser Glu Leu Thr Gln Asp Pro Ala Val Ser Val Ala Leu Gly Gln
            5                   10                  15

Thr Val Arg Ile Thr Cys
            20

<210> SEQ ID NO 88
<211> LENGTH: 15
<212> TYPE: PRT
<213> ORGANISM: Homo sapiens
<220> FEATURE:

<223> OTHER INFORMATION: Bbbt0726 VL FW2

<400> SEQUENCE: 88

Trp Tyr Gln Gln Lys Pro Gly Gln Ala Pro Val Leu Val Ile Tyr
                5                   10                  15

<210> SEQ ID NO 89
<211> LENGTH: 32
<212> TYPE: PRT
<213> ORGANISM: Homo sapiens
<220> FEATURE:
<223> OTHER INFORMATION: Bbbt0726 VL FW3

<400> SEQUENCE: 89

Gly Val Pro Asp Arg Phe Ser Gly Ser Ser Gly Asn Thr Ala Ser
                5                   10                  15

Leu Thr Ile Thr Gly Ala Gln Ala Glu Asp Glu Ala Asp Tyr Tyr Cys
            20                  25                  30

<210> SEQ ID NO 90
<211> LENGTH: 10
<212> TYPE: PRT
<213> ORGANISM: Homo sapiens
<220> FEATURE:
<223> OTHER INFORMATION: Bbbt0726 VL FW4

<400> SEQUENCE: 90

Phe Gly Gly Gly Thr Lys Leu Thr Val Leu
                5                   10

<210> SEQ ID NO 91
<211> LENGTH: 357
<212> TYPE: DNA
<213> ORGANISM: Homo sapiens
<220> FEATURE:
<223> OTHER INFORMATION: Bbbt0727 VH

<400> SEQUENCE: 91
caggtgcagc tggtgcagtc tggggctgag gtgaagaagc ctgggtcctc ggtgaaggtc       60
tcctgcaagg cttctggaga cactttccgc agctatatta tcagctgggt gcgacaggcc      120
cctggacaag gacttgagtg ggtgggaggg atcatcccta tgtttggcac atcaaattat      180
gcacagcagt tccagggcaa agtcaccatt accgcggacg aatccacgag cacagcctac      240
atggagctga gcagcctgag atctgaggac acggccgtgt attactgtgc gagaggtggg      300
gcccgatact actacatgga cgtctggggc cgagggacaa tggtcaccgt ctcttca        357

<210> SEQ ID NO 92
<211> LENGTH: 119
<212> TYPE: PRT
<213> ORGANISM: Homo sapiens
<220> FEATURE:
<223> OTHER INFORMATION: Bbbt0727 VH

<400> SEQUENCE: 92

Gln Val Gln Leu Val Gln Ser Gly Ala Glu Val Lys Lys Pro Gly Ser
                5                   10                  15

Ser Val Lys Val Ser Cys Lys Ala Ser Gly Asp Thr Phe Arg Ser Tyr
            20                  25                  30

Ile Ile Ser Trp Val Arg Gln Ala Pro Gly Gln Gly Leu Glu Trp Val
        35                  40                  45

Gly Gly Ile Ile Pro Met Phe Gly Thr Ser Asn Tyr Ala Gln Gln Phe
    50                  55                  60

Gln Gly Lys Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Arg Tyr Tyr Tyr Met Asp Val Trp Gly Arg Gly
            100                 105                 110

Thr Met Val Thr Val Ser Ser
        115

<210> SEQ ID NO 93
<211> LENGTH: 5
<212> TYPE: PRT
<213> ORGANISM: Homo sapiens
<220> FEATURE:
<223> OTHER INFORMATION: Bbbt0727 VH CDR1

<400> SEQUENCE: 93

Ser Tyr Ile Ile Ser
            5

<210> SEQ ID NO 94
<211> LENGTH: 17
<212> TYPE: PRT
<213> ORGANISM: Homo sapiens
<220> FEATURE:
<223> OTHER INFORMATION: Bbbt0727 VH CDR2

<400> SEQUENCE: 94

Gly Ile Ile Pro Met Phe Gly Thr Ser Asn Tyr Ala Gln Gln Phe Gln
                5                   10                  15

Gly

<210> SEQ ID NO 95
<211> LENGTH: 10
<212> TYPE: PRT
<213> ORGANISM: Homo sapiens
<220> FEATURE:
<223> OTHER INFORMATION: Bbbt0727 VH CDR3

<400> SEQUENCE: 95

Gly Gly Ala Arg Tyr Tyr Tyr Met Asp Val
                5                   10

<210> SEQ ID NO 96
<211> LENGTH: 30
<212> TYPE: PRT
<213> ORGANISM: Homo sapiens
<220> FEATURE:
<223> OTHER INFORMATION: Bbbt0727 VH FW1

<400> SEQUENCE: 96

Gln Val Gln Leu Val Gln Ser Gly Ala Glu Val Lys Lys Pro Gly Ser
                5                   10                  15

Ser Val Lys Val Ser Cys Lys Ala Ser Gly Asp Thr Phe Arg
            20                  25                  30

<210> SEQ ID NO 97
<211> LENGTH: 14
<212> TYPE: PRT
<213> ORGANISM: Homo sapiens
<220> FEATURE:
<223> OTHER INFORMATION: Bbbt0727 VH FW2

<400> SEQUENCE: 97

Trp Val Arg Gln Ala Pro Gly Gln Gly Leu Glu Trp Val Gly
                5                   10

<210> SEQ ID NO 98
<211> LENGTH: 32
<212> TYPE: PRT
<213> ORGANISM: Homo sapiens
<220> FEATURE:
<223> OTHER INFORMATION: Bbbt0727 VH FW3

<400> SEQUENCE: 98

Lys Val Thr Ile Thr Ala Asp Glu Ser Thr Ser Thr Ala Tyr Met Glu
                5                   10                  15

Leu Ser Ser Leu Arg Ser Glu Asp Thr Ala Val Tyr Tyr Cys Ala Arg
            20                  25                  30

<210> SEQ ID NO 99
<211> LENGTH: 11
<212> TYPE: PRT
<213> ORGANISM: Homo sapiens
<220> FEATURE:
<223> OTHER INFORMATION: Bbbt0727 VH FW4

<400> SEQUENCE: 99

Trp Gly Arg Gly Thr Met Val Thr Val Ser Ser
                5                   10

<210> SEQ ID NO 100
<211> LENGTH: 324
<212> TYPE: DNA
<213> ORGANISM: Homo sapiens
<220> FEATURE:
<223> OTHER INFORMATION: Bbbt0727 VL

<400> SEQUENCE: 100
tcgtctgagc tgactcagga ccctgctgtg tctgtggcct tgggacagac agtcaggatc       60
acatgccaag gagacagcct cagaagctat tatgcaagct ggtaccagca gaagccagga      120
caggcccctg tacttgtcat ctatggtaaa aacaaccggc cctcagggat cccagaccga      180
ttctctggct ccagctcagg aaacacagct tccttgacca tcactgggcc tcaggcggaa      240
gatgaggctg actattactg taactcccgg gacagcagtg gtaaccatgt ggtattcggc      300
ggagggacca agctgaccgt ccta                                             324

<210> SEQ ID NO 101
<211> LENGTH: 108
<212> TYPE: PRT
<213> ORGANISM: Homo sapiens
<220> FEATURE:
<223> OTHER INFORMATION: Bbbt0727 VL

<400> SEQUENCE: 101

Ser Ser Glu Leu Thr Gln Asp Pro Ala Val Ser Val Ala Leu Gly Gln
                5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

```
Asp Glu Ala Asp Tyr Tyr Cys Asn Ser Arg Asp Ser Ser Gly Asn His
                85                  90                  95
Val Val Phe Gly Gly Gly Thr Lys Leu Thr Val Leu
            100                 105

<210> SEQ ID NO 102
<211> LENGTH: 11
<212> TYPE: PRT
<213> ORGANISM: Homo sapiens
<220> FEATURE:
<223> OTHER INFORMATION: Bbbt0727  VL CDR1

<400> SEQUENCE: 102

Gln Gly Asp Ser Leu Arg Ser Tyr Tyr Ala Ser
                 5                  10

<210> SEQ ID NO 103
<211> LENGTH: 7
<212> TYPE: PRT
<213> ORGANISM: Homo sapiens
<220> FEATURE:
<223> OTHER INFORMATION: Bbbt0727  VL CDR2

<400> SEQUENCE: 103

Gly Lys Asn Asn Arg Pro Ser
                 5

<210> SEQ ID NO 104
<211> LENGTH: 11
<212> TYPE: PRT
<213> ORGANISM: Homo sapiens
<220> FEATURE:
<223> OTHER INFORMATION: Bbbt0727  VL CDR3

<400> SEQUENCE: 104

Asn Ser Arg Asp Ser Ser Gly Asn His Val Val
                 5                  10

<210> SEQ ID NO 105
<211> LENGTH: 22
<212> TYPE: PRT
<213> ORGANISM: Homo sapiens
<220> FEATURE:
<223> OTHER INFORMATION: Bbbt0727  VL FW1

<400> SEQUENCE: 105

Ser Ser Glu Leu Thr Gln Asp Pro Ala Val Ser Val Ala Leu Gly Gln
                 5                  10                  15
Thr Val Arg Ile Thr Cys
            20

<210> SEQ ID NO 106
<211> LENGTH: 15
<212> TYPE: PRT
<213> ORGANISM: Homo sapiens
<220> FEATURE:
<223> OTHER INFORMATION: Bbbt0727  VL FW2

<400> SEQUENCE: 106

Trp Tyr Gln Gln Lys Pro Gly Gln Ala Pro Val Leu Val Ile Tyr
                 5                  10                  15

<210> SEQ ID NO 107
<211> LENGTH: 32
<212> TYPE: PRT
```

<213> ORGANISM: Homo sapiens
<220> FEATURE:
<223> OTHER INFORMATION: Bbbt0727 VL FW3

<400> SEQUENCE: 107

Gly Ile Pro Asp Arg Phe Ser Gly Ser Ser Gly Asn Thr Ala Ser
                5                   10                  15

Leu Thr Ile Thr Gly Ala Gln Ala Glu Asp Glu Ala Asp Tyr Tyr Cys
                20                  25                  30

<210> SEQ ID NO 108
<211> LENGTH: 10
<212> TYPE: PRT
<213> ORGANISM: Homo sapiens
<220> FEATURE:
<223> OTHER INFORMATION: Bbbt0727 VL FW4

<400> SEQUENCE: 108

Phe Gly Gly Gly Thr Lys Leu Thr Val Leu
                5                   10

<210> SEQ ID NO 109
<211> LENGTH: 360
<212> TYPE: DNA
<213> ORGANISM: Homo sapiens
<220> FEATURE:
<223> OTHER INFORMATION: Bbbt0732 VH

<400> SEQUENCE: 109
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gaaacgtcgg    300
agggactact actacgatat ggacgtctgg ggccaaggga caatggtcac cgtctcgagt    360

<210> SEQ ID NO 110
<211> LENGTH: 120
<212> TYPE: PRT
<213> ORGANISM: Homo sapiens
<220> FEATURE:
<223> OTHER INFORMATION: Bbbt0732 VH

<400> SEQUENCE: 110

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Arg Arg Asp Tyr Tyr Tyr Asp Met Asp Val Trp Gly Gln
                100                 105                 110

Gly Thr Met Val Thr Val Ser Ser

<210> SEQ ID NO 111
<211> LENGTH: 5
<212> TYPE: PRT
<213> ORGANISM: Homo sapiens
<220> FEATURE:
<223> OTHER INFORMATION: Bbbt0732 VH CDR1

<400> SEQUENCE: 111

Ser Tyr Ala Met Ser
              5

<210> SEQ ID NO 112
<211> LENGTH: 17
<212> TYPE: PRT
<213> ORGANISM: Homo sapiens
<220> FEATURE:
<223> OTHER INFORMATION: Bbbt0732 VH CDR2

<400> SEQUENCE: 112

Ala Ile Ser Gly Ser Gly Gly Ser Thr Tyr Tyr Ala Asp Ser Val Lys
                5                   10                  15

Gly

<210> SEQ ID NO 113
<211> LENGTH: 11
<212> TYPE: PRT
<213> ORGANISM: Homo sapiens
<220> FEATURE:
<223> OTHER INFORMATION: Bbbt0732 VH CDR3

<400> SEQUENCE: 113

Arg Arg Arg Asp Tyr Tyr Tyr Asp Met Asp Val
                5                   10

<210> SEQ ID NO 114
<211> LENGTH: 30
<212> TYPE: PRT
<213> ORGANISM: Homo sapiens
<220> FEATURE:
<223> OTHER INFORMATION: Bbbt0732 VH FW1

<400> SEQUENCE: 114

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Thr Phe Ser
        20                  25                  30

<210> SEQ ID NO 115
<211> LENGTH: 14
<212> TYPE: PRT
<213> ORGANISM: Homo sapiens
<220> FEATURE:
<223> OTHER INFORMATION: Bbbt0732 VH FW2

<400> SEQUENCE: 115

Trp Val Arg Gln Ala Pro Gly Lys Gly Leu Glu Trp Val Ser
                5                   10

<210> SEQ ID NO 116
<211> LENGTH: 32
<212> TYPE: PRT
<213> ORGANISM: Homo sapiens
<220> FEATURE:
<223> OTHER INFORMATION: Bbbt0732 VH FW 3

<400> SEQUENCE: 116

Arg Phe Thr Ile Ser Arg Asp Asn Ser Lys Asn Thr Leu Tyr Leu Gln
                 5                   10                  15

Met Asn Ser Leu Arg Ala Glu Asp Thr Ala Val Tyr Tyr Cys Ala Lys
            20                  25                  30

<210> SEQ ID NO 117
<211> LENGTH: 11
<212> TYPE: PRT
<213> ORGANISM: Homo sapiens
<220> FEATURE:
<223> OTHER INFORMATION: Bbbt0732 VH FW4

<400> SEQUENCE: 117

Trp Gly Gln Gly Thr Met Val Thr Val Ser Ser
                 5                   10

<210> SEQ ID NO 118
<211> LENGTH: 324
<212> TYPE: DNA
<213> ORGANISM: Homo sapiens
<220> FEATURE:
<223> OTHER INFORMATION: Bbbt0732 VL

<400> SEQUENCE: 118
tcttctgagc tgactcagga ccctgctgtg tctgtggcct tgggacagac agtcaggatc      60
acatgccaag agacagcct cagaacctat tatgcaagct ggtaccagca caagccagga     120
caggcccctg tacttgtcat gtatggtaaa gataaccgac cctcagggat cccagaccga     180
ttctctggct ccagctcagg aaccacagct tccttgacca tcactggggc tcaggcggaa     240
gatgaggctg actattactg taactcccgg gacagcagtg gtcaccctgt ggtattcggc     300
ggagggacca agctgaccgt ccta                                           324

<210> SEQ ID NO 119
<211> LENGTH: 108
<212> TYPE: PRT
<213> ORGANISM: Homo sapiens
<220> FEATURE:
<223> OTHER INFORMATION: Bbbt0732 VL

<400> SEQUENCE: 119

Ser Ser Glu Leu Thr Gln Asp Pro Ala Val Ser Val Ala Leu Gly Gln
                 5                   10                  15

Thr Val Arg Ile Thr Cys Gln Gly Asp Ser Leu Arg Tyr Tyr Ala
            20                  25                  30

Ser Trp Tyr Gln His Lys Pro Gly Gln Ala Pro Val Leu Val Met Tyr
        35                  40                  45

Gly Lys Asp Asn Arg Pro Ser Gly Ile Pro Asp Arg Phe Ser Gly Ser
    50                  55                  60

Ser Ser Gly Thr Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly His Pro
                85                  90                  95

Val Val Phe Gly Gly Gly Thr Lys Leu Thr Val Leu
                100                 105

<210> SEQ ID NO 120
<211> LENGTH: 11
<212> TYPE: PRT

```
<213> ORGANISM: Homo sapiens
<220> FEATURE:
<223> OTHER INFORMATION: Bbbt0732 VL CDR1

<400> SEQUENCE: 120

Gln Gly Asp Ser Leu Arg Thr Tyr Tyr Ala Ser
                5                   10

<210> SEQ ID NO 121
<211> LENGTH: 7
<212> TYPE: PRT
<213> ORGANISM: Homo sapiens
<220> FEATURE:
<223> OTHER INFORMATION: Bbbt0732 VL CDR2

<400> SEQUENCE: 121

Gly Lys Asp Asn Arg Pro Ser
                5

<210> SEQ ID NO 122
<211> LENGTH: 11
<212> TYPE: PRT
<213> ORGANISM: Homo sapiens
<220> FEATURE:
<223> OTHER INFORMATION: Bbbt0732 VL CDR3

<400> SEQUENCE: 122

Asn Ser Arg Asp Ser Ser Gly His Pro Val Val
                5                   10

<210> SEQ ID NO 123
<211> LENGTH: 22
<212> TYPE: PRT
<213> ORGANISM: Homo sapiens
<220> FEATURE:
<223> OTHER INFORMATION: Bbbt0732 VL FW1

<400> SEQUENCE: 123

Ser Ser Glu Leu Thr Gln Asp Pro Ala Val Ser Val Ala Leu Gly Gln
                5                   10                  15

Thr Val Arg Ile Thr Cys
            20

<210> SEQ ID NO 124
<211> LENGTH: 15
<212> TYPE: PRT
<213> ORGANISM: Homo sapiens
<220> FEATURE:
<223> OTHER INFORMATION: Bbbt0732 VL FW2

<400> SEQUENCE: 124

Trp Tyr Gln His Lys Pro Gly Gln Ala Pro Val Leu Val Met Tyr
                5                   10                  15

<210> SEQ ID NO 125
<211> LENGTH: 32
<212> TYPE: PRT
<213> ORGANISM: Homo sapiens
<220> FEATURE:
<223> OTHER INFORMATION: Bbbt0732 VL FW3

<400> SEQUENCE: 125

Gly Ile Pro Asp Arg Phe Ser Gly Ser Ser Ser Gly Thr Thr Ala Ser
                5                   10                  15

Leu Thr Ile Thr Gly Ala Gln Ala Glu Asp Glu Ala Asp Tyr Tyr Cys
            20                  25                  30
```

<210> SEQ ID NO 126
<211> LENGTH: 10
<212> TYPE: PRT
<213> ORGANISM: Homo sapiens
<220> FEATURE:
<223> OTHER INFORMATION: Bbbt0732 VL FW4

<400> SEQUENCE: 126

Phe Gly Gly Gly Thr Lys Leu Thr Val Leu
                 5                  10

<210> SEQ ID NO 127
<211> LENGTH: 366
<212> TYPE: DNA
<213> ORGANISM: Homo sapiens
<220> FEATURE:
<223> OTHER INFORMATION: Bbbt0754 VH

<400> SEQUENCE: 127
gaggtgcagc tgttggagtc tgggggaggc ttggtacagc ctgggggtc cctgagactc      60 tcctgtgcag cctctggatt caaaattacc cactatacta tgggctgggt ccgccaggct    120
ccagggaagg ggctggagtg gtctcacgc atcacgtggg gcggtgacaa cacctttac     180 tccaactccg tgaggggccg gttcaccatc tccagagaca attccaagaa cacgctgtat    240
ctgcaaatga acagcctgag agccgaggac acggccgtat attactgtgc aacaggacg    300 ttcggggagt tattccccga ctactttaag tattggggcc ggggacaat ggtcaccgtc    360 tcgagt                                                              366

<210> SEQ ID NO 128
<211> LENGTH: 122
<212> TYPE: PRT
<213> ORGANISM: Homo sapiens
<220> FEATURE:
<223> OTHER INFORMATION: Bbbt0754 VH

<400> SEQUENCE: 128

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Lys Ile Thr His Tyr
             20                  25                  30

Thr Met Gly Trp Val Arg Gln Ala Pro Gly Lys Gly Leu Glu Trp Val
         35                  40                  45

Ser Arg Ile Thr Trp Gly Gly Asp Asn Thr Phe Tyr Ser Asn Ser Val
     50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Gly Thr Phe Gly Glu Leu Phe Pro Asp Tyr Phe Lys Tyr Trp
            100                 105                 110

Gly Arg Gly Thr Met Val Thr Val Ser Ser
        115                 120

<210> SEQ ID NO 129
<211> LENGTH: 5
<212> TYPE: PRT
<213> ORGANISM: Homo sapiens
<220> FEATURE:
<223> OTHER INFORMATION: Bbbt0754 VH CDR1

-continued

```
<400> SEQUENCE: 129

His Tyr Thr Met Gly
              5

<210> SEQ ID NO 130
<211> LENGTH: 17
<212> TYPE: PRT
<213> ORGANISM: Homo sapiens
<220> FEATURE:
<223> OTHER INFORMATION: Bbbt0754 VH CDR2

<400> SEQUENCE: 130

Arg Ile Thr Trp Gly Gly Asp Asn Thr Phe Tyr Ser Asn Ser Val Arg
              5                  10                  15
Gly

<210> SEQ ID NO 131
<211> LENGTH: 13
<212> TYPE: PRT
<213> ORGANISM: Homo sapiens
<220> FEATURE:
<223> OTHER INFORMATION: Bbbt0754 VH CDR3

<400> SEQUENCE: 131

Gly Thr Phe Gly Glu Leu Phe Pro Asp Tyr Phe Lys Tyr
              5                  10

<210> SEQ ID NO 132
<211> LENGTH: 30
<212> TYPE: PRT
<213> ORGANISM: Homo sapiens
<220> FEATURE:
<223> OTHER INFORMATION: Bbbt0754 VH FW1

<400> SEQUENCE: 132

Glu Val Gln Leu Leu Glu Ser Gly Gly Gly Leu Val Gln Pro Gly Gly
              5                  10                  15
Ser Leu Arg Leu Ser Cys Ala Ala Ser Gly Phe Lys Ile Thr
         20                  25                  30

<210> SEQ ID NO 133
<211> LENGTH: 14
<212> TYPE: PRT
<213> ORGANISM: Homo sapiens
<220> FEATURE:
<223> OTHER INFORMATION: Bbbt0754 VH FW2

<400> SEQUENCE: 133

Trp Val Arg Gln Ala Pro Gly Lys Gly Leu Glu Trp Val Ser
              5                  10

<210> SEQ ID NO 134
<211> LENGTH: 32
<212> TYPE: PRT
<213> ORGANISM: Homo sapiens
<220> FEATURE:
<223> OTHER INFORMATION: Bbbt0754 VH FW3

<400> SEQUENCE: 134

Arg Phe Thr Ile Ser Arg Asp Asn Ser Lys Asn Thr Leu Tyr Leu Gln
              5                  10                  15
Met Asn Ser Leu Arg Ala Glu Asp Thr Ala Val Tyr Tyr Cys Ala Thr
         20                  25                  30
```

<210> SEQ ID NO 135
<211> LENGTH: 11
<212> TYPE: PRT
<213> ORGANISM: Homo sapiens
<220> FEATURE:
<223> OTHER INFORMATION: Bbbt0754 VH FW4

<400> SEQUENCE: 135

Trp Gly Arg Gly Thr Met Val Thr Val Ser Ser
                5                   10

<210> SEQ ID NO 136
<211> LENGTH: 333
<212> TYPE: DNA
<213> ORGANISM: Homo sapiens
<220> FEATURE:
<223> OTHER INFORMATION: Bbbt0754 VL

<400> SEQUENCE: 136
caggctgtgc tgactcagcc gtcctcagtg tctggggccc cagggcagag ggtcaccatc      60
ccctgcactg ggagcagctc aacatcggg gcaggttatg atgtaaactg gtaccagcag     120
cttccaggaa cagcccccaa actcctcatc tttcataaca acattcggcc ctcagggtc     180 cctgaccgat tctctggctc caagtctggc acctcagtct ccctggccat cactgggctc     240
caggctgagg atgaggctga ttattactgc cagtcctatg acagcagcct gagtgcttgg     300
gtcttcggcg agggaccaa ggtcaccgtc cta                                   333

<210> SEQ ID NO 137
<211> LENGTH: 111
<212> TYPE: PRT
<213> ORGANISM: Homo sapiens
<220> FEATURE:
<223> OTHER INFORMATION: Bbbt0754 VL

<400> SEQUENCE: 137

Gln Ala Val Leu Thr Gln Pro Ser Ser Val Ser Gly Ala Pro Gly Gln
                5                   10                  15

Arg Val Thr Ile Pro Cys Thr Gly Ser Ser Ser Asn Ile Gly Ala Gly
            20                  25                  30

Tyr Asp Val Asn Trp Tyr Gln Gln Leu Pro Gly Thr Ala Pro Lys Leu
        35                  40                  45

Leu Ile Phe His Asn Asn Ile Arg Pro Ser Gly Val Pro Asp Arg Phe
    50                  55                  60

Ser Gly Ser Lys Ser Gly Thr Ser Val Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Trp Val Phe Gly Gly Thr Lys Val Thr Val Leu
            100                 105                 110

<210> SEQ ID NO 138
<211> LENGTH: 14
<212> TYPE: PRT
<213> ORGANISM: Homo sapiens
<220> FEATURE:
<223> OTHER INFORMATION: Bbbt0754 VL CDR1

<400> SEQUENCE: 138

Thr Gly Ser Ser Ser Asn Ile Gly Ala Gly Tyr Asp Val Asn
                5                   10

```
<210> SEQ ID NO 139
<211> LENGTH: 7
<212> TYPE: PRT
<213> ORGANISM: Homo sapiens
<220> FEATURE:
<223> OTHER INFORMATION: Bbbt0754   VL CDR2

<400> SEQUENCE: 139

His Asn Asn Ile Arg Pro Ser
              5

<210> SEQ ID NO 140
<211> LENGTH: 11
<212> TYPE: PRT
<213> ORGANISM: Homo sapiens
<220> FEATURE:
<223> OTHER INFORMATION: Bbbt0754   VL CDR3

<400> SEQUENCE: 140

Gln Ser Tyr Asp Ser Ser Leu Ser Ala Trp Val
              5                  10

<210> SEQ ID NO 141
<211> LENGTH: 22
<212> TYPE: PRT
<213> ORGANISM: Homo sapiens
<220> FEATURE:
<223> OTHER INFORMATION: Bbbt0754   VL FW1

<400> SEQUENCE: 141

Gln Ala Val Leu Thr Gln Pro Ser Ser Val Ser Gly Ala Pro Gly Gln
              5                  10                  15

Arg Val Thr Ile Pro Cys
         20

<210> SEQ ID NO 142
<211> LENGTH: 15
<212> TYPE: PRT
<213> ORGANISM: Homo sapiens
<220> FEATURE:
<223> OTHER INFORMATION: Bbbt0754   VL FW2

<400> SEQUENCE: 142

Trp Tyr Gln Gln Leu Pro Gly Thr Ala Pro Lys Leu Leu Ile Phe
              5                  10                  15

<210> SEQ ID NO 143
<211> LENGTH: 32
<212> TYPE: PRT
<213> ORGANISM: Homo sapiens
<220> FEATURE:
<223> OTHER INFORMATION: Bbbt0754   VL FW3

<400> SEQUENCE: 143

Gly Val Pro Asp Arg Phe Ser Gly Ser Lys Ser Gly Thr Ser Val Ser
              5                  10                  15

Leu Ala Ile Thr Gly Leu Gln Ala Glu Asp Glu Ala Asp Tyr Tyr Cys
         20                  25                  30

<210> SEQ ID NO 144
<211> LENGTH: 10
<212> TYPE: PRT
<213> ORGANISM: Homo sapiens
<220> FEATURE:
<223> OTHER INFORMATION: Bbbt0754   VL FW4
```

<400> SEQUENCE: 144

Phe Gly Gly Gly Thr Lys Val Thr Val Leu
              5                   10

<210> SEQ ID NO 145
<211> LENGTH: 366
<212> TYPE: DNA
<213> ORGANISM: Homo sapiens
<220> FEATURE:
<223> OTHER INFORMATION: Bbbt0674 VH

<400> SEQUENCE: 145
gaggtgcagc tgttggagtc tgggggaggc ttggtacagc ctgggggtc cctgagactc     60 tcctgtgcag cctctggatt caaaattacc cactatacta tgggctgggt ccgccaggct    120
ccagggaagg ggctggagtg gtctctcacgc atcacgtggg gcggtgacaa cacctttttac  180 tccaactccg tgaagggccg gttcaccatc tccagagaca attccaagaa cacgctgtat    240
ctgcaaatga acagcctgag agccgaggac acggccgtat attactgtgc gaaagagact    300
acgaacctct accactacta cggtatgaac gactggggcc ggggcaccct ggtcaccgtc    360
tcgagt                                                               366

<210> SEQ ID NO 146
<211> LENGTH: 122
<212> TYPE: PRT
<213> ORGANISM: Homo sapiens
<220> FEATURE:
<223> OTHER INFORMATION: Bbbt0674 VH

<400> SEQUENCE: 146

Glu Val Gln Leu Leu Glu Ser Gly Gly Gly Leu Val Gln Pro Gly Gly
              5                   10                  15

Ser Leu Arg Leu Ser Cys Ala Ala Ser Gly Phe Lys Ile Thr His Tyr
         20                  25                  30

Thr Met Gly Trp Val Arg Gln Ala Pro Gly Lys Gly Leu Glu Trp Val
     35                  40                  45

Ser Arg Ile Thr Trp Gly Gly Asp Asn Thr Phe Tyr Ser Asn Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Lys Glu Thr Thr Asn Leu Tyr His Tyr Tyr Gly Met Asn Asp Trp
            100                 105                 110

Gly Arg Gly Thr Leu Val Thr Val Ser Ser
        115                 120

<210> SEQ ID NO 147
<211> LENGTH: 5
<212> TYPE: PRT
<213> ORGANISM: Homo sapiens
<220> FEATURE:
<223> OTHER INFORMATION: Bbbt0674 VH CDR1

<400> SEQUENCE: 147

His Tyr Thr Met Gly
              5

<210> SEQ ID NO 148
<211> LENGTH: 17

```
<212> TYPE: PRT
<213> ORGANISM: Homo sapiens
<220> FEATURE:
<223> OTHER INFORMATION: Bbbt0674 VH CDR2

<400> SEQUENCE: 148

Arg Ile Thr Trp Gly Gly Asp Asn Thr Phe Tyr Ser Asn Ser Val Lys
                5                   10                  15

Gly

<210> SEQ ID NO 149
<211> LENGTH: 13
<212> TYPE: PRT
<213> ORGANISM: Homo sapiens
<220> FEATURE:
<223> OTHER INFORMATION: Bbbt0674 VH CDR3

<400> SEQUENCE: 149

Glu Thr Thr Asn Leu Tyr His Tyr Tyr Gly Met Asn Asp
                5                   10

<210> SEQ ID NO 150
<211> LENGTH: 30
<212> TYPE: PRT
<213> ORGANISM: Homo sapiens
<220> FEATURE:
<223> OTHER INFORMATION: Bbbt0674 VH FW1

<400> SEQUENCE: 150

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Lys Ile Thr
            20                  25                  30

<210> SEQ ID NO 151
<211> LENGTH: 14
<212> TYPE: PRT
<213> ORGANISM: Homo sapiens
<220> FEATURE:
<223> OTHER INFORMATION: Bbbt0674 VH FW2

<400> SEQUENCE: 151

Trp Val Arg Gln Ala Pro Gly Lys Gly Leu Glu Trp Val Ser
                5                   10

<210> SEQ ID NO 152
<211> LENGTH: 32
<212> TYPE: PRT
<213> ORGANISM: Homo sapiens
<220> FEATURE:
<223> OTHER INFORMATION: Bbbt0674 VH FW3

<400> SEQUENCE: 152

Arg Phe Thr Ile Ser Arg Asp Asn Ser Lys Asn Thr Leu Tyr Leu Gln
                5                   10                  15

Met Asn Ser Leu Arg Ala Glu Asp Thr Ala Val Tyr Tyr Cys Ala Lys
            20                  25                  30

<210> SEQ ID NO 153
<211> LENGTH: 11
<212> TYPE: PRT
<213> ORGANISM: Homo sapiens
<220> FEATURE:
<223> OTHER INFORMATION: Bbbt0674 VH FW4

<400> SEQUENCE: 153
```

```
<210> SEQ ID NO 154
<211> LENGTH: 330
<212> TYPE: DNA
<213> ORGANISM: Homo sapiens
<220> FEATURE:
<223> OTHER INFORMATION: Bbbt0674 VL

<400> SEQUENCE: 154
cagtctgtgt tgacgcagcc gccctcagtg tctgggaccc ccggggcagag ggtcaccatc    60 tcttgttatg gaagcagctc cgacatcggc aataatttcg tttactggta ccaacaagtc   120
ccaggaatgg cccccaaact cctcatctac aggagtcatc agcggccctc agggggtctct  180 gaccgatttt caggctccaa gtctggcacc tcagcctccc tggccatcag tggactccgg   240
tccgaggatg aggctgatta ttactgtgca acatggggtg acaatctgcg tggttgggtt   300
ttcggcggag ggaccaagct gaccgtccta                                     330

<210> SEQ ID NO 155
<211> LENGTH: 110
<212> TYPE: PRT
<213> ORGANISM: Homo sapiens
<220> FEATURE:
<223> OTHER INFORMATION: Bbbt0674 VL

<400> SEQUENCE: 155

Gln Ser Val Leu Thr Gln Pro Pro Ser Val Ser Gly Thr Pro Gly Gln
                 5                  10                  15
Arg Val Thr Ile Ser Cys Tyr Gly Ser Ser Ser Asp Ile Gly Asn Asn
             20                  25                  30
Phe Val Tyr Trp Tyr Gln Gln Val Pro Gly Met Ala Pro Lys Leu Leu
         35                  40                  45
Ile Tyr Arg Ser His Gln Arg Pro Ser Gly Val Ser Asp Arg Phe Ser
     50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Thr Trp Gly Asp Asn Leu
                 85                  90                  95
Arg Gly Trp Val Phe Gly Gly Gly Thr Lys Leu Thr Val Leu
            100                 105                 110

<210> SEQ ID NO 156
<211> LENGTH: 13
<212> TYPE: PRT
<213> ORGANISM: Homo sapiens
<220> FEATURE:
<223> OTHER INFORMATION: Bbbt0674 VL CDR1

<400> SEQUENCE: 156

Tyr Gly Ser Ser Ser Asp Ile Gly Asn Asn Phe Val Tyr
                 5                  10

<210> SEQ ID NO 157
<211> LENGTH: 7
<212> TYPE: PRT
<213> ORGANISM: Homo sapiens
<220> FEATURE:
<223> OTHER INFORMATION: Bbbt0674 VL CDR2

<400> SEQUENCE: 157
```

Trp Gly Arg Gly Thr Leu Val Thr Val Ser Ser
                 5                  10

Arg Ser His Gln Arg Pro Ser
            5

<210> SEQ ID NO 158
<211> LENGTH: 11
<212> TYPE: PRT
<213> ORGANISM: Homo sapiens
<220> FEATURE:
<223> OTHER INFORMATION: Bbbt0674 VL CDR3

<400> SEQUENCE: 158

Ala Thr Trp Gly Asp Asn Leu Arg Gly Trp Val
            5                   10

<210> SEQ ID NO 159
<211> LENGTH: 22
<212> TYPE: PRT
<213> ORGANISM: Homo sapiens
<220> FEATURE:
<223> OTHER INFORMATION: Bbbt0674 VL FW1

<400> SEQUENCE: 159

Gln Ser Val Leu Thr Gln Pro Pro Ser Val Ser Gly Thr Pro Gly Gln
            5                   10                  15

Arg Val Thr Ile Ser Cys
            20

<210> SEQ ID NO 160
<211> LENGTH: 15
<212> TYPE: PRT
<213> ORGANISM: Homo sapiens
<220> FEATURE:
<223> OTHER INFORMATION: Bbbt0674 VL FW2

<400> SEQUENCE: 160

Trp Tyr Gln Gln Val Pro Gly Met Ala Pro Lys Leu Leu Ile Tyr
            5                   10                  15

<210> SEQ ID NO 161
<211> LENGTH: 32
<212> TYPE: PRT
<213> ORGANISM: Homo sapiens
<220> FEATURE:
<223> OTHER INFORMATION: Bbbt0674 VL FW3

<400> SEQUENCE: 161

Gly Val Ser Asp Arg Phe Ser Gly Ser Lys Ser Gly Thr Ser Ala Ser
            5                   10                  15

Leu Ala Ile Ser Gly Leu Arg Ser Glu Asp Glu Ala Asp Tyr Tyr Cys
            20                  25                  30

<210> SEQ ID NO 162
<211> LENGTH: 10
<212> TYPE: PRT
<213> ORGANISM: Homo sapiens
<220> FEATURE:
<223> OTHER INFORMATION: Bbbt0674 VL FW4

<400> SEQUENCE: 162

Phe Gly Gly Gly Thr Lys Leu Thr Val Leu
            5                   10

<210> SEQ ID NO 163
<211> LENGTH: 360
<212> TYPE: DNA

```
<213> ORGANISM: Homo sapiens
<220> FEATURE:
<223> OTHER INFORMATION: Bbbt0755 VH

<400> SEQUENCE: 163
gaggtgcagc tgttggagtc tgggggaggc ttggtacagc ctgggggtc cctgagactc       60 tcctgtgcag cctctggatt cacctttagc agctatgcca tgagctgggt ccgccaggct      120
ccagggaagg ggctggagtg gtctctcacgc atcacgtggg gcggtgacaa cacctttac      180 tccaactccg tgaagggccg gttcaccatc tccagagaca attccaagaa cacgctgtat      240
ctgcaaatga acagcctgag agccgaggac acggccgtat attactgtgc cagtcattat      300
ggtggctgga tttcactctt tgaccactgg gggcagggga ccacggtcac cgtctcgagt     360

<210> SEQ ID NO 164
<211> LENGTH: 120
<212> TYPE: PRT
<213> ORGANISM: Homo sapiens
<220> FEATURE:
<223> OTHER INFORMATION: Bbbt0755 VH

<400> SEQUENCE: 164

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser His Tyr Gly Gly Trp Ile Ser Leu Phe Asp His Trp Gly Gln
            100                 105                 110

Gly Thr Thr Val Thr Val Ser Ser
        115                 120

<210> SEQ ID NO 165
<211> LENGTH: 5
<212> TYPE: PRT
<213> ORGANISM: Homo sapiens
<220> FEATURE:
<223> OTHER INFORMATION: Bbbt0755 VH CDR1

<400> SEQUENCE: 165

Ser Tyr Ala Met Ser
                 5

<210> SEQ ID NO 166
<211> LENGTH: 17
<212> TYPE: PRT
<213> ORGANISM: Homo sapiens
<220> FEATURE:
<223> OTHER INFORMATION: Bbbt0755 VH CDR2

<400> SEQUENCE: 166

Arg Ile Thr Trp Gly Gly Asp Asn Thr Phe Tyr Ser Asn Ser Val Lys
                 5                  10                  15

Gly
```

<210> SEQ ID NO 167
<211> LENGTH: 11
<212> TYPE: PRT
<213> ORGANISM: Homo sapiens
<220> FEATURE:
<223> OTHER INFORMATION: Bbbt0755 VH CDR3

<400> SEQUENCE: 167

His Tyr Gly Gly Trp Ile Ser Leu Phe Asp His
                 5                  10

<210> SEQ ID NO 168
<211> LENGTH: 30
<212> TYPE: PRT
<213> ORGANISM: Homo sapiens
<220> FEATURE:
<223> OTHER INFORMATION: Bbbt0755 VH FW1

<400> SEQUENCE: 168

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser
             20                  25                  30

<210> SEQ ID NO 169
<211> LENGTH: 14
<212> TYPE: PRT
<213> ORGANISM: Homo sapiens
<220> FEATURE:
<223> OTHER INFORMATION: Bbbt0755 VH FW2

<400> SEQUENCE: 169

Trp Val Arg Gln Ala Pro Gly Lys Gly Leu Glu Trp Val Ser
                 5                  10

<210> SEQ ID NO 170
<211> LENGTH: 32
<212> TYPE: PRT
<213> ORGANISM: Homo sapiens
<220> FEATURE:
<223> OTHER INFORMATION: Bbbt0755 VH FW3

<400> SEQUENCE: 170

Arg Phe Thr Ile Ser Arg Asp Asn Ser Lys Asn Thr Leu Tyr Leu Gln
                 5                  10                  15

Met Asn Ser Leu Arg Ala Glu Asp Thr Ala Val Tyr Tyr Cys Ala Ser
             20                  25                  30

<210> SEQ ID NO 171
<211> LENGTH: 11
<212> TYPE: PRT
<213> ORGANISM: Homo sapiens
<220> FEATURE:
<223> OTHER INFORMATION: Bbbt0755 VH FW4

<400> SEQUENCE: 171

Trp Gly Gln Gly Thr Thr Val Thr Val Ser Ser
                 5                  10

<210> SEQ ID NO 172
<211> LENGTH: 330
<212> TYPE: DNA
<213> ORGANISM: Homo sapiens
<220> FEATURE:
<223> OTHER INFORMATION: Bbbt0755 VL

<400> SEQUENCE: 172

```
caggctgtgc tgactcagcc gtcctcaatt tctggggccc cagggcagag ggtcaccatc    60
tcctgcactg ggaccagctc caacatcggg gcaggtaatg ctgtacactg gtaccagcag   120
cttccaggaa cagcccccag actcctcatc ttcgctgaca accgtcggcc ctcagggttc   180
cctgaccgat tctccgcctc caagtctgcc acctcagcct ccctggccat cactgggctc   240
caggttgacg atgaggctga gtattactgc cagtcgtatg acaccaggct gcgtgtggta   300
ttcggcgggg ggaccaaggt caccgtccta                                     330
```

<210> SEQ ID NO 173
<211> LENGTH: 110
<212> TYPE: PRT
<213> ORGANISM: Homo sapiens
<220> FEATURE:
<223> OTHER INFORMATION: Bbbt0755 VL

<400> SEQUENCE: 173

```
Gln Ala Val Leu Thr Gln Pro Ser Ser Ile Ser Gly Ala Pro Gly Gln
              5                  10                  15
Arg Val Thr Ile Ser Cys Thr Gly Thr Ser Ser Asn Ile Gly Ala Gly
         20                  25                  30
Asn Ala Val His Trp Tyr Gln Gln Leu Pro Gly Thr Ala Pro Arg Leu
     35                  40                  45
Leu Ile Phe Ala Asp Asn Arg Arg Pro Ser Gly Val Pro Asp Arg Phe
 50                  55                  60
Ser Ala Ser Lys Ser Ala Thr Ser Ala Ser Leu Ala Ile Thr Gly Leu
65                  70                  75                  80
Gln Val Asp Asp Glu Ala Glu Tyr Tyr Cys Gln Ser Tyr Asp Thr Arg
                 85                  90                  95
Leu Arg Val Val Phe Gly Gly Gly Thr Lys Val Thr Val Leu
            100                 105                 110
```

<210> SEQ ID NO 174
<211> LENGTH: 14
<212> TYPE: PRT
<213> ORGANISM: Homo sapiens
<220> FEATURE:
<223> OTHER INFORMATION: Bbbt0755 VL CDR1

<400> SEQUENCE: 174

```
Thr Gly Thr Ser Ser Asn Ile Gly Ala Gly Asn Ala Val His
              5                  10
```

<210> SEQ ID NO 175
<211> LENGTH: 7
<212> TYPE: PRT
<213> ORGANISM: Homo sapiens
<220> FEATURE:
<223> OTHER INFORMATION: Bbbt0755 VL CDR2

<400> SEQUENCE: 175

```
Ala Asp Asn Arg Arg Pro Ser
              5
```

<210> SEQ ID NO 176
<211> LENGTH: 10
<212> TYPE: PRT
<213> ORGANISM: Homo sapiens
<220> FEATURE:
<223> OTHER INFORMATION: Bbbt0755 VL CDR3

<400> SEQUENCE: 176

Gln Ser Tyr Asp Thr Arg Leu Arg Val Val
                5                   10

<210> SEQ ID NO 177
<211> LENGTH: 22
<212> TYPE: PRT
<213> ORGANISM: Homo sapiens
<220> FEATURE:
<223> OTHER INFORMATION: Bbbt0755  VL FW1

<400> SEQUENCE: 177

Gln Ala Val Leu Thr Gln Pro Ser Ser Ile Ser Gly Ala Pro Gly Gln
                5                   10                  15

Arg Val Thr Ile Ser Cys
            20

<210> SEQ ID NO 178
<211> LENGTH: 15
<212> TYPE: PRT
<213> ORGANISM: Homo sapiens
<220> FEATURE:
<223> OTHER INFORMATION: Bbbt0755  VL FW2

<400> SEQUENCE: 178

Trp Tyr Gln Gln Leu Pro Gly Thr Ala Pro Arg Leu Leu Ile Phe
                5                   10                  15

<210> SEQ ID NO 179
<211> LENGTH: 32
<212> TYPE: PRT
<213> ORGANISM: Homo sapiens
<220> FEATURE:
<223> OTHER INFORMATION: Bbbt0755  VL FW3

<400> SEQUENCE: 179

Gly Val Pro Asp Arg Phe Ser Ala Ser Lys Ser Ala Thr Ser Ala Ser
                5                   10                  15

Leu Ala Ile Thr Gly Leu Gln Val Asp Asp Glu Ala Glu Tyr Tyr Cys
            20                  25                  30

<210> SEQ ID NO 180
<211> LENGTH: 10
<212> TYPE: PRT
<213> ORGANISM: Homo sapiens
<220> FEATURE:
<223> OTHER INFORMATION: Bbbt0755  VL FW4

<400> SEQUENCE: 180

Phe Gly Gly Gly Thr Lys Val Thr Val Leu
                5                   10

<210> SEQ ID NO 181
<211> LENGTH: 360
<212> TYPE: DNA
<213> ORGANISM: Homo sapiens
<220> FEATURE:
<223> OTHER INFORMATION: Bbbt0643  VH

<400> SEQUENCE: 181
gaggtgcagc tgcaggagtc tgggggaggc ttggtacagc ctggggggtc cctgagactc        60
tcctgtgcag cctctggatt caaaattacc cactatacta tgggctgggt ccgccaggct       120
ccagggaagg ggctggagtg ggtctcagct attagtggta gtggtggtag cacatactac       180
gcagactccg tgaagggccg gttcaccatc tccagagaca attccaagaa cacgctgtat    240
ctgcaaatga acagcctgag agccgaggac acggccgtgt attactgtgc gagaggggt    300 gggactatat cagctcggtt cgaccctgg gggcaaggga ccacggtcac cgtctcgagt    360

```
<210> SEQ ID NO 182
<211> LENGTH: 120
<212> TYPE: PRT
<213> ORGANISM: Homo sapiens
<220> FEATURE:
<223> OTHER INFORMATION: Bbbt0643 VH

<400> SEQUENCE: 182
```

Glu Val Gln Leu Gln Glu Ser Gly Gly Gly Leu Val Gln Pro Gly Gly
              5                   10                  15

Ser Leu Arg Leu Ser Cys Ala Ala Ser Gly Phe Lys Ile Thr His Tyr
         20                  25                  30

Thr Met Gly Trp Val Arg Gln Ala Pro Gly Lys Gly Leu Glu Trp Val
     35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Gly Gly Gly Thr Ile Ser Ala Arg Phe Asp Pro Trp Gly Gln
            100                 105                 110

Gly Thr Thr Val Thr Val Ser Ser
        115                 120

```
<210> SEQ ID NO 183
<211> LENGTH: 5
<212> TYPE: PRT
<213> ORGANISM: Homo sapiens
<220> FEATURE:
<223> OTHER INFORMATION: Bbbt0643 VH CDR1

<400> SEQUENCE: 183
```

His Tyr Thr Met Gly
              5

```
<210> SEQ ID NO 184
<211> LENGTH: 17
<212> TYPE: PRT
<213> ORGANISM: Homo sapiens
<220> FEATURE:
<223> OTHER INFORMATION: Bbbt0643 VH CDR2

<400> SEQUENCE: 184
```

Ala Ile Ser Gly Ser Gly Gly Ser Thr Tyr Tyr Ala Asp Ser Val Lys
              5                   10                  15

Gly

```
<210> SEQ ID NO 185
<211> LENGTH: 11
<212> TYPE: PRT
<213> ORGANISM: Homo sapiens
<220> FEATURE:
<223> OTHER INFORMATION: Bbbt0643 VH CDR3

<400> SEQUENCE: 185
```

-continued

Gly Gly Gly Thr Ile Ser Ala Arg Phe Asp Pro
                5                   10

<210> SEQ ID NO 186
<211> LENGTH: 30
<212> TYPE: PRT
<213> ORGANISM: Homo sapiens
<220> FEATURE:
<223> OTHER INFORMATION: Bbbt0643 VH FW1

<400> SEQUENCE: 186

Glu Val Gln Leu Gln Glu Ser Gly Gly Gly Leu Val Gln Pro Gly Gly
                5                   10                  15

Ser Leu Arg Leu Ser Cys Ala Ala Ser Gly Phe Lys Ile Thr
            20                  25                  30

<210> SEQ ID NO 187
<211> LENGTH: 14
<212> TYPE: PRT
<213> ORGANISM: Homo sapiens
<220> FEATURE:
<223> OTHER INFORMATION: Bbbt0643 VH FW2

<400> SEQUENCE: 187

Trp Val Arg Gln Ala Pro Gly Lys Gly Leu Glu Trp Val Ser
                5                   10

<210> SEQ ID NO 188
<211> LENGTH: 32
<212> TYPE: PRT
<213> ORGANISM: Homo sapiens
<220> FEATURE:
<223> OTHER INFORMATION: Bbbt0643 VH FW3

<400> SEQUENCE: 188

Arg Phe Thr Ile Ser Arg Asp Asn Ser Lys Asn Thr Leu Tyr Leu Gln
                5                   10                  15

Met Asn Ser Leu Arg Ala Glu Asp Thr Ala Val Tyr Tyr Cys Ala Arg
            20                  25                  30

<210> SEQ ID NO 189
<211> LENGTH: 11
<212> TYPE: PRT
<213> ORGANISM: Homo sapiens
<220> FEATURE:
<223> OTHER INFORMATION: Bbbt0643 VH FW4

<400> SEQUENCE: 189

Trp Gly Gln Gly Thr Thr Val Thr Val Ser Ser
                5                   10

<210> SEQ ID NO 190
<211> LENGTH: 324
<212> TYPE: DNA
<213> ORGANISM: Homo sapiens
<220> FEATURE:
<223> OTHER INFORMATION: Bbbt0643 VL

<400> SEQUENCE: 190
tcttctgagc tgactcagga ccctgctgtg tctgtggcct tgggacagac agtcaggatc      60
acatgccaag gagacagcct cagaagctat tatgcaagct ggtaccagca gaagccagga     120
caggcccctg tacttgtcat ctatggtaaa acaaccggc cctcagggat cccagaccga     180
ttctctggct ccagctcagg aaacacagct tccttgacca tcactggggc tcaggcggaa     240

```
gatgaggctg actattactg taactcccgg gacagcagtg gtaaccatgt ggtattcggc    300
ggagggacca agctgaccgt ccta                                          324
```

<210> SEQ ID NO 191
<211> LENGTH: 108
<212> TYPE: PRT
<213> ORGANISM: Homo sapiens
<220> FEATURE:
<223> OTHER INFORMATION: Bbbt0643 VL

<400> SEQUENCE: 191

Ser Ser Glu Leu Thr Gln Asp Pro Ala Val Ser Val Ala Leu Gly Gln
              5                  10                  15

Thr Val Arg Ile Thr Cys Gln Gly Asp Ser Leu Arg Ser Tyr Tyr Ala
         20                  25                  30

Ser Trp Tyr Gln Gln Lys Pro Gly Gln Ala Pro Val Leu Val Ile Tyr
     35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                 85                  90                  95

Val Val Phe Gly Gly Gly Thr Lys Leu Thr Val Leu
            100                 105

<210> SEQ ID NO 192
<211> LENGTH: 11
<212> TYPE: PRT
<213> ORGANISM: Homo sapiens
<220> FEATURE:
<223> OTHER INFORMATION: Bbbt0643 VL CDR1

<400> SEQUENCE: 192

Gln Gly Asp Ser Leu Arg Ser Tyr Tyr Ala Ser
              5                  10

<210> SEQ ID NO 193
<211> LENGTH: 7
<212> TYPE: PRT
<213> ORGANISM: Homo sapiens
<220> FEATURE:
<223> OTHER INFORMATION: Bbbt0643 VL CDR2

<400> SEQUENCE: 193

Gly Lys Asn Asn Arg Pro Ser
              5

<210> SEQ ID NO 194
<211> LENGTH: 11
<212> TYPE: PRT
<213> ORGANISM: Homo sapiens
<220> FEATURE:
<223> OTHER INFORMATION: Bbbt0643 VL CDR3

<400> SEQUENCE: 194

Asn Ser Arg Asp Ser Ser Gly Asn His Val Val
              5                  10

<210> SEQ ID NO 195
<211> LENGTH: 22
<212> TYPE: PRT
<213> ORGANISM: Homo sapiens
<220> FEATURE:
<223> OTHER INFORMATION: Bbbt0643 VL FW1

<400> SEQUENCE: 195

Ser Ser Glu Leu Thr Gln Asp Pro Ala Val Ser Val Ala Leu Gly Gln
1               5                   10                  15
Thr Val Arg Ile Thr Cys
            20

<210> SEQ ID NO 196
<211> LENGTH: 15
<212> TYPE: PRT
<213> ORGANISM: Homo sapiens
<220> FEATURE:
<223> OTHER INFORMATION: Bbbt0643 VL FW2

<400> SEQUENCE: 196

Trp Tyr Gln Gln Lys Pro Gly Gln Ala Pro Val Leu Val Ile Tyr
1               5                   10                  15

<210> SEQ ID NO 197
<211> LENGTH: 32
<212> TYPE: PRT
<213> ORGANISM: Homo sapiens
<220> FEATURE:
<223> OTHER INFORMATION: Bbbt0643 VL FW3

<400> SEQUENCE: 197

Gly Ile Pro Asp Arg Phe Ser Gly Ser Ser Ser Gly Asn Thr Ala Ser
1               5                   10                  15
Leu Thr Ile Thr Gly Ala Gln Ala Glu Asp Glu Ala Asp Tyr Tyr Cys
            20                  25                  30

<210> SEQ ID NO 198
<211> LENGTH: 10
<212> TYPE: PRT
<213> ORGANISM: Homo sapiens
<220> FEATURE:
<223> OTHER INFORMATION: Bbbt0643 VL FW4

<400> SEQUENCE: 198

Phe Gly Gly Gly Thr Lys Leu Thr Val Leu
1               5                   10

<210> SEQ ID NO 199
<211> LENGTH: 366
<212> TYPE: DNA
<213> ORGANISM: Homo sapiens
<220> FEATURE:
<223> OTHER INFORMATION: Bbbt0351

<400> SEQUENCE: 199
gaagttcaac tgcaggcgtc cggcggtggc ctggtgcagg ctggcggctc tctgcgtctg      60
tcctgtgctg ccagcggctt taaaatcact cactatacta tgggctggtt ccgccaggca     120
ccgggcaaag agcgtgaatt cgtgagccgc atcacctggg gcggtgacaa cacctttta c    180 tccaactccg ttaagggtcg ttttactatc tctcgtgata cgctaaaaa cacgttt tac     240 ctgcagatga cagcctgaa accagaggac actgctgact actattgtgc tgcaggttcc      300
gcctctacgg ctgacccact gcgcgtcgac tattggggca aaggcaccca ggtgaccgtt     360
tcttcc                                                                366

<210> SEQ ID NO 200

```
<211> LENGTH: 122
<212> TYPE: PRT
<213> ORGANISM: Homo sapiens
<220> FEATURE:
<223> OTHER INFORMATION: Bbbt0351

<400> SEQUENCE: 200

Glu Val Gln Leu Gln Ala Ser Gly Gly Gly Leu Val Gln Ala Gly Gly
                 5                  10                  15
Ser Leu Arg Leu Ser Cys Ala Ala Ser Gly Phe Lys Ile Thr His Tyr
             20                  25                  30
Thr Met Gly Trp Phe Arg Gln Ala Pro Gly Lys Glu Arg Glu Phe Val
         35                  40                  45
Ser Arg Ile Thr Trp Gly Gly Asp Asn Thr Phe Tyr Ser Asn Ser Val
     50                  55                  60
Lys Gly Arg Phe Thr Ile Ser Arg Asp Asn Ala Lys Asn Thr Val Tyr
 65                  70                  75                  80
Leu Gln Met Asn Ser Leu Lys Pro Glu Asp Thr Ala Asp Tyr Tyr Cys
                 85                  90                  95
Ala Ala Gly Ser Ala Ser Thr Ala Asp Pro Leu Arg Val Asp Tyr Trp
            100                 105                 110
Gly Lys Gly Thr Gln Val Thr Val Ser Ser
            115                 120

<210> SEQ ID NO 201
<211> LENGTH: 5
<212> TYPE: PRT
<213> ORGANISM: Homo sapiens
<220> FEATURE:
<223> OTHER INFORMATION: Bbbt0351

<400> SEQUENCE: 201

His Tyr Thr Met Gly
                 5

<210> SEQ ID NO 202
<211> LENGTH: 17
<212> TYPE: PRT
<213> ORGANISM: Homo sapiens
<220> FEATURE:
<223> OTHER INFORMATION: Bbbt0351

<400> SEQUENCE: 202

Arg Ile Thr Trp Gly Gly Asp Asn Thr Phe Tyr Ser Asn Ser Val Lys
                 5                  10                  15
Gly

<210> SEQ ID NO 203
<211> LENGTH: 13
<212> TYPE: PRT
<213> ORGANISM: Homo sapiens
<220> FEATURE:
<223> OTHER INFORMATION: Bbbt0351

<400> SEQUENCE: 203

Gly Ser Ala Ser Thr Ala Asp Pro Leu Arg Val Asp Tyr
                 5                  10

<210> SEQ ID NO 204
<211> LENGTH: 30
<212> TYPE: PRT
<213> ORGANISM: Homo sapiens
<220> FEATURE:
```

<223> OTHER INFORMATION: Bbbt0351

<400> SEQUENCE: 204

Glu Val Gln Leu Gln Ala Ser Gly Gly Gly Leu Val Gln Ala Gly Gly
 1               5                  10                  15
Ser Leu Arg Leu Ser Cys Ala Ala Ser Gly Phe Lys Ile Thr
            20                  25                  30

<210> SEQ ID NO 205
<211> LENGTH: 14
<212> TYPE: PRT
<213> ORGANISM: Homo sapiens
<220> FEATURE:
<223> OTHER INFORMATION: Bbbt0351

<400> SEQUENCE: 205

Trp Phe Arg Gln Ala Pro Gly Lys Glu Arg Glu Phe Val Ser
 1               5                  10

<210> SEQ ID NO 206
<211> LENGTH: 32
<212> TYPE: PRT
<213> ORGANISM: Homo sapiens
<220> FEATURE:
<223> OTHER INFORMATION: Bbbt0351

<400> SEQUENCE: 206

Arg Phe Thr Ile Ser Arg Asp Asn Ala Lys Asn Thr Val Tyr Leu Gln
 1               5                  10                  15
Met Asn Ser Leu Lys Pro Glu Asp Thr Ala Asp Tyr Tyr Cys Ala Ala
            20                  25                  30

<210> SEQ ID NO 207
<211> LENGTH: 11
<212> TYPE: PRT
<213> ORGANISM: Homo sapiens
<220> FEATURE:
<223> OTHER INFORMATION: Bbbt0351

<400> SEQUENCE: 207

Trp Gly Lys Gly Thr Gln Val Thr Val Ser Ser
 1               5                  10

<210> SEQ ID NO 208
<211> LENGTH: 387
<212> TYPE: DNA
<213> ORGANISM: Homo sapiens
<220> FEATURE:
<223> OTHER INFORMATION: Bbbt0579

<400> SEQUENCE: 208
ggggtgcagc tggtgcagtc tgggggaggc gtggtccagc ctggagggtc cctgagactc      60
tcctgtgcag cctctggatt caccttcagt agctatgcta tgcactgggt ccgccaggct     120
ccaggcaagg ggctggagtg gtggcagtt atatcatatg atggaagcaa taaatactac     180
gcagactccg tgaagggccg attcaccatc tccagagaca attccaagaa cacgctgtat     240
ctgcaaatga acagcctgag agctgaggac acggctgtgt attactgtgc gagagatgat     300
attgtagtag taccagctgc taatgcgaac tactactact actacatgga cgtctggggc     360
caaggaacca cagtcaccgt ctcctca                                        387

<210> SEQ ID NO 209
<211> LENGTH: 129

```
<212> TYPE: PRT
<213> ORGANISM: Homo sapiens
<220> FEATURE:
<223> OTHER INFORMATION: Bbbt0579

<400> SEQUENCE: 209

Gly Val Gln Leu Val Gln Ser Gly Gly Val Val Gln Pro Gly Arg
                 5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Ile Val Val Pro Ala Ala Asn Ala Asn Tyr Tyr
            100                 105                 110

Tyr Tyr Tyr Met Asp Val Trp Gly Gln Gly Thr Thr Val Thr Val Ser
        115                 120                 125

Ser

<210> SEQ ID NO 210
<211> LENGTH: 5
<212> TYPE: PRT
<213> ORGANISM: Homo sapiens
<220> FEATURE:
<223> OTHER INFORMATION: Bbbt0579

<400> SEQUENCE: 210

Ser Tyr Ala Met His
                 5

<210> SEQ ID NO 211
<211> LENGTH: 17
<212> TYPE: PRT
<213> ORGANISM: Homo sapiens
<220> FEATURE:
<223> OTHER INFORMATION: Bbbt0579

<400> SEQUENCE: 211

Val Ile Ser Tyr Asp Gly Ser Asn Lys Tyr Tyr Ala Asp Ser Val Lys
                 5                  10                  15

Gly

<210> SEQ ID NO 212
<211> LENGTH: 20
<212> TYPE: PRT
<213> ORGANISM: Homo sapiens
<220> FEATURE:
<223> OTHER INFORMATION: Bbbt0579

<400> SEQUENCE: 212

Asp Asp Ile Val Val Pro Ala Ala Asn Ala Asn Tyr Tyr Tyr Tyr
                 5                  10                  15

Tyr Met Asp Val
            20

<210> SEQ ID NO 213
```

```
<211> LENGTH: 30
<212> TYPE: PRT
<213> ORGANISM: Homo sapiens
<220> FEATURE:
<223> OTHER INFORMATION: Bbbt0579

<400> SEQUENCE: 213

Gly Val Gln Leu Val Gln Ser Gly Gly Gly Val Val Gln Pro Gly Arg
 1               5                  10                  15
Ser Leu Arg Leu Ser Cys Ala Ala Ser Gly Phe Thr Phe Ser
             20                  25                  30

<210> SEQ ID NO 214
<211> LENGTH: 14
<212> TYPE: PRT
<213> ORGANISM: Homo sapiens
<220> FEATURE:
<223> OTHER INFORMATION: Bbbt0579

<400> SEQUENCE: 214

Trp Val Arg Gln Ala Pro Gly Lys Gly Leu Glu Trp Val Ala
 1               5                  10

<210> SEQ ID NO 215
<211> LENGTH: 32
<212> TYPE: PRT
<213> ORGANISM: Homo sapiens
<220> FEATURE:
<223> OTHER INFORMATION: Bbbt0579

<400> SEQUENCE: 215

Arg Phe Thr Ile Ser Arg Asp Asn Ser Lys Asn Thr Leu Tyr Leu Gln
 1               5                  10                  15
Met Asn Ser Leu Arg Ala Glu Asp Thr Ala Val Tyr Tyr Cys Ala Arg
             20                  25                  30

<210> SEQ ID NO 216
<211> LENGTH: 11
<212> TYPE: PRT
<213> ORGANISM: Homo sapiens
<220> FEATURE:
<223> OTHER INFORMATION: Bbbt0579

<400> SEQUENCE: 216

Trp Gly Gln Gly Thr Thr Val Thr Val Ser Ser
 1               5                  10

<210> SEQ ID NO 217
<211> LENGTH: 321
<212> TYPE: DNA
<213> ORGANISM: Homo sapiens
<220> FEATURE:
<223> OTHER INFORMATION: Bbbt0579

<400> SEQUENCE: 217
gacatccaga tgacccagtc tccatccttc ctgtctgcat ctgtaggaga cagagtcacc      60
atcacttgcc gggccagtca gggcattaac aattatttag cctggtatca gcaaaaacca     120
gggagagccc ctaagctcct gatctacgct gcatccagtt tacaaagtgg ggtcccatca     180
aggttcagcg gcagtggatc tgggacagat ttcactctca ccatcagcag cctgcagcct     240
gaagattttg caacttatta ctgtctccaa gattccgatt atcccctcac tttcggcgga     300
gggaccaagc tggagatcaa a                                              321
```

-continued

<210> SEQ ID NO 218
<211> LENGTH: 107
<212> TYPE: PRT
<213> ORGANISM: Homo sapiens
<220> FEATURE:
<223> OTHER INFORMATION: Bbbt0579

<400> SEQUENCE: 218

Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Asn Asn Tyr
            20                  25                  30

Leu Ala Trp Tyr Gln Gln Lys Pro Gly Arg Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Ser Asp Tyr Pro Leu
                85                  90                  95

Thr Phe Gly Gly Gly Thr Lys Leu Glu Ile Lys
            100                 105

<210> SEQ ID NO 219
<211> LENGTH: 11
<212> TYPE: PRT
<213> ORGANISM: Homo sapiens
<220> FEATURE:
<223> OTHER INFORMATION: Bbbt0579

<400> SEQUENCE: 219

Arg Ala Ser Gln Gly Ile Asn Asn Tyr Leu Ala
 1               5                  10

<210> SEQ ID NO 220
<211> LENGTH: 7
<212> TYPE: PRT
<213> ORGANISM: Homo sapiens
<220> FEATURE:
<223> OTHER INFORMATION: Bbbt0579

<400> SEQUENCE: 220

Ala Ala Ser Ser Leu Gln Ser
 1               5

<210> SEQ ID NO 221
<211> LENGTH: 9
<212> TYPE: PRT
<213> ORGANISM: Homo sapiens
<220> FEATURE:
<223> OTHER INFORMATION: Bbbt0579

<400> SEQUENCE: 221

Leu Gln Asp Ser Asp Tyr Pro Leu Thr
 1               5

<210> SEQ ID NO 222
<211> LENGTH: 23
<212> TYPE: PRT
<213> ORGANISM: Homo sapiens
<220> FEATURE:
<223> OTHER INFORMATION: Bbbt0579

<400> SEQUENCE: 222

```
Asp Ile Gln Met Thr Gln Ser Pro Ser Phe Leu Ser Ala Ser Val Gly
  5                    10                  15

Asp Arg Val Thr Ile Thr Cys
         20
```

<210> SEQ ID NO 223
<211> LENGTH: 15
<212> TYPE: PRT
<213> ORGANISM: Homo sapiens
<220> FEATURE:
<223> OTHER INFORMATION: Bbbt0579

<400> SEQUENCE: 223

```
Trp Tyr Gln Gln Lys Pro Gly Arg Ala Pro Lys Leu Leu Ile Tyr
  5                    10                  15
```

<210> SEQ ID NO 224
<211> LENGTH: 32
<212> TYPE: PRT
<213> ORGANISM: Homo sapiens
<220> FEATURE:
<223> OTHER INFORMATION: Bbbt0579

<400> SEQUENCE: 224

```
Gly Val Pro Ser Arg Phe Ser Gly Ser Gly Ser Gly Thr Asp Phe Thr
  5                    10                  15

Leu Thr Ile Ser Ser Leu Gln Pro Glu Asp Phe Ala Thr Tyr Tyr Cys
         20                  25              30
```

<210> SEQ ID NO 225
<211> LENGTH: 10
<212> TYPE: PRT
<213> ORGANISM: Homo sapiens
<220> FEATURE:
<223> OTHER INFORMATION: Bbbt0579

<400> SEQUENCE: 225

```
Phe Gly Gly Gly Thr Lys Leu Glu Ile Lys
  5                    10
```

<210> SEQ ID NO 226
<211> LENGTH: 128
<212> TYPE: PRT
<213> ORGANISM: Homo sapiens
<220> FEATURE:
<223> OTHER INFORMATION: Bbbt0671

<400> SEQUENCE: 226

```
Glu Val His Leu Leu Glu Ser Gly Gly Gly Leu Val Gln Pro Gly Gly
  5                    10                  15

Ser Leu Arg Leu Ser Cys Ala Ala Ser Gly Phe Thr Phe Ser Ser Tyr
         20                  25              30

Ala Met Ser Trp Val Arg Gln Ala Pro Gly Lys Gly Leu Glu Trp Val
      35              40                  45

Ser Ala Ile Ser Gly Ser Gly Gly Ser Thr Tyr Tyr Ala His Ser Val
   50                  55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
             85                  90                  95

Ala Lys Asn Tyr Tyr Tyr Asp Ser Ala Tyr Tyr Val Gly Ser
           100                 105                 110
```

```
              Asp Tyr Phe Asp Tyr Trp Gly Gln Gly Thr Met Val Thr Val Ser Ser
                      115                 120                 125
```

<210> SEQ ID NO 227
<211> LENGTH: 110
<212> TYPE: PRT
<213> ORGANISM: Homo sapiens
<220> FEATURE:
<223> OTHER INFORMATION: Bbbt0671

<400> SEQUENCE: 227

```
Gln Ser Ala Leu Thr Gln Pro Ala Ser Val Ser Gly Ser Pro Gly Gln
                  5                  10                  15

Ser Ile Thr Ile Ser Cys Thr Ala Thr Ser Ser Asn Val Gly Ala Tyr
             20                  25                  30

Asn Phe Val Ser Trp Tyr Gln Gln His Pro Gly Lys Ala Pro Lys Val
         35                  40                  45

Leu Ile Tyr Arg Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Asp Glu Ala Asp Tyr Tyr Cys Ser Ser Tyr Thr Thr Asp
                  85                  90                  95

Tyr Ile Trp Val Phe Gly Gly Gly Thr Lys Leu Thr Val Leu
             100                 105                 110
```

<210> SEQ ID NO 228
<211> LENGTH: 108
<212> TYPE: PRT
<213> ORGANISM: Artificial Sequence
<220> FEATURE:
<223> OTHER INFORMATION: VL Consensus Sequence
<220> FEATURE:
<221> NAME/KEY: MISC_FEATURE
<222> LOCATION: (15)..(15)
<223> OTHER INFORMATION: Xaa is Arg or Gly
<220> FEATURE:
<221> NAME/KEY: MISC_FEATURE
<222> LOCATION: (28)..(28)
<223> OTHER INFORMATION: Xaa is Thr or Arg
<220> FEATURE:
<221> NAME/KEY: MISC_FEATURE
<222> LOCATION: (29)..(29)
<223> OTHER INFORMATION: Xaa is Ser, Arg or Thr
<220> FEATURE:
<221> NAME/KEY: MISC_FEATURE
<222> LOCATION: (32)..(32)
<223> OTHER INFORMATION: Xaa is Ala or Thr
<220> FEATURE:
<221> NAME/KEY: MISC_FEATURE
<222> LOCATION: (33)..(33)
<223> OTHER INFORMATION: Xaa is Asn or Ser
<220> FEATURE:
<221> NAME/KEY: MISC_FEATURE
<222> LOCATION: (37)..(37)
<223> OTHER INFORMATION: Xaa is His or Gln
<220> FEATURE:
<221> NAME/KEY: MISC_FEATURE
<222> LOCATION: (47)..(47)
<223> OTHER INFORMATION: Xaa is Met or Ile
<220> FEATURE:
<221> NAME/KEY: MISC_FEATURE
<222> LOCATION: (50)..(50)
<223> OTHER INFORMATION: Xaa is Lys or Glu
<220> FEATURE:
<221> NAME/KEY: MISC_FEATURE
<222> LOCATION: (51)..(51)
<223> OTHER INFORMATION: Xaa is Asn or Asp
<220> FEATURE:
<221> NAME/KEY: MISC_FEATURE

```
<222> LOCATION: (57)..(57)
<223> OTHER INFORMATION: Xaa is Val or Ile
<220> FEATURE:
<221> NAME/KEY: MISC_FEATURE
<222> LOCATION: (65)..(65)
<223> OTHER INFORMATION: Xaa is Ser or Arg
<220> FEATURE:
<221> NAME/KEY: MISC_FEATURE
<222> LOCATION: (68)..(68)
<223> OTHER INFORMATION: Xaa is Asn or Thr
<220> FEATURE:
<221> NAME/KEY: MISC_FEATURE
<222> LOCATION: (92)..(92)
<223> OTHER INFORMATION: Xaa is Ser or Asn
<220> FEATURE:
<221> NAME/KEY: MISC_FEATURE
<222> LOCATION: (93)..(93)
<223> OTHER INFORMATION: Xaa is Ser or Thr
<220> FEATURE:
<221> NAME/KEY: MISC_FEATURE
<222> LOCATION: (95)..(95)
<223> OTHER INFORMATION: Xaa is Asn, Lys or His
<220> FEATURE:
<221> NAME/KEY: MISC_FEATURE
<222> LOCATION: (96)..(96)
<223> OTHER INFORMATION: Xaa is His or Pro
<220> FEATURE:
<221> NAME/KEY: MISC_FEATURE
<222> LOCATION: (97)..(97)
<223> OTHER INFORMATION: Xaa is Val or Trp

<400> SEQUENCE: 228

Ser Ser Glu Leu Thr Gln Asp Pro Ala Val Ser Val Ala Leu Xaa Gln
                5                   10                  15

Thr Val Arg Ile Thr Cys Gln Gly Asp Ser Leu Xaa Xaa Tyr Tyr Xaa
            20                  25                  30

Xaa Trp Tyr Gln Xaa Lys Pro Gly Gln Ala Pro Val Leu Val Xaa Tyr
        35                  40                  45

Gly Xaa Xaa Asn Arg Pro Ser Gly Xaa Pro Asp Arg Phe Ser Gly Ser
    50                  55                  60

Xaa Ser Gly Xaa Thr Ala Ser Leu Thr Ile Thr Gly Ala Gln Ala Glu
65                  70                  75                  80

Asp Glu Ala Asp Tyr Tyr Cys Asn Ser Arg Asp Xaa Xaa Gly Xaa Xaa
                85                  90                  95

Xaa Val Phe Gly Gly Gly Thr Lys Leu Thr Val Leu
            100                 105

<210> SEQ ID NO 229
<211> LENGTH: 11
<212> TYPE: PRT
<213> ORGANISM: Artificial Sequence
<220> FEATURE:
<223> OTHER INFORMATION: LCDR1 Consensus Sequence
<220> FEATURE:
<221> NAME/KEY: MISC_FEATURE
<222> LOCATION: (6)..(6)
<223> OTHER INFORMATION: Xaa is Thr or Arg
<220> FEATURE:
<221> NAME/KEY: MISC_FEATURE
<222> LOCATION: (7)..(7)
<223> OTHER INFORMATION: Xaa is Ser, Arg or Thr
<220> FEATURE:
<221> NAME/KEY: MISC_FEATURE
<222> LOCATION: (10)..(10)
<223> OTHER INFORMATION: Xaa is Ala or Thr
<220> FEATURE:
<221> NAME/KEY: MISC_FEATURE
<222> LOCATION: (11)..(11)
<223> OTHER INFORMATION: Xaa is Asn or Ser

<400> SEQUENCE: 229
```

```
Gln Gly Asp Ser Leu Xaa Xaa Tyr Tyr Xaa Xaa
                5                   10

<210> SEQ ID NO 230
<211> LENGTH: 7
<212> TYPE: PRT
<213> ORGANISM: Artificial Sequence
<220> FEATURE:
<223> OTHER INFORMATION: LCDR2 Consensus Sequence
<220> FEATURE:
<221> NAME/KEY: MISC_FEATURE
<222> LOCATION: (2)..(2)
<223> OTHER INFORMATION: Xaa is Lys or Glu
<220> FEATURE:
<221> NAME/KEY: MISC_FEATURE
<222> LOCATION: (3)..(3)
<223> OTHER INFORMATION: Xaa is Asn or Asp

<400> SEQUENCE: 230

Gly Xaa Xaa Asn Arg Pro Ser
                5

<210> SEQ ID NO 231
<211> LENGTH: 11
<212> TYPE: PRT
<213> ORGANISM: Artificial Sequence
<220> FEATURE:
<223> OTHER INFORMATION: LCDR3 Consensus Sequence
<220> FEATURE:
<221> NAME/KEY: MISC_FEATURE
<222> LOCATION: (5)..(5)
<223> OTHER INFORMATION: Xaa is Ser or Asn
<220> FEATURE:
<221> NAME/KEY: MISC_FEATURE
<222> LOCATION: (6)..(6)
<223> OTHER INFORMATION: Xaa is Ser or Thr
<220> FEATURE:
<221> NAME/KEY: MISC_FEATURE
<222> LOCATION: (8)..(8)
<223> OTHER INFORMATION: Xaa is Asn, Lys or His
<220> FEATURE:
<221> NAME/KEY: MISC_FEATURE
<222> LOCATION: (9)..(9)
<223> OTHER INFORMATION: Xaa is His or Pro
<220> FEATURE:
<221> NAME/KEY: MISC_FEATURE
<222> LOCATION: (10)..(10)
<223> OTHER INFORMATION: Xaa is Val or Trp

<400> SEQUENCE: 231

Asn Ser Arg Asp Xaa Xaa Gly Xaa Xaa Xaa Val
                5                   10

<210> SEQ ID NO 232
<211> LENGTH: 5
<212> TYPE: PRT
<213> ORGANISM: Artificial Sequence
<220> FEATURE:
<223> OTHER INFORMATION: Linker

<400> SEQUENCE: 232

Gly Gly Gly Gly Ser
                5

<210> SEQ ID NO 233
<211> LENGTH: 6
<212> TYPE: PRT
<213> ORGANISM: Artificial Sequence
<220> FEATURE:
<223> OTHER INFORMATION: Linker
```

```
<400> SEQUENCE: 233

Ser Gly Gly Gly Gly Ser
                    5

<210> SEQ ID NO 234
<211> LENGTH: 15
<212> TYPE: PRT
<213> ORGANISM: Artificial Sequence
<220> FEATURE:
<223> OTHER INFORMATION: Linker

<400> SEQUENCE: 234

Gly Gly Gly Gly Ser Gly Gly Gly Gly Ser Gly Gly Gly Gly Ser
                    5                  10                  15

<210> SEQ ID NO 235
<211> LENGTH: 14
<212> TYPE: PRT
<213> ORGANISM: Artificial Sequence
<220> FEATURE:
<223> OTHER INFORMATION: Linker

<400> SEQUENCE: 235

Gly Gly Gly Gly Ser Gly Gly Gly Gly Ser Gly Gly Gly Gly
                    5                  10

<210> SEQ ID NO 236
<211> LENGTH: 17
<212> TYPE: PRT
<213> ORGANISM: Artificial Sequence
<220> FEATURE:
<223> OTHER INFORMATION: Linker

<400> SEQUENCE: 236

Gly Gly Gly Gly Ser Gly Gly Gly Gly Ser Gly Gly Gly Gly Ser Ala
                    5                  10                  15

Leu

<210> SEQ ID NO 237
<211> LENGTH: 16
<212> TYPE: PRT
<213> ORGANISM: Artificial Sequence
<220> FEATURE:
<223> OTHER INFORMATION: Linker

<400> SEQUENCE: 237

Gly Gly Gly Gly Ser Gly Gly Gly Gly Ser Gly Gly Gly Gly Ser Ala
                    5                  10                  15
```